United States Patent
Xu et al.

(10) Patent No.: US 12,163,959 B2
(45) Date of Patent: Dec. 10, 2024

(54) EXTRACELLULAR VESICLE PROTEINS AND THEIR USE FOR CANCER DIAGNOSIS, PREDICTING RESPONSE TO THERAPY, AND TREATMENT

(71) Applicant: THE TRUSTEES OF THE UNIVERSITY OF PENNSYLVANIA, Philadelphia, PA (US)

(72) Inventors: Xiaowei Xu, Monmouth Junction, NJ (US); Wei Guo, Wynnewood, PA (US); Gang Chen, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 785 days.

(21) Appl. No.: 16/762,440

(22) PCT Filed: Nov. 9, 2018

(86) PCT No.: PCT/US2018/059981
§ 371 (c)(1),
(2) Date: May 7, 2020

(87) PCT Pub. No.: WO2019/094692
PCT Pub. Date: May 16, 2019

(65) Prior Publication Data
US 2020/0264185 A1    Aug. 20, 2020

Related U.S. Application Data

(60) Provisional application No. 62/583,901, filed on Nov. 9, 2017.

(51) Int. Cl.
*A61K 39/395* (2006.01)
*G01N 33/574* (2006.01)

(52) U.S. Cl.
CPC . *G01N 33/57488* (2013.01); *G01N 33/57423* (2013.01); *G01N 33/5743* (2013.01); *G01N 2800/52* (2013.01)

(58) Field of Classification Search
None
See application file for complete search history.

(56) References Cited

U.S. PATENT DOCUMENTS

| | | |
|---|---|---|
| 7,892,540 B2 | 2/2011 | Chen et al. |
| 8,168,179 B2 | 5/2012 | Honjo et al. |
| 9,045,545 B1 | 6/2015 | Clube |
| 2014/0038901 A1 | 2/2014 | Lyden et al. |
| 2015/0017660 A1 | 1/2015 | Ochiya |
| 2015/0044695 A1 | 2/2015 | Lozupone et al. |
| 2015/0071910 A1 | 3/2015 | Kowanetz et al. |
| 2015/0301058 A1 | 10/2015 | Schettini et al. |
| 2015/0346208 A1 | 12/2015 | Couto et al. |
| 2016/0122829 A1 | 5/2016 | Hammerman |
| 2016/0222118 A1 | 8/2016 | Chen et al. |
| 2017/0175197 A1 | 6/2017 | Gatalica et al. |
| 2018/0067121 A1 | 3/2018 | Naasani |
| 2018/0340945 A1 | 11/2018 | Mitsuhashi |

FOREIGN PATENT DOCUMENTS

| | | |
|---|---|---|
| CN | 101711360 A | 5/2010 |
| JP | 2017120263 A | 7/2017 |
| WO | 2009021322 A1 | 2/2009 |
| WO | 2011127585 A1 | 10/2011 |
| WO | 2012018538 A2 | 2/2012 |
| WO | 2015085096 A1 | 6/2015 |

OTHER PUBLICATIONS

Software translation of JP 2017-120263 A to Institute of Immunology Co Ltd, Jul. 6, 2017 (Year: 2017).*
Ludwig et al. (2017) 23: 4843-4854 (Year: 2017).*
Extended EP Search Report, U.S. Appl. No. 18/875,692, dated Oct. 21, 2021.
International Search Report and Written Opinion, PCT/US18/59981, dated Apr. 23, 2019.
Supplementary Partial EP Search Report, U.S. Appl. No. 18/875,692, dated Jul. 20, 2021.
Abiko, et al., "IFN-ε from lymphocytes induces PD-L1 expression and promotes progression of ovarian cancer", Br J Cancer. Apr. 28, 2015;112(9):1501-9. doi: 10.1038/bjc.2015.101. Epub Mar. 31, 2015. PMID: 25867264; PMCID: PMC4453666.
Andaloussi, et al., "Extracellular vesicles: biology and emerging therapeutic opportunities", Nat. Rev. Drug Discov. 12, 347-357 (2013) Abstract only.
Andreola, et al., "Induction of lymphocyte apoptosis by tumor cell secretion of FasL-bearing microvesicles", J. Exp. Med. 195, 1303-1316 (2002).
Aspeslagh, et al., "In the immuno-oncology era, is anti-PD-1 or anti-PD-L1 immunotherapy modifying the sensitivity to conventional cancer therapies?", Eur J Cancer. Dec. 2017;87:65-74. doi: 10.1016/j.ejca.2017.09.027. Epub Nov. 7, 2017, Abstract only.
Azuma, et al., "B7-H1 is a ubiquitous antiapoptotic receptor on cancer cells", Blood, Apr. 1, 2008 vol. 111, No. 7.
Baietti, et al., "Syndecan-syntenin-ALIX regulates the biogenesis of exosomes", Nat. Cell Biol. 14, 677-685 (2012) Abstract only.
Becker, et al., "Extracellular Vesicles in Cancer: Cell-to-Cell Mediators of Metastasis", Cancer Cell 30, 836-848 (2016).
Berchem, et al., "Hypoxic tumor-derived microvesicles negatively regulate NK cell function by a mechanism involving TGF-beta and miR23a transfer", Oncoimmunology 5, e1062968 (2016).

(Continued)

*Primary Examiner* — Michael D Pak
(74) *Attorney, Agent, or Firm* — Saul Ewing LLP; Kathryn Doyle; Justin Crotty

(57) ABSTRACT

Compositions and methods are disclosed for treating cancer patients and identifying patients with a malignancy that are likely to respond to treatment with anti-PD-1/PD-L1 and other anti-cancer and immune-modulating therapeutics.

Figure 1A:
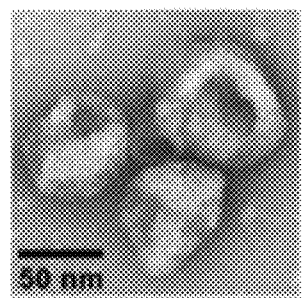

6 Claims, 27 Drawing Sheets
Specification includes a Sequence Listing.

(56) References Cited

OTHER PUBLICATIONS

Bissig, et al., "ALIX and the multivesicular endosome: ALIX in Wonderland", Trends Cell Biol, 24, 19-25 (2014) Abstract only.
Brahmer, et al., "Phase I study of single-agent anti-programmed death-1 (MDX-1106) in refractory solid tumors: Safety, clinical activity, pharmacodynamics, and immunologic correlates", J. Clin. Oncol. 28, 3167-3175 (2010).
Brahmer, et al., "Safety and Activity of Anti-PD-L1 Antibody in Patients with Advanced Cancer", N Engl J Med 2012; 366:2455-2465 DOI: 10.1056/NEJMoa1200694.
Chemnitz, et al., "SHP-1 and SHP-2 associate with immunoreceptor tyrosine-based switch motif of programmed death 1 upon primary human T cell stimulation, but only receptor ligation prevents T cell activation", J. Immunol. 173, 945-954 (2004).
Chen, et al., "Anti-PD-1/PD-L1 therapy of human cancer: past, present, and future", J. Clin. Invest. 125, 3384-3391 (2015).
Chen, et al., "Development of a sandwich ELISA for evaluating soluble PD-L1 (CD274) in human sera of different ages as well as supernatants of PD-L1+cell lines", Cytokine 56, 231-238 (2011) Abstract only.
Cheng, et al., "Exosomes from Melatonin Treated Hepatocellularcarcinoma Cells Alter the Immunosupression Status through STAT3 Pathway in Macrophages", Int J Biol Sci. May 1, 20176;13(6):723-734. doi: 10.7150/ijbs.19642.eCollection 2017.
Chowdhury, et al., "Programmed death-ligand 1 overexpression is a prognostic marker for aggressive papillary thyroid cancer and its variants", Oncotarget 7, 32318-32328 (2016).
Colombo, et al., "Analysis of ESCRT functions in exosome biogenesis, composition and secretion highlights the heterogeneity of extracellular vesicles", J. Cell Sci. 126, 5553-5565 (2013).
Colombo, et al., "Biogenesis, secretion, and intercellular interactions of exosomes and other extracellular vesicles", Annu. Rev. Cell Dev. Biol. 30, 255-289 (2014) Abstract only.
Ding, et al., "Pancreatic cancer-derived exosomes transfer miRNAs to dendritic cells and inhibit RFXAP expression via miR-212-3p", Oncotarget 6, 29877-29888 (2015).
Dong, et al., "Tumor-associated B7-H1 promotes T-cell apoptosis: a potential mechanism of immune evasion", Nat. Med. 8, 793-800 (2002) Abstract only.
Finkelmeier, et al., "High levels of the soluble programmed death-ligand (sPD-L1) identify hepatocellular carcinoma patients with a poor prognosis", Eur. J. Cancer 59, 152-159 (2016) Abstract only.
Frigola, et al., "Identification of a soluble form of B7-H1 that retains immunosuppressive activity and is associated with aggressive renal cell carcinoma", Clin. Cancer Res. 17, 1915-1923 (2011).
Garcia-Diaz, et al., "Interferon Receptor Signaling Pathways Regulating PD-L1 and PD-L2 Expression", Cell Rep. 19, 1189-1201 (2017).
Gutierrez-Vazquez, et al., "Transfer of extracellular vesicles during immune cell-cell interactions", Immunol. Rev. 251. 125-142 (2013).
Haderk, et al., "Tumor-derived exosomes modulate PD-L1 expression in monocytes", Sci Immunol. Jul. 28, 2017;2 (13). pil: eaah5509. doi: 10.1126/sciimmunol.aah5509. Abstract only.
Henne, et al., "Molecular mechanisms of the membrane sculpting ESCRT pathway", Cold Spring. Harb. Perspect. Biol. 5 (2013).
Herbst, et al., "Predictive correlates of response to the anti-PD-L1 antibody MPDL3280A in cancer patients", Nature 515, 563-567 (2014).
Horita, et al., "Identifying Regulatory Posttranslational Modifications of PD-L1: A Focus on Monoubiquitinaton", Neoplasia 19, 346-353 (2017).
Huang, et al., "T-cell invigoration to tumour burden ratio associated with anti-PD-1 response", Nature 545, 60-65 (2017).
Juneja, et al., "PD-L1 on tumor cells is sufficient for immune evasion in immunogenic tumors and inhibits CD8 T cell cytotoxicity", J. Exp. Med. 214, 895-904 (2017).
Kalluri, et al., "The biology and function of exosomes in cancer", J. Clin. Invest. 126, 1208-1215 (2016).
Kamphorst, et al., "Proliferation of PD-1+CD8 T cells in peripheral blood after PD-1-targeted therapy in lung cancer patients", Proc. Natl. Acad. Sci. U S A 114, 4993-4998 (2017).
Kim, et al., "Fas ligand-positive membranous vesicles isolated from sera of patients with oral cancer induce apoptosis of activated T lymphocytes", Clin. Cancer Res. 11, 1010-1020 (2005); p. 1010 only.
Larkin, et al., "Combined Nivolumab and Ipilimumab or Monotherapy in Untreated Melanoma", N. Engl. J. Med. 373, 23-34 (2015).
Lau, et al., "Tumour and host cell PD-L1 is required to mediate suppression of anti-tumour immunity in mice", Nat. Commun. 8, 14572 (2017).
Li, et al., "Glycosylation and stabilization of programmed death ligand-1 suppresses T-cell activity", Nat. Commun. 7, 12632 (2016).
Lim, et al., "Deubiquitination and Stabilization of PD-L1 by CSN5", Cancer Cell 30, 925-939 (2016).
Lipson, et al., "Durable cancer regression off-treatment and effective reinduction therapy with an anti-PD-1 antibody", Clin. Cancer Res. 19, 462-468 (2013).
Lo Cicero, et al., "Extracellular vesicles shuffling intercellular messages: for good or for bad", Curr. Opin. Cell Biol. 35, 69-77 (2015) Abstract only.
Mahoney, et al., "PD-L1 Antibodies to Its Cytoplasmic Domain Most Clearly Delineate Cell Membranes in Immunohistochemical Staining of Tumor Cells", Cancer Immunol. Res. 3, 1308-1315 (2015).
Mandal, et al., "Dual Faces of IFNγ in Cancer Progression: A Role of PD-L1 Induction in the Determination of Pro- and Antitumor Immunity", Clin Cancer Res. May 15, 2016;22(10):2329-34. doi: 10.1158/1078-0432.CCR-16-0224. Epub Mar. 25, 2016. PMID: 27016309.
Martinez, et al., "Resistance to HER2-targeted anti-cancer drugs is associated with immune evasion in cancer cells and their derived extracellular vesicles", Oncoimmunology, vol. 6, No. 12, Aug. 11, 2017.
Melo, et al., "Glypican-1 identifies cancer exosomes and detects early pancreatic cancer", Nature 523, 177-182 (2015).
Mignot, et al., "Tumor exosome-mediated MDSC activation", Am. J. Pathol. 178, 1403-1404 (2011).
Muller, et al., "Exosomes isolated from plasma of glioma patients enrolled in a vaccination trial reflect antitumor immune activity and might predict survival", Oncoimmunology. Mar. 2, 2015;4(6):e1008347. eCollection Jun. 2015.
Muller, et al., "Tumor-derived exosomes regulate expression of immune function-relatedsubsets", Sci. Rep. 6, 20254 (2016).
Obeid, et al., "PD-L1, PD-L2 and PD-1 expression in metastatic melanoma: Correlation with tumor-infiltrating immune cells and clinical outcome", Oncoimmunology 5, e1235107 (2016).
Ohaegbulam, et al., "Human cancer immunotherapy with antibodies to the PD-1 and PD-L1 pathway", Trends Mol Med. 2015;21(1):24-33.
Pardoll, "The blockade of immune checkpoints in cancer immunotherapy", Nat. Rev. Cancer 2012);12(4):252-264.
Patel, et al., "PD-L1 Expression as a Predictive Biomarker in Cancer Immunotherapy", Mol. Cancer Ther. 14, 847-856 (2015).
Peinado, et al., "Melanoma exosomes educate bone marrow progenitor cells toward a pro-metastatic phenotype through MET", Nat. Med. 18, 883-891 (2012).
Raposo, et al., "Extracellular vesicles: exosomes, microvesicles, and friends", J. Cell. Biol. 200, 373-383 (2013).
Reck, et al., "Pembrolizumab versus Chemotherapy for PD-L1-Positive Non-Small-Cell Lung Cancer", N. Engl. J. Med. 375, 1823-1833 (2016).
Ribas, et al., "Association of Pembrolizumab With Tumor Response and Survival Among Patients With Advanced Melanoma", JAMA. 315, 1600-1609 (2016) Abstract only.
Ricklefs, et al., "Immune Evasion Mediated By PD-LI On Glioblastoma Derived Extracellular Vesicles", Neuro-Oncology, vol. 19, May 1, 2017.
Robbins, et al., "Regulation of immune responses by extracellular vesicles", Nat. Rev. Immunol. 14, 195-208 (2014).
Rossille, et al., "High level of soluble programmed cell death ligand 1 in blood impacts overall survival in aggressive diffuse large

(56) References Cited

OTHER PUBLICATIONS

B-Cell lymphoma: results from a French multicenter clinical trial", Leukemia 28, 2367-2375 (2014) Abstract only.
Schmidt, et al., "The ESCRT machinery", Curr. Biol. 22, R116-120 (2012).
Sznol, et al., "Antagonist antibodies to PD-1 and B7-H1 (PD-L1) in the treatment of advanced human cancer", Clin. Cancer Res. 19, 1021-1034 (2013).
Taube, et al., "Colocalization of Inflammatory Response with B7-H1 Expression in Human Melanocytic Lesions Supports an Adaptive Resistance Mechanism of Immune Escape", Science Translational Medicine Mar. 28, 2012: vol. 4, Issue 127, pp. 127ra37; DOI: 10.1126/scitransimed.3003689.
Taylor, et al., "T-cell apoptosis and suppression of T-cell receptor/CD3-zeta by Fas ligand-containing membrane vesicles shed from ovarian tumors", Clin. Cancer Res. 9, 5113-5119 (2003).
Theodoraki, et al., "P89 Plasma-derived exosomes carrying CTLA-4, PD-1 and PD-LI in head and neck squamous cell carcinoma patients treated with immunotherapy is associated with disease outcome", Journal for Immunotherapy of Cancer, vol. 5, Nov. 1, 2017.
Thery, et al., "Isolation and characterization of exosomes from cell culture supernatants and biological fluids", Curr. Protoc. Cell Biol. Chapter 3, Unit 3 22 (2006) Abstract only.
Tibes, et al., "Reverse phase protein array: validation of a novel proteomic technology and utility for analysis of primary leukemia specimens and hematopoietic stem cells", Mol. Cancer Ther. 5, 2512-2521 (2006).
Topalian, et al., "Mechanism-driven biomarkers to guide immune checkpoint blockade in cancer therapy", Nat. Rev. Cancer 16, 275-287 (2016).
Topalian, et al., "Safety, activity, and immune correlates of anti-PD-1 antibody in cancer", N. Engl. J. Med. 366, 2443-2454 (2012).
Tumeh, et al., "PD-1 blockade induces responses by inhibiting adaptive immune resistance", Nature 515, 568-571 (2014).
Valenti, et al., "Human tumor-released microvesicles promote the differentiation of myeloid cells with transforming growth factor-beta-mediated suppressive activity on T lymphocytes", Cancer Res. 66, 9290-9298 (2006).
Villaruz, et al., "The clinical utility of PD-L1 testing in selecting non-small cell lung cancer patients for PD1/PD-L1-directed therapy", Clin Pharmacol Ther. Sep. 2016;100(3):212-4. doi: 10.1002/cpt. 385. Epub Jun. 3, 2016.
Wang, et al., "Serum levels of soluble programmed death ligand 1 predict treatment response and progression free survival in multiple myeloma", Oncotarget 6, 41228-41236 (2015).
Whiteside, "Exosomes and tumor-mediated immune suppression", J. Clin. Invest. 126, 1216-1223 (2016).
Wieckowski, et al., "Tumor-derived microvesicles promote regulatory T cell expansion and induce apoptosis in tumor-reactive activated CD8+T lymphocytes", J. Immunol. 183, 3720-3730 (2009).
Zaretsky, et al., "Mutations Associated with Acquired Resistance to PD-1 Blockade in Melanoma", N. Engl. J. Med. 375, 819-829 (2016).
Zheng, et al., "Human Cancer Immunotherapy with PD-1/PD-L1 Blockade", Biomark Cancer. 2015; 7(Suppl 2): 15-18.
Zhou, et al., "Soluble PD-L1 as a Biomarker in Malignant Melanoma Treated with Checkpoint Blockade", Cancer Immunol. Res. 5, 480-492 (2017).
Zou, et al., "PD-L1 (B7-H1) and PD-1 Pathway Blockade for Cancer Therapy: Mechanisms, Response Biomarkers and Combinations", Sci Transl Med. Mar. 2, 2016; 8(328): 328rv4. doi:10.1126/scitransimed.aad7118.

\* cited by examiner

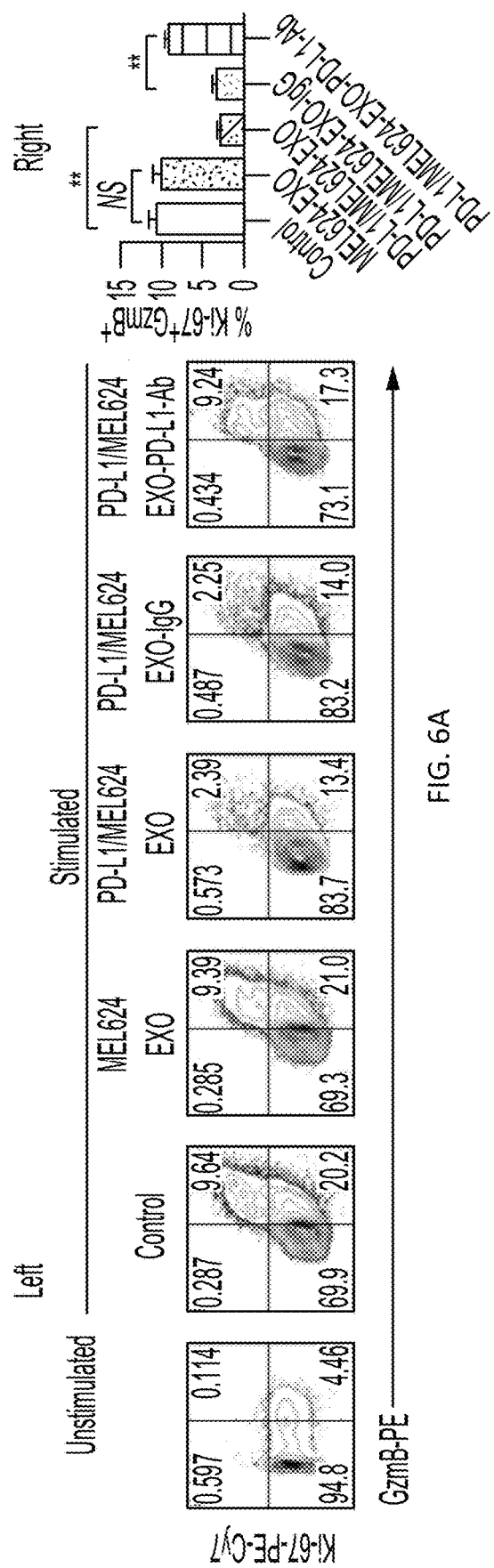
FIG. 6A
FIG. 6B
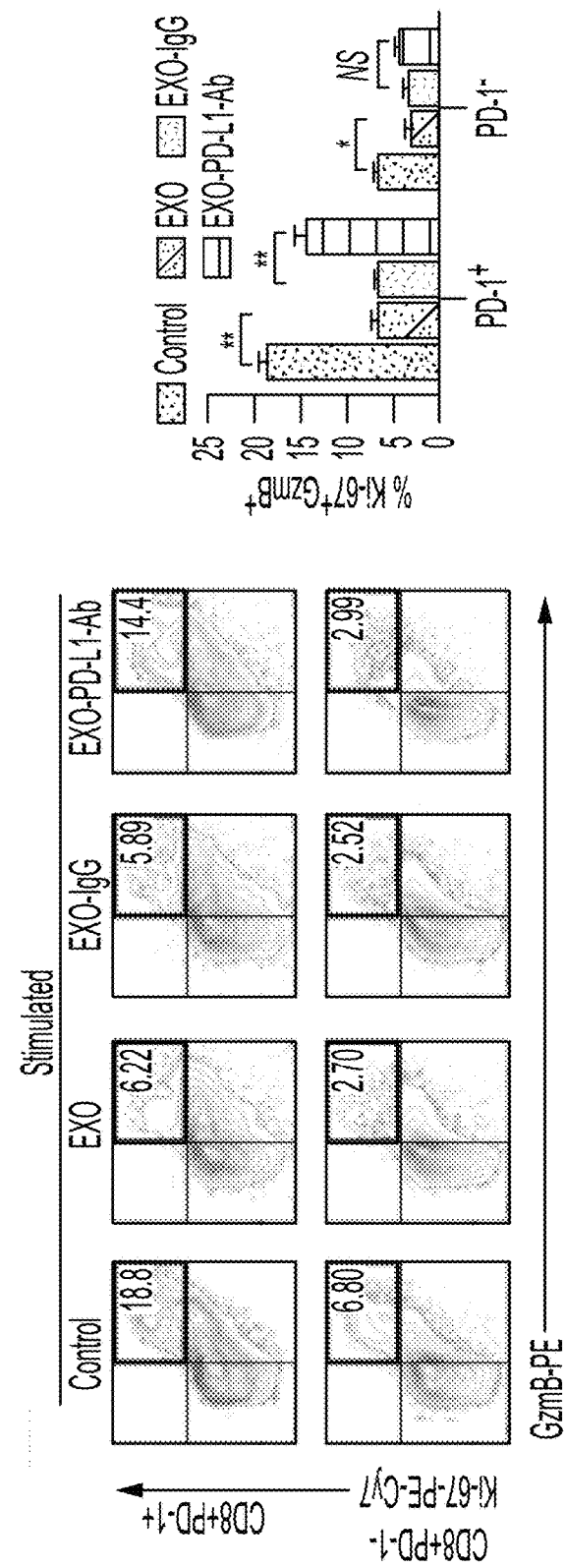
FIG. 6C

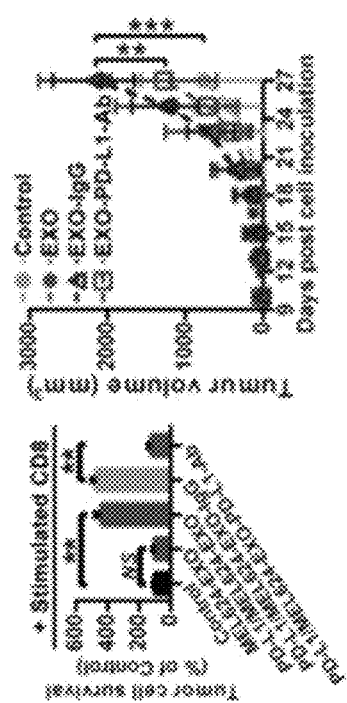
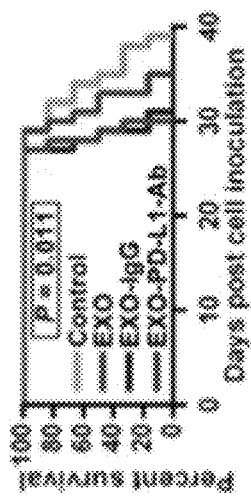
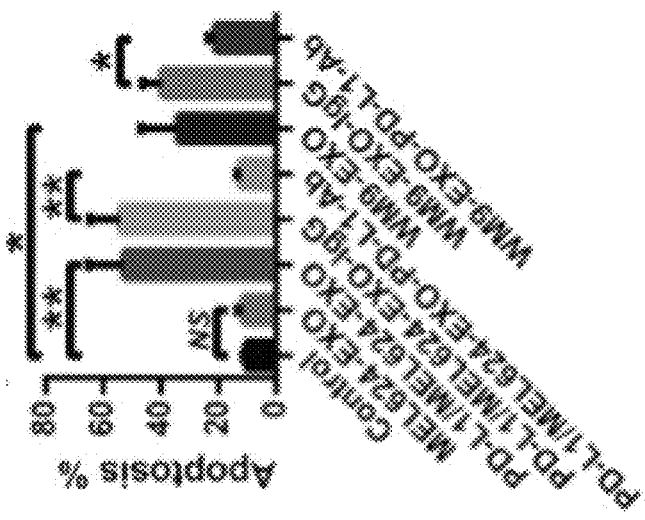
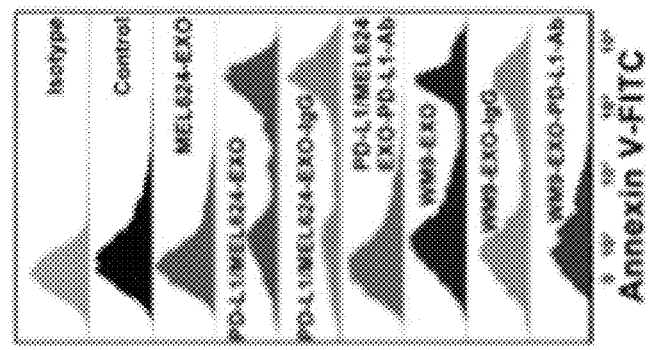
FIG. 6D
FIG. 6F
FIG. 6G
FIG. 6H
FIG. 6I
FIG. 6E

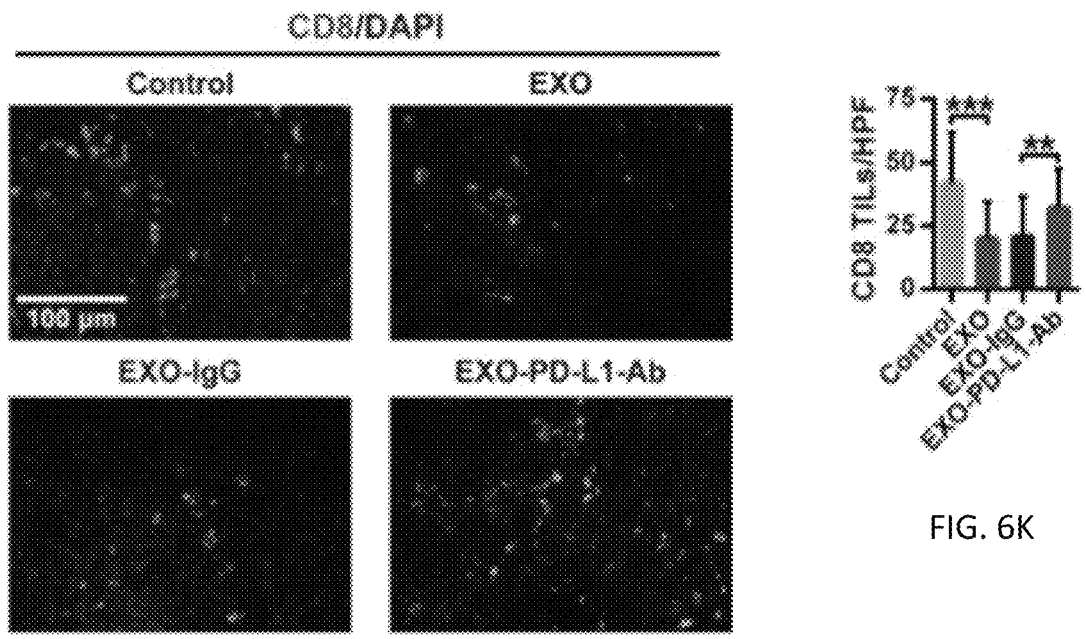
FIG. 6J
FIG. 6K
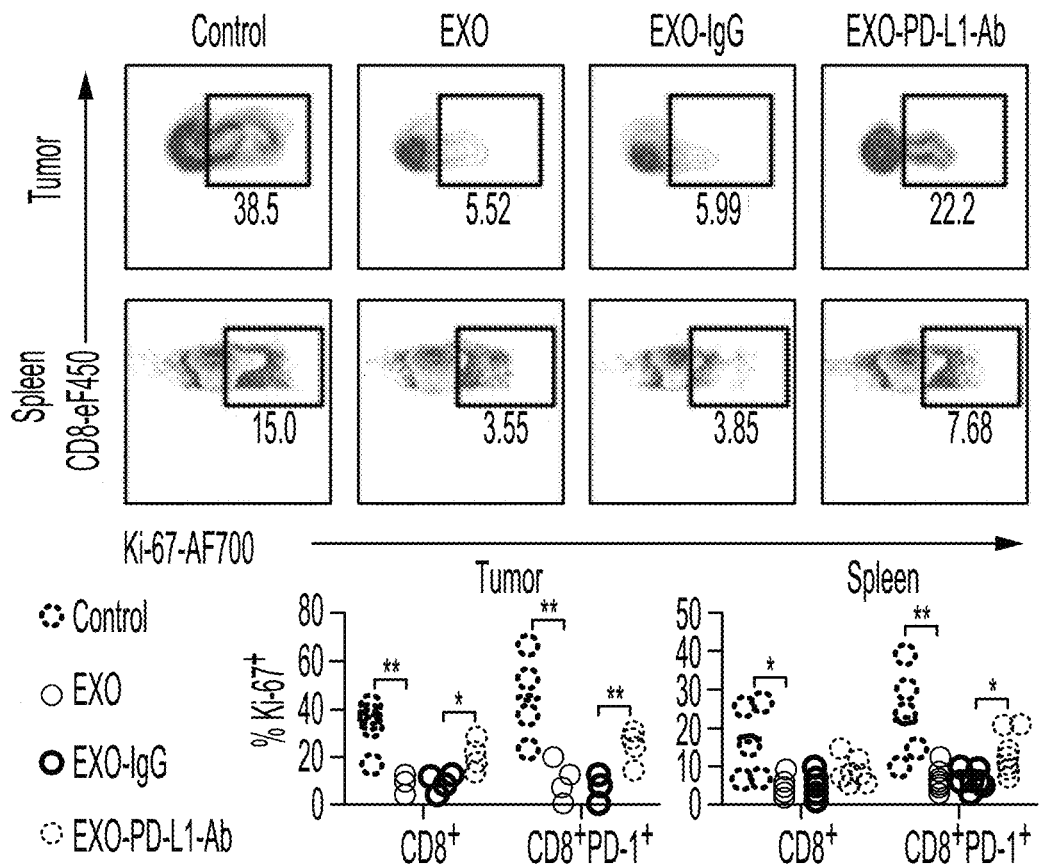
FIG. 6L

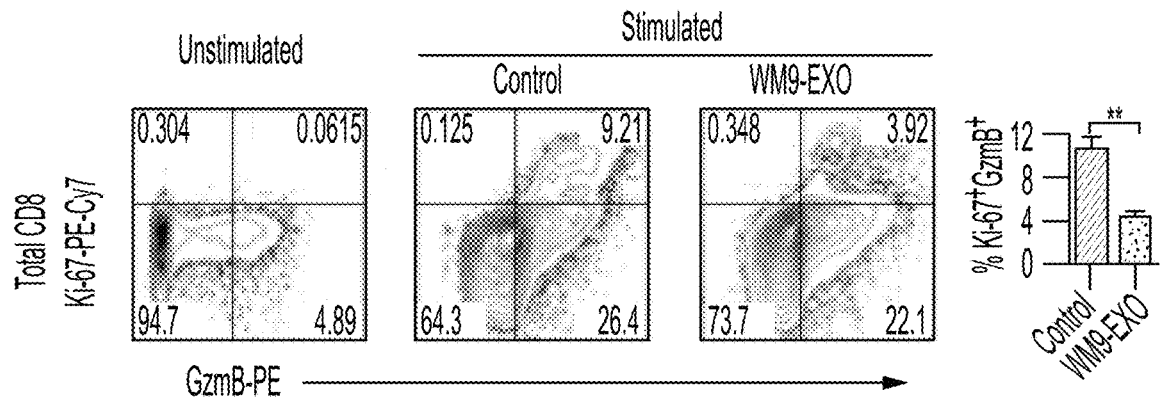
FIG. 7A
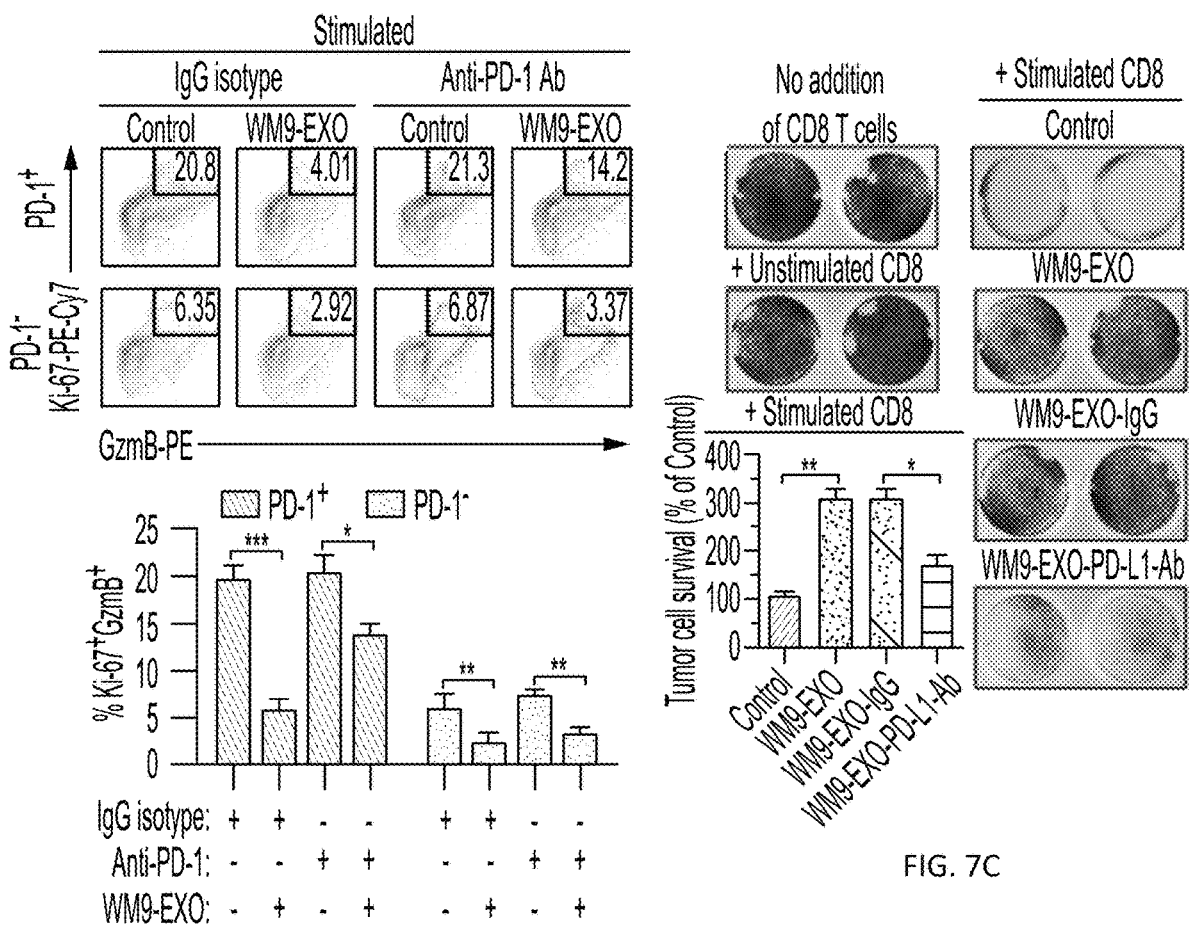
FIG. 7B
FIG. 7C

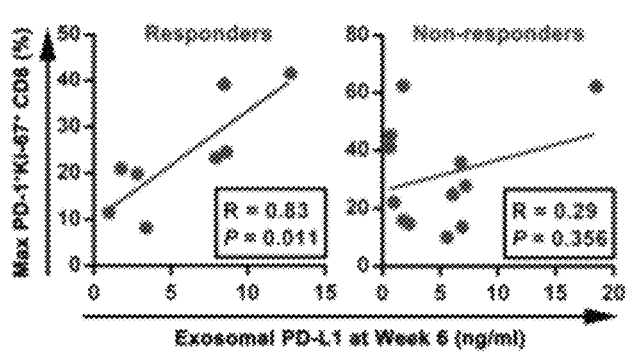 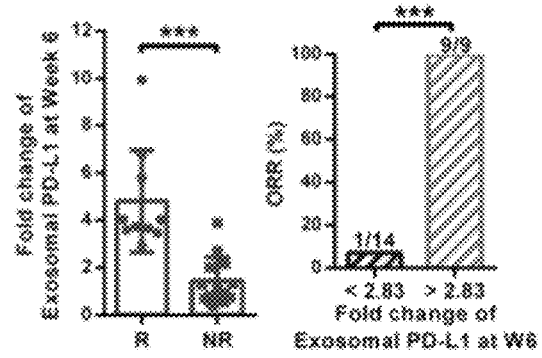
FIG. 10H  FIG. 10J  FIG. 10L
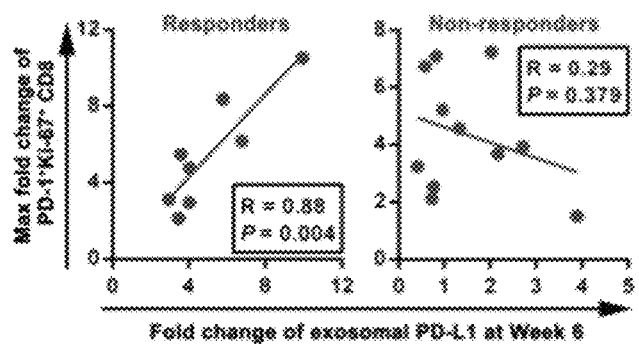 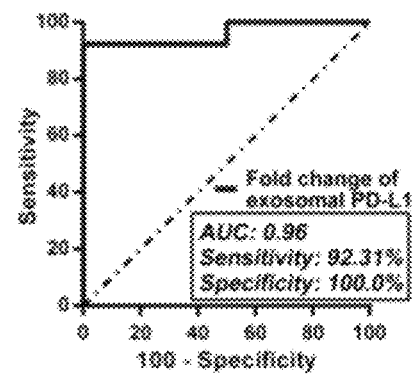
FIG. 10I  FIG. 10K

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: human HRS shRNA

<400> SEQUENCE: 1
gcacgtcttt ccagaattca a                                        21

```
<210> SEQ ID NO 2
<211> LENGTH: 21
<212> TYPE: DNA
<213> ORGANISM: Artificial Sequence
<220> FEATURE:
<223> OTHER INFORMATION: murine PD-L1 shRNA

<400> SEQUENCE: 2
gcgttgaaga tacaagctca a                                              21
```

EXTRACELLULAR VESICLE PROTEINS AND THEIR USE FOR CANCER DIAGNOSIS, PREDICTING RESPONSE TO THERAPY, AND TREATMENT

CROSS-REFERENCE TO RELATED APPLICATIONS

The present application is a 35 U.S.C. § 371 national phase application from, and claims priority to, International Application No. PCT/US2018/059981, filed Nov. 9, 2018, and published under PCT Article 21 (2) in English, which claims priority under 35 U.S.C. § 119 (e) to U.S. Provisional Application No. 62/583,901 filed Nov. 9, 2017, all of which applications are incorporated herein by reference in their entireties.

STATEMENT REGARDING FEDERALLY SPONSORED RESEARCH OR DEVELOPMENT

This invention was made with government support under CA174523 and GM085146 awarded by the National Institutes of Health. The government has certain rights in the invention.

FIELD OF THE INVENTION

This invention relates to the fields of oncology, immunotherapy and medicine. More specifically, the invention provides biomarkers and methods of use thereof which aid the clinician in monitoring response to treatment, identifying those patients most likely to benefit from treatment, and a new treatment method to inhibit cancer metastasis. The markers disclosed herein are also useful in assays to identify therapeutic agents useful for the treatment of cancer.

BACKGROUND OF THE INVENTION

Several publications and patent documents are cited throughout the specification in order to describe the state of the art to which this invention pertains. Each of these citations is incorporated herein by reference as though set forth in full.

Immunocheckpoint ligand proteins such as PD-L1, PD-L2, B7H3, and B7H4, are transmembrane proteins expressed in a variety of cell types including tumor cells. These proteins play a critical role in immunosuppression as they bind to receptors such as PD-1 on activated T cells to elicit immune checkpoint responses (Dong et al., 2002). Identification of the immunocheckpoint signaling pathway has stemmed the development of immune checkpoint blockade-based therapies to treat many types of cancers. For example, blocking antibodies that target the PD-L1/PD-1 axis have shown remarkable promise in the treatment of number of solid tumors, including metastatic melanoma (Chen and Han, 2015; Topalian et al., 2016). However, only a minority of patients respond to the therapy and the responses are often partial or short-lived (Ribas et al., 2016; Zaretsky et al., 2016).

The current model for PD-L1-mediated immunosuppression is centered on the direct interaction between PD-L1 on tumor cell surface and PD-1 on T cells. This interaction delivers a potent inhibitory signal that induces functional "exhaustion" or apoptosis of T cells (Chen and Han, 2015; Topalian et al., 2016). PD-L1 on the cancer cell surface can locally inactivate immune cells as an adaptive response to immune pressure (Juneja et al., 2017; Lau et al., 2017). Several clinical observations, however, also suggest that the cancer cell surface PD-L1 is not the only biologically active form of PD-L1. PD-L1 is present not only on cancer cell surface, but also in the cytoplasm (Chowdhury et al., 2016; Mahoney et al., 2015; Obeid et al., 2016; Sznol and Chen, 2013). Moreover, soluble PD-L1 proteins have been identified in the blood samples of patients with melanoma, renal cell carcinoma, hepatocellular carcinoma, multiple myeloma, and B-cell lymphoma; the level of blood PD-L1 proteins appears to correlate with tumor progression and patients' overall survival (Finkelmeier et al., 2016; Frigola et al., 2011; Rossille et al., 2014; Wang et al., 2015; Zhou et al., 2017).

Despite the recent success of the immune checkpoint blockade therapies, patient response is often partial or short-lived. A better molecular understanding of the interplay between tumor cells and the immune system is needed to improve current therapies and to identify patients most likely to respond to therapy.

SUMMARY OF THE INVENTION

In accordance with the present invention, a method for identifying a subject responsive to anti-cancer therapy is provided. An exemplary method comprises obtaining a first biological sample collected from a subject prior to treatment, administering one or more anti-cancer agents to said subject and collecting a second biological sample from said treated subject, detecting levels of circulating extracellular vesicle PD-L1 and/or interferon γ (IFNγ) in said first and second biological samples, and identifying subjects responsive to treatment when there is an increased level of extracellular vesicle PD-L1 and/or IFNγ in said second biological sample relative to said first biological sample and/or identifying the subject as responsive to treatment where there is an increase in the of extracellular vesicle PD-L1 and IFNγ levels in said second biological sample relative to said first biological sample.

In one aspect, the cancer is melanoma, and the anti-cancer therapy is directed to PD-1/PD-L1 and includes without limitation, pembrolizumab, nivolumab, atezolizumab, avelumab, durvalumab, antibodies immunologically specifically targeting PD1/PDL1 for cancer treatment and small molecules specifically targeting PD1/PDL1 for cancer treatment. Other cancers to be assessed or treated with the method described herein, include for example, lung cancer, liver cancer, prostate cancer, colon cancer, kidney cancer, breast cancer, head and neck cancer, bladder cancer, gastric cancer, esophageal cancer, nasophyringeal cancer, lymphoma, Merkel cell carcinoma, cancer with mismatch repair deficiency or any other cancers that may be treated with anti-PD1/PDL1 therapy.

As indicated above, the first and second samples are taken before and after therapy. The method can also comprise taking subsequent additional samples after the second sample is obtained to monitor disease status in the subject. The second samples can be taken within days or weeks or months after therapy, depending on the treatment regimen utilized to treat the cancer and the particular type of cancer being treated. The second sample can be obtained 1, 2, 3, 4, 6, 8, 9, 10, 12, or 16 weeks or so after the first sample is taken. In certain instances, the samples may obtained days apart, e.g., 2, 3, 4, 5, 6, 7 or 10 days after treatment.

In certain embodiments, the method further comprises determining the ratio between blood exatracellular vesicle PD-L1 protein levels before and after said treatment. The method can also comprise determining the ratio of IFNγ levels before and after treatment. In other embodiments, the ratio of PD-L1 and IFNγ levels are determined before and after treatment. The aforementioned method can further comprise isolation of extracellular vesicles including exosomes comprising one or more of proteins associated with malignant transformation or progression such as, Akt, Wnt5A, MAPK1, HSP70, TRAP1, HSP90, SerpinH1, VEGFC, R-RAS, HLA-G5, BRAF, NRAS, KIT, TP53, PTEN, EGFR, HER2, ALK, AKT1, KRAS, MET, RET, RHOA, ARID1A, CDH1 or mutants thereof, wherein said extracellular vesicles including exosomes are optionally isolated before and after anti-cancer therapy.

A method of detecting cancer cell-derived PD-L1 containing vesicles in a biological sample obtained from a cancer patient selected from the group consisting of PD-L1 exosomes, extracellular vesicles, ectosomes, apoptotic bodies, and oncosomes is also provided. One such method comprises contacting said sample with a reagent or reagents that specifically bind PD-L1; and detecting formation of a binding complex comprising said reagent or reagents bound to said cancer derived PD-L1 containing vesicles. The method can further comprise isolation of said PD-L1 containing vesicles from said binding complex.

In another aspect of the invention, a method for the isolation of cancer-protein containing exosomes or cancer-protein containing extracellular vesicles from a biological fluid sample is provided. An exemplary method comprises obtaining a sample from a patient, incubating the sample with a reagent that specifically binds said cancer protein and isolating the reagent thereby isolating cancer protein containing exosomes or extracellular vesicles from said sample, wherein said cancer protein is selected from the group consisting of BRAF, NRAS, KIT, TP53, PTEN, EGFR, HER2, ALK, AKT1, MET, RET, RHOA, ARID1A, and CDH1, Wnt5A, MAPK1, HSP70, TRAP1, HSP90, SerpinH1, VEGFC, R-RAS, HLA-G5, and mutated proteins thereof, the presence of said cancer protein in said exosomes or said extracellular vesicles being indicative of cancer. In certain embodiments, the presence of such proteins is associated with metastatic cancer. The method can further comprise incubating the sample with a reagent that specifically binds CD63 or CD274.

The invention also provides a method for treating metastatic cancer associated with aberrant circulating extracellular vesicle and/or exosomal PD-L1 levels. An exemplary method comprises obtaining a biological sample from a patient; contacting said sample with an agent which forms a specific binding pair with blood PD-L1, thereby forming a binding complex, said PD-1/PD-L1 being present in an exosome or an extracellular vesicle; removing said binding complex from said sample, thereby depleting blood levels of PD-1/PDL1. In a preferred embodiment, the sample is blood and said contacting and removing occurs during plasmapheresis. In this approach, the filtered blood is reinfused into the subject. Cancers to be treated using the aforementioned method, include, without limitation, melanoma, lung cancer, liver cancer, prostate cancer, colon cancer, kidney cancer, breast cancer, head and neck cancer, bladder cancer, gastric cancer, lymphoma, Merkel cell carcinoma, cancer with mismatch repair deficiency or other cancers that may be treated with anti-PD1/PDL1 therapy.

In another aspect of the invention, a method of detecting immune cell-derived protein containing vesicles in a biological sample obtained from a cancer patient is disclosed. In certain embodiments, the vesicles are selected from the group consisting of immune cell derived protein containing exosomes, extracellular shedding vesicles, ectosomes, apoptotic bodies, and oncosomes. Isolation is performed by contacting the sample with a reagent or reagents that specifically bind said immune cell derived protein; and detecting formation of a binding complex comprising said reagent or reagents bound to said immune cell derived protein containing vesicles, wherein said immune cell derived protein is selected from the group consisting of one or more of CD109, CD151, CD276, CD44, CD46, CD47, CD55, CD58, CD59, CD70, CD9, CD95, CD97, CD99, and B7H4. The method can further comprise isolation of exosomes comprising CD63 and CD81.

Also provided is a method of detecting immune cell-derived protein containing extracellular vesicles in a biological sample obtained from a cancer patient. Such vesicles include, without limitation, immune cell derived protein containing exosomes, extracellular shedding vesicles, ectosomes, apoptotic bodies, and oncosomes. An exemplary method comprises contacting said sample with a reagent or reagents that specifically bind the immune cell derived protein; and detecting formation of a binding complex comprising said reagent or reagents bound to said immune cell derived protein containing vesicles, wherein said immune cell derived protein is selected from the group consisting of IFNγ the presence of said immune cell protein in said exosomes or said extracellular vesicles indicating the type or functional status of said immune cells. The method described above can further entail incubating the sample with a reagent that specifically binds CD9, CD63, and CD81. Other immune cell-derived protein containing vesicles to be detected, include, for example, one or more of CD3, CD4, CD8, CD11, CD14, CD16, CD19, CD20, CD24, CD25, CD27, CD38 CD45, CD68, CD80, CD86, CD138, CD152, CD160, CD223, CD244, CD274, CD276 and CD366.

In yet another embodiment, a kit for practicing any of the methods described above is provided.

BRIEF DESCRIPTIONS OF THE DRAWINGS

Figure 1B:
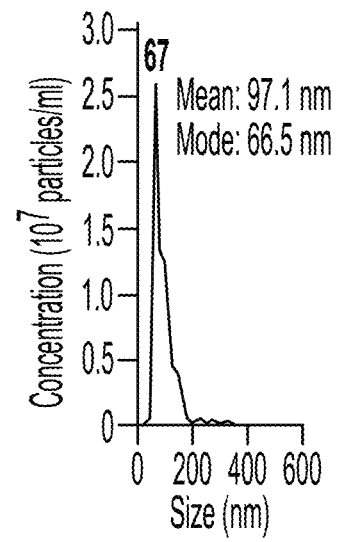
Figure 1C:
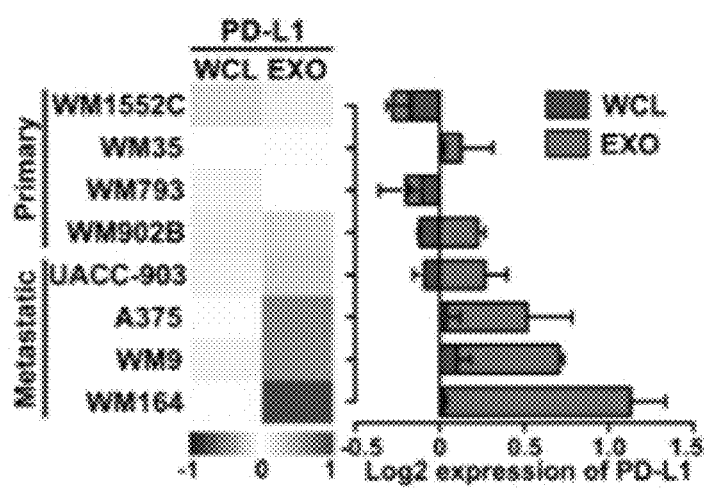
Figure 1D:
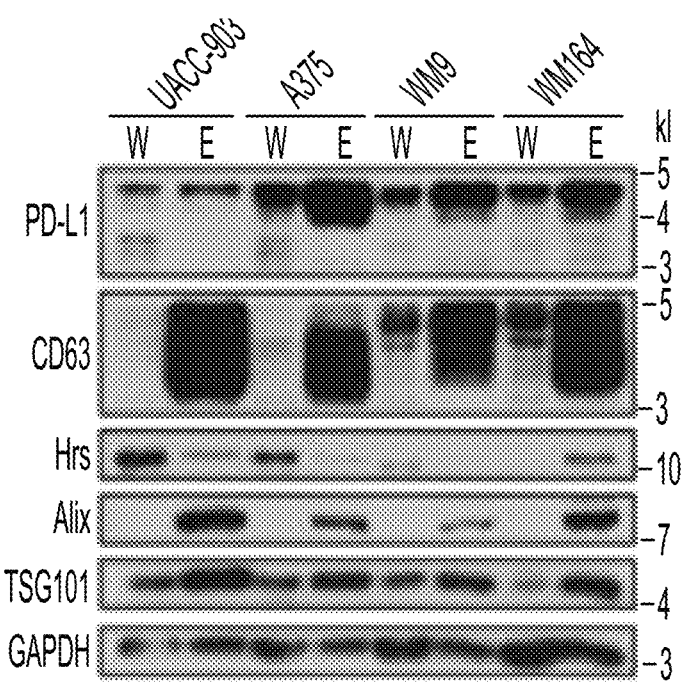
Figure 1E:
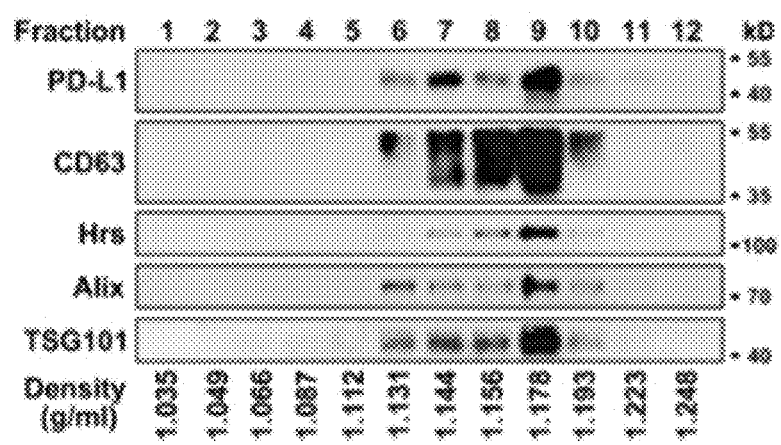
Figure 1F:
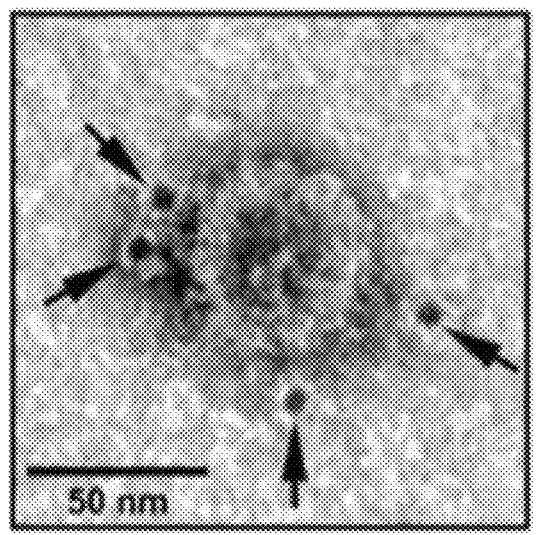
Figure 1G:
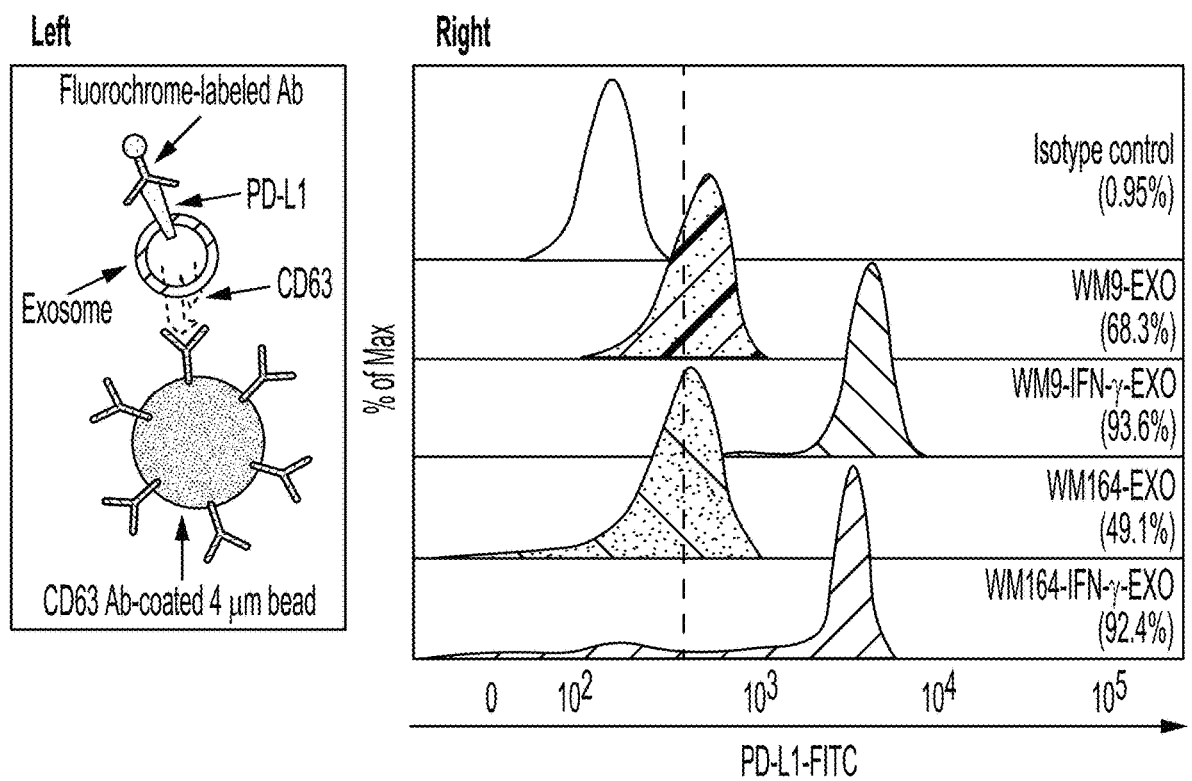
Figure 1H:
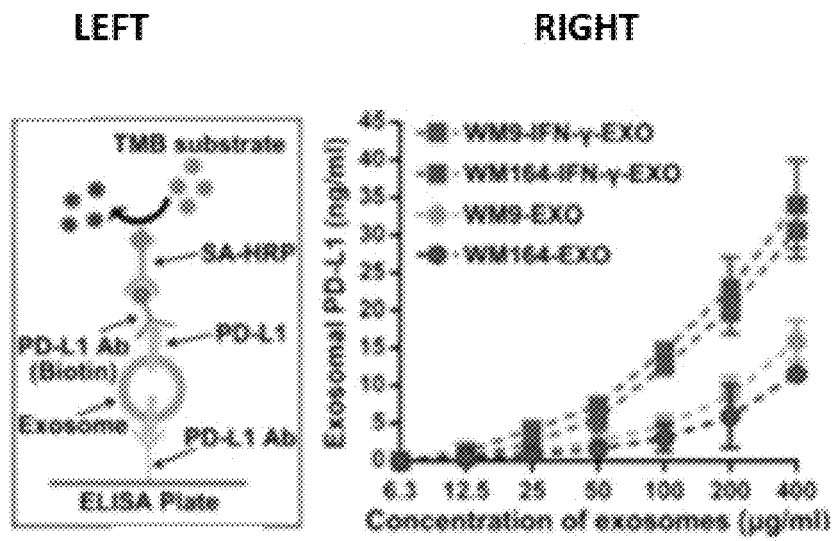
Figure 1I:
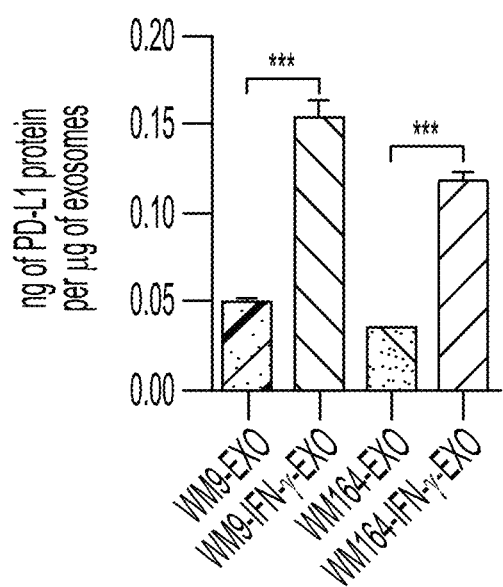
Figure 1J:
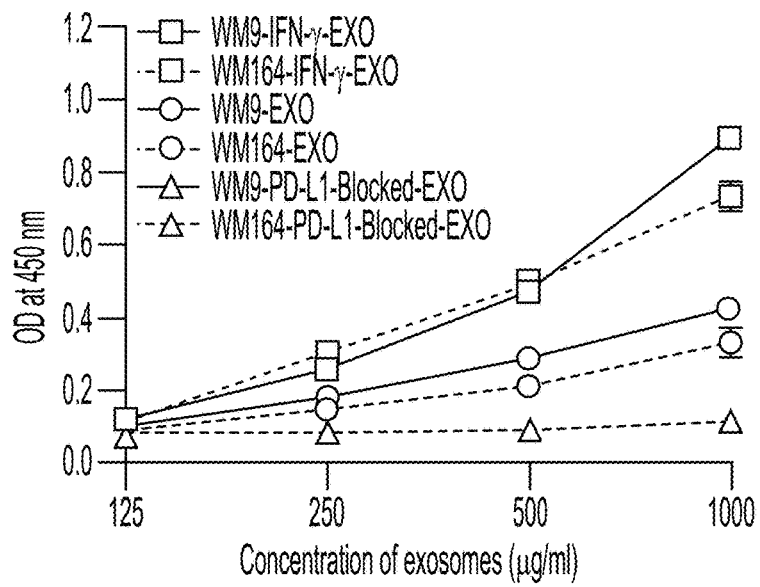
Figure 1K:
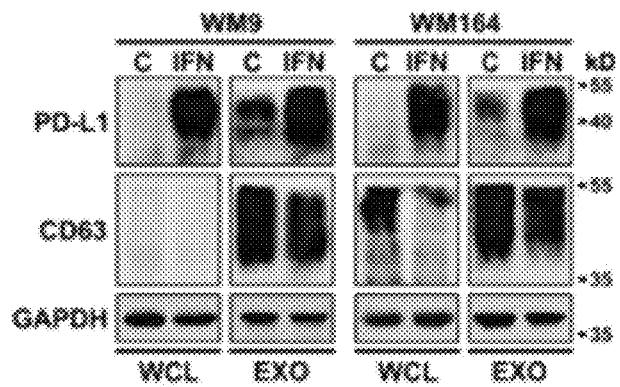
Figure 1L:
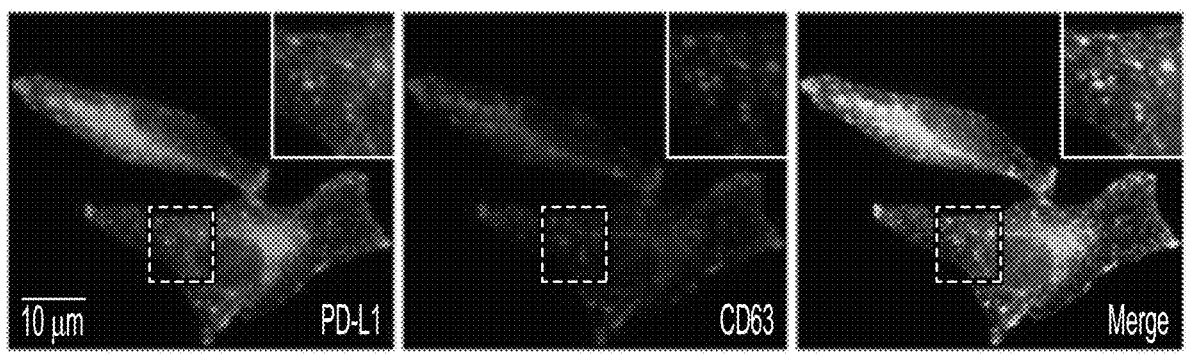
Figure 1M:
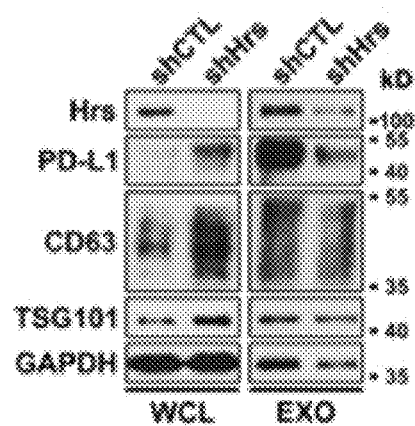
Figure 1N:
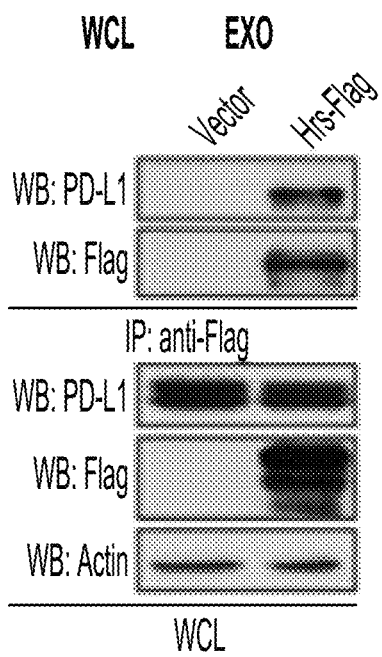

FIGS. 1A-1N. Melanoma cell-derived exosomes carry PD-L1 proteins on their surface. (FIG. 1A) A representative TEM image of exosomes purified from the culture supernatant of human melanoma cells. (FIG. 1B) Characterization of the purified exosomes using NanoSight nanoparticle tracking system. (FIG. 1C) Heatmap of reverse phase protein array (RPPA) data showing the levels of PD-L1 in the whole cell lysate ("WCL") and the exosomes ("EXO") secreted by primary or metastatic melanoma cell lines (left panel). The Log 2 transformed RPPA data is shown at the right panel. See FIG. 2A for statistical analysis. (FIG. 1D) Immunoblots for PD-L1 in the whole cell lysate ("W") and purified exosomes ("E") from different metastatic melanoma cell lines. The same amounts of whole cell lysates and exosome proteins were loaded. CD63, Hrs, Alix, and TSG101 were used as exosome markers. GAPDH was used as the loading control. (FIG. 1E) Density gradient centrifugation confirming that PD-L1 secreted by metastatic melanoma cells co-fractionated with exosome markers CD63, Hrs, Alix, and TSG101. (FIG. 1F) A representative TEM image of melanoma cell-derived exosomes immunogold-labeled with a monoclonal antibody against the extracellular domain of PD-L1. Arrowheads indicate 5-nm gold particles. (FIG. 1G) Diagram of flow cytometric analysis of exosomal PD-L1 by CD63-coated beads (left panel). Secretion of PD-L1 protein on exosome surface by human melanoma cells as determined by flow cytometry (right panel). Percentage of beads with PD-L1$^+$ exosomes from a representative experiment is indicated. (FIG. 1H) Diagram of ELISA of exosomal PD-L1 using monoclonal antibodies against the extracellular domain of PD-L1 (left panel). PD-L1 on the surface of exosomes secreted by human melanoma cells as determined by ELISA (right panel). (FIG. 1I) Levels of PD-L1 on exosomes secreted by melanoma cells, with or without IFN-γ treatment, as measured by ELISA. (FIG. 1J) PD-1 binding assay using exosomes secreted by melanoma cells with or without IFN-γ treatment. (FIG. 1K) Western blot analysis showing an increase in the level of PD-L1 in exosomes secreted by IFN-γ-treated cells ("IFN") compared to the control cells ("C"). The same amounts of exosome proteins from IFN-γ-treated and control cells were loaded. (FIG. 1L) Immunofluorescence staining of intracellular PD-L1 and exosome marker CD63. (FIG. 1M) Western blotting showing intracellular accumulation of CD63 and PD-L1 (in WCL), and decreased exosomal secretion of CD63 and PD-L1 (in EXO) in melanoma cells with HRS knockdown. (FIG. 1N) Co-immunoprecipitation of PD-L1 and Hrs. Data represent mean±s.d. of three (FIG. 1C, 1I) or two (FIG. 1G, 1H, 1J) independent biological replicates. ***P<0.001 by unpaired t-test (FIG. 1I).

Figure 2A:
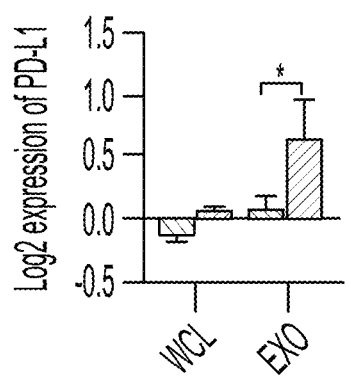
Figure 2B:
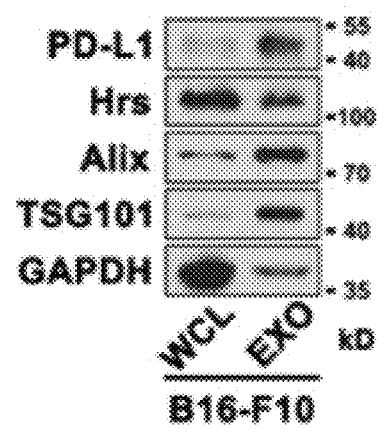
Figure 2C:
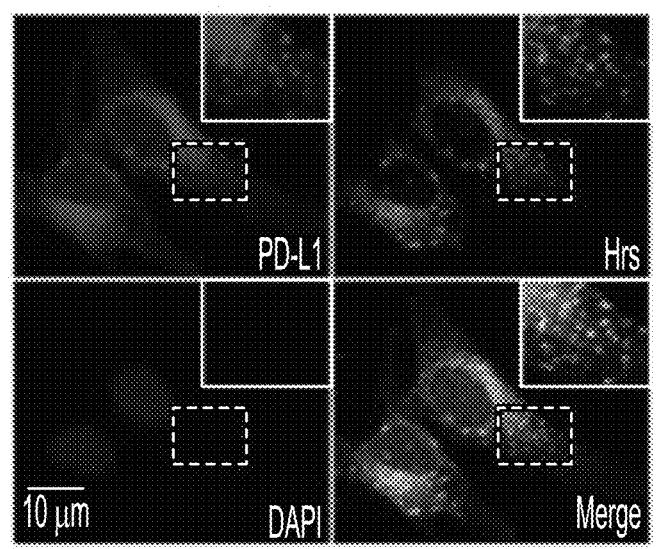
Figure 2D:
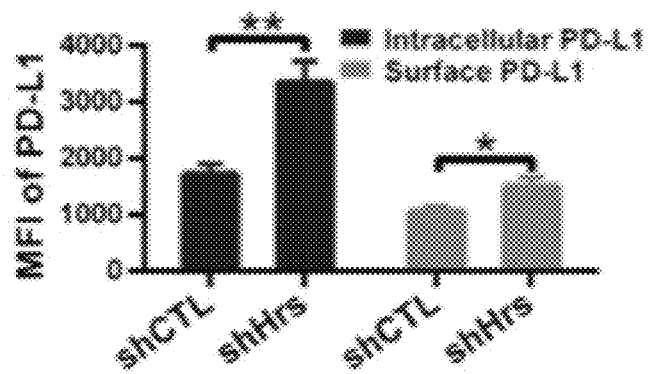
Figure 2E:
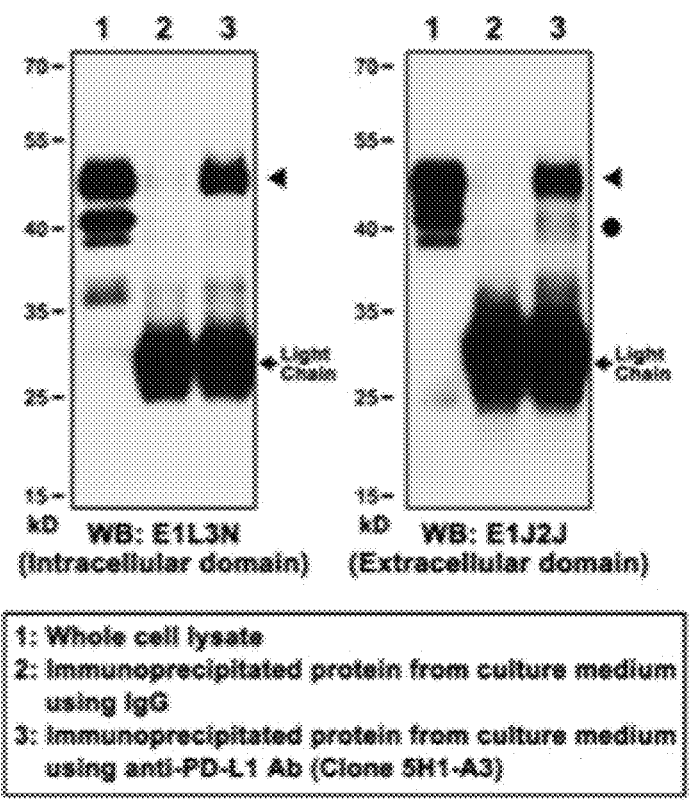

FIGS. 2A-2E. The secretion of exosomes carrying PD-L1 by melanoma cells. (FIG. 2A) The Log 2 transformed RPPA data showing a higher level of exosomal PD-L1 secreted by metastatic melanoma cell lines compared with primary melanoma cell lines. Data represent mean±s.d. of four primary (WM1552C, WM35, WM793, WM902B) or metastatic (UACC-903, 1205Lu, WM9, WM164) melanoma lines. (FIG. 2B) Immunoblots for PD-L1 in the whole cell lysate ("WCL") or in the purified exosomes ("EXO") from mouse melanoma B16-F10 cells. The same amounts of whole cell lysates and exosome proteins were loaded. Hrs, Alix, and TSG101 were used as exosome markers. (FIG. 2C) Immunofluorescence staining of intracellular PD-L1 and Hrs. (FIG. 2D) Flow cytometric analysis showing that knockdown of HRS led to an accumulation of PD-L1 in human melanoma WM9 cells. Data represent mean±s.d. of three independent biological replicates. (FIG. 2E) Immunoblots of PD-L1 proteins immunoprecipitated from the culture medium of IFN-γ-treated WM9 cells. Western blotting was performed using two different monoclonal antibodies targeting the intracellular domain (Clone E1L3N) and extracellular domain (Clone E1J2J) of PD-L1, respectively. In FIG. 2E, triangles indicate glycosylated full-length PD-L1; circles indicate PD-L1 containing only the extracellular domain. *P<0.05, **P<0.01 by unpaired t-test (FIG. 2A, 2D).

Figure 3A:
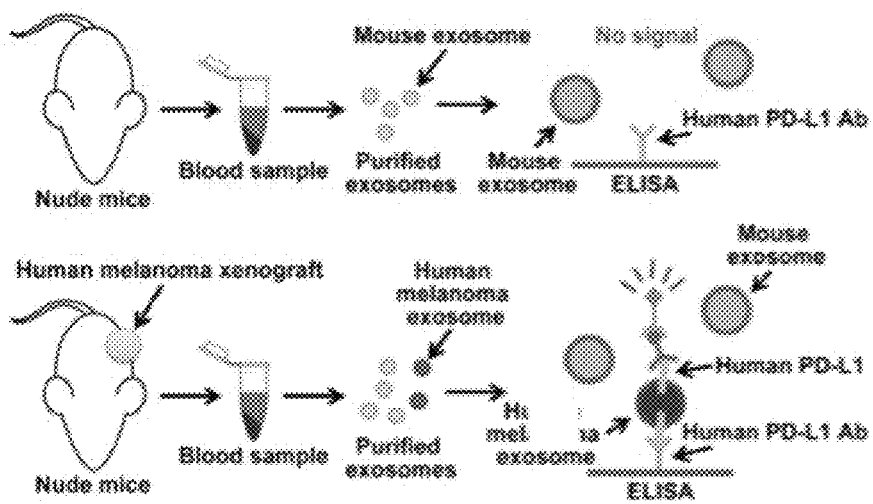
Figure 3B:
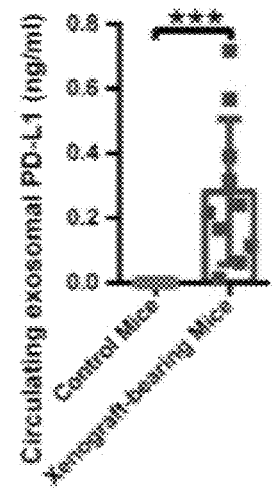
Figure 3C:
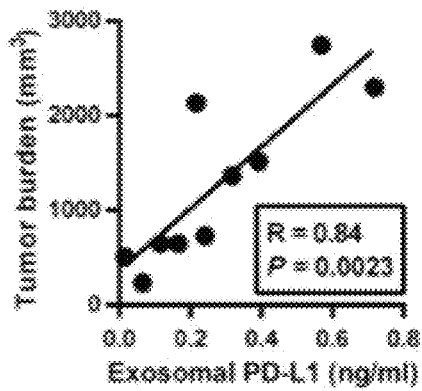
Figure 3D:
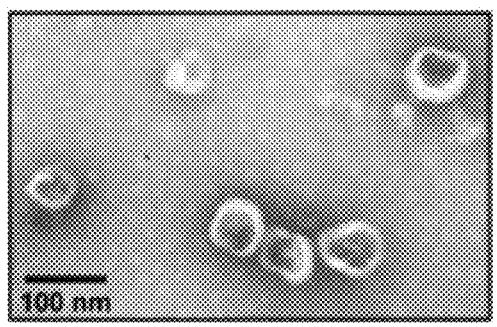
Figure 3E:
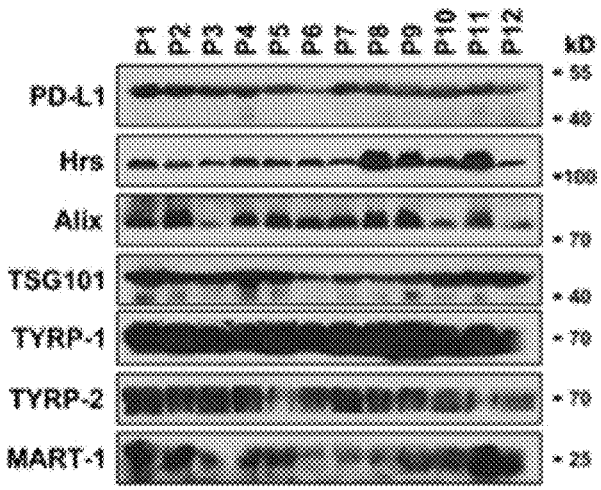
Figure 3F:
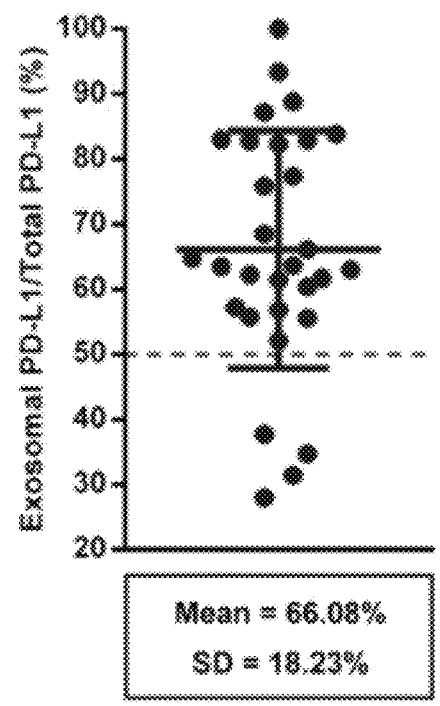
Figure 3G:
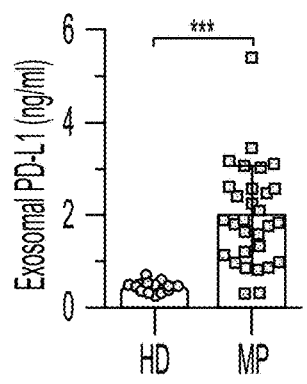
Figure 3H:
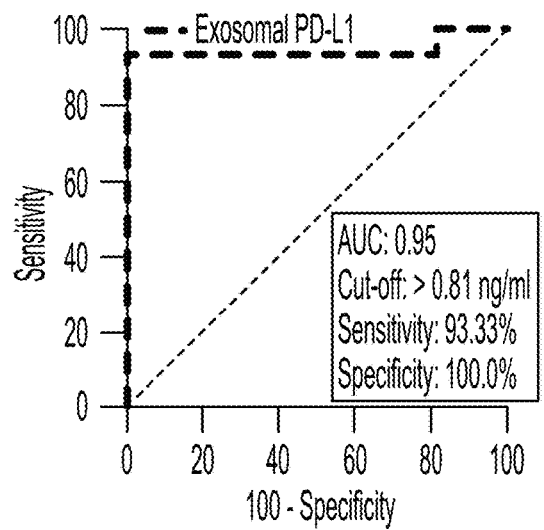
Figure 3I:
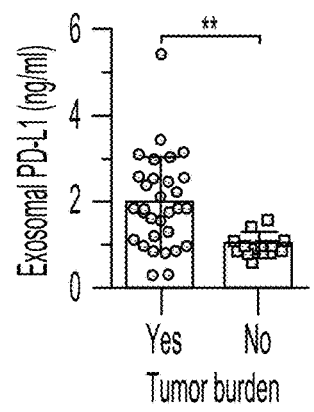

FIGS. 3A-3I. The majority of circulating PD-L1 proteins in patients with metastatic melanoma are carried on exosomes. (FIG. 3A) Diagram of ELISA of human melanoma cell-derived exosomal PD-L1 in the plasma samples derived from human melanoma xenograft-bearing or control mice using monoclonal antibodies that specifically recognize the extracellular domain of human PD-L1 protein. (FIG. 3B) Levels of PD-L1 on exosomes isolated from the plasma samples of control nude mice (n=10) or human melanoma xenograft-bearing nude mice (n=10) as measured by ELISA. (FIG. 3C) Pearson correlation between the plasma level of exosomal PD-L1 and tumor burden in xenograft-bearing nude mice. (FIG. 3D) A representative TEM image of circulating exosomes purified from the plasma sample of a patient with Stage IV melanoma. (FIG. 3E) Immunoblots for PD-L1 in the exosomes purified from the plasma samples of 12 patients with Stage IV melanoma (denoted as "P1" to "P12"). Exosome markers including Hrs, Alix, and TSG101, and melanoma-specific markers including TYRP-1, TYRP-2, and MART-1 were also tested. (FIG. 3F) Percentage of circulating PD-L1 in the exosomal fraction as calculated by dividing the level of exosomal PD-L1 by the level of total circulating PD-L1 detected in patient plasma. (FIG. 3G) ELISA showing the level of circulating exosomal PD-L1 in healthy donors (denoted as "HD", n=11) and melanoma patients (denoted as "MP", n=30). (FIG. 3H) ROC curve analysis for the level of circulating exosomal PD-L1 in patients with metastatic melanoma (n=30) compared to healthy donors (n=11). (FIG. 3I) ELISA showing the level of circulating exosomal PD-L1 in melanoma patients with (n=30) or without (n=11) measurable tumor burden. Data represent mean±s.d. P<0.01, *P<0.001 by unpaired t-test (FIG. 3B, 3G, 3I).

Figure 4A:
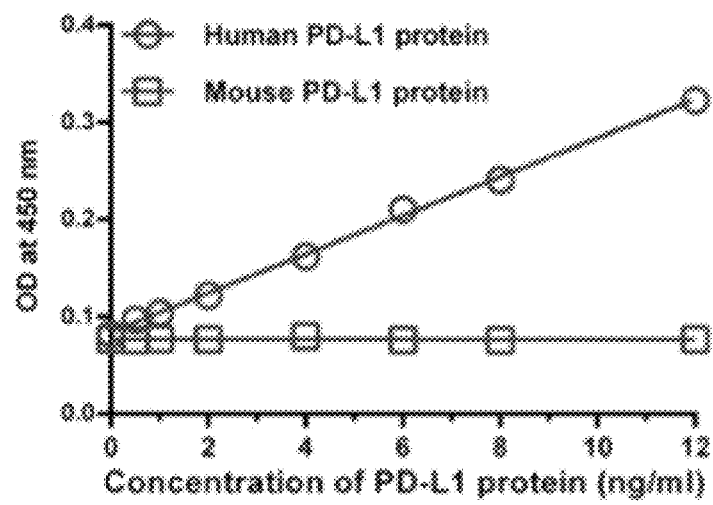
Figure 4B:
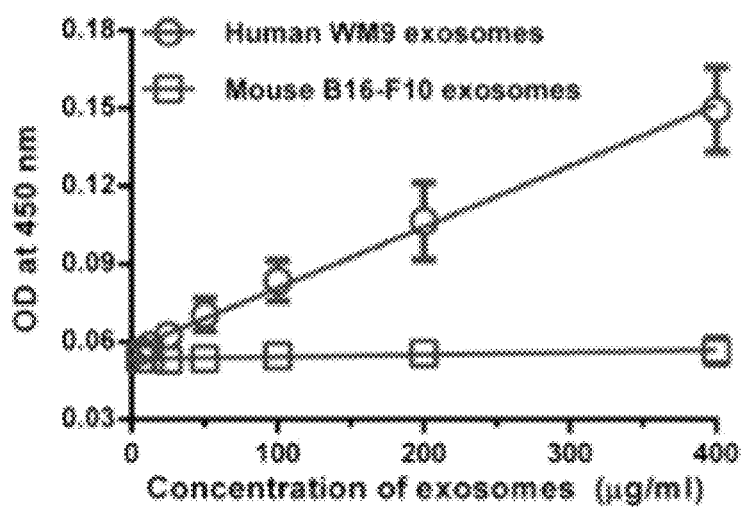
Figure 4C:
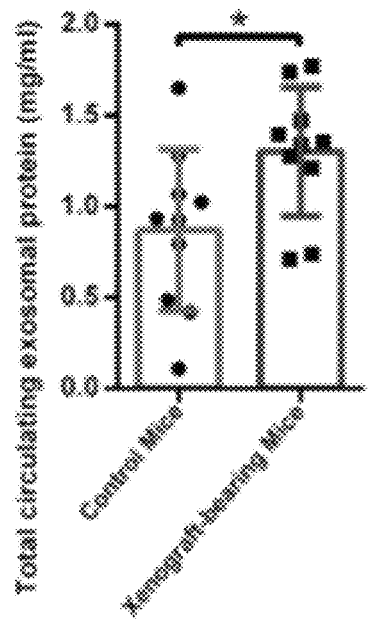
Figure 4D:
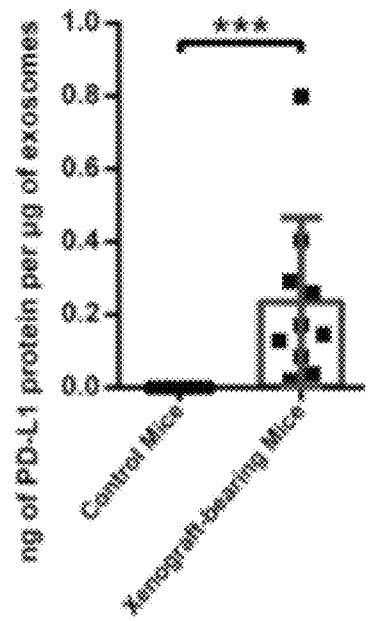

FIGS. 4A-4E. Melanoma cells secrete exosomal PD-L1 into the circulation. (FIG. 4A) The monoclonal antibodies against the extracellular domain of human PD-L1 protein specifically recognized recombinant human PD-L1 protein, but not recombinant mouse PD-L1 protein, as analyzed by ELISA. (FIG. 4B) The monoclonal antibodies against the extracellular domain of human PD-L1 specifically detect human exosomal PD-L1, but not mouse exosomal PD-L1. FIG. 4C) Levels of total exosomal protein isolated from the plasma samples of control nude mice (n=10) and human melanoma xenograft-bearing nude mice (n=10) as measured by Bradford protein assay. (FIG. 4D) Levels of circulating exosomal PD-L1 (ng) in plasma of control nude mice (n=10) and human melanoma xenograft-bearing nude mice (n=10) per μg of total circulating exosomal proteins. (FIG. 4E) Standard density gradient centrifugation analysis showing that circulating PD-L1 protein co-fractionated with exosome markers Hrs and TSG101 (typically between 1.13 to 1.19 g/ml) and melanoma-specific marker TYRP-2. Data represent mean±s.d. (FIG. 4B-4D). *P<0.05, ***P<0.001 by unpaired t-test (FIG. 4C-4D).

Figure 5A:
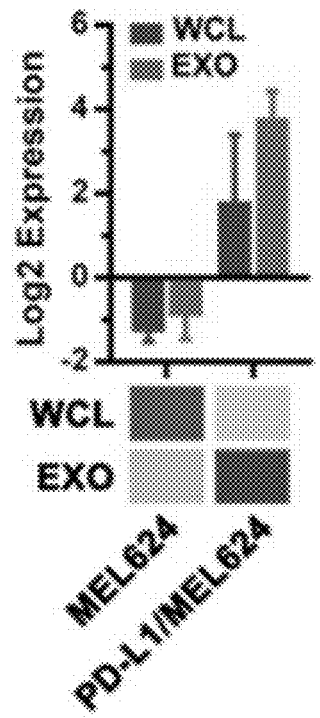
Figure 5B:
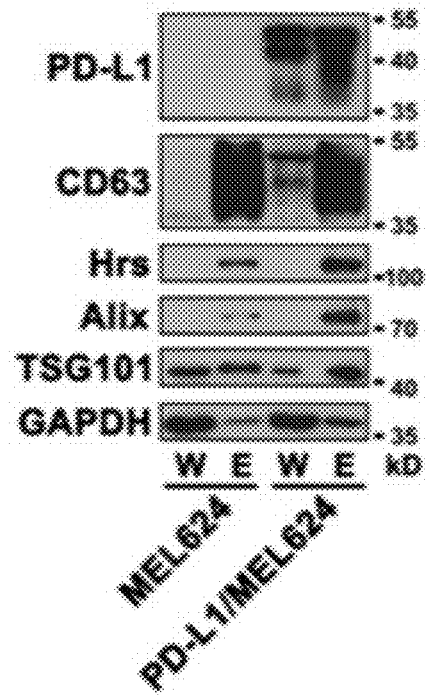
Figure 5C:
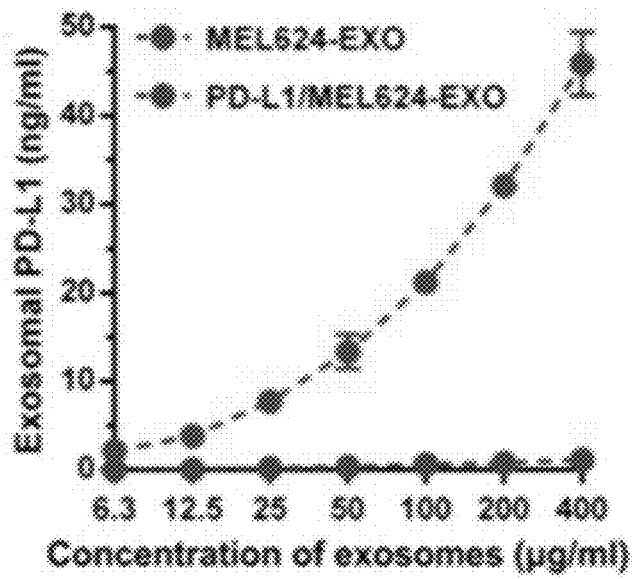
Figure 5D:
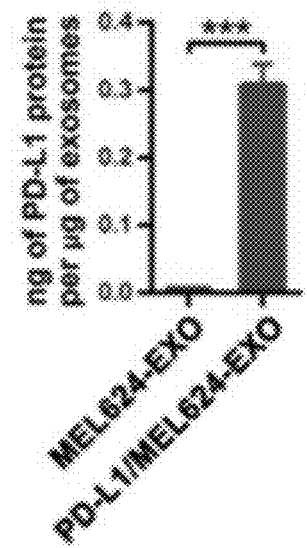

FIGS. 5A-5D. Characterization and quantification of exosomal PD-L1 secreted by MEL624 cells with or without PD-L1 expression. (FIG. 5A) Heatmap of RPPA data showing the levels of PD-L1 in the exosomes secreted by control (MEL624) or PD-L1-expressing (PD-L1/MEL624) human melanoma MEL624 cells. The Log 2 transformed data is shown at the top. (FIG. 5B) Immunoblots for PD-L1 in the whole cell lysate ("W") or in the purified exosomes ("E") from MEL624 or PD-L1/MEL624 cells. The same amounts of whole cell lysates and exosomal proteins for each cell line were loaded. CD63, Hrs, Alix, and TSG101 were used as exosome markers. GAPDH was used as the loading control. (FIG. 5C) PD-L1 on the surface of exosomes secreted by MEL624 or PD-L1/MEL624 cells as determined by ELISA. (FIG. 5D) Levels of PD-L1 on exosomes secreted by MEL624 or PD-L1/MEL624 cells, as measured by ELISA. Data represent mean±s.d. of three (FIG. 5A, 5D) or two (FIG. 5C) independent biological replicates. ***P<0.001 by unpaired t-test (FIG. 5D).

FIGS. 6A-6L. Exosomal PD-L1 inhibits CD8 T cells and facilitates the progression of melanoma in vitro and in vivo. (FIG. 6A) Representative contour plots of human peripheral CD8 T cells examined for the expression of Ki-67 and GzmB after treatment with MEL624 cell-derived exosomes or PD-L1/MEL624 cell-derived exosomes with or without blocking by IgG isotype or PD-L1 antibodies (left). The percentage of Ki-67±GzmB$^+$ CD8 T cells stimulated with anti-CD3/CD28 antibodies is shown at the right panel. (FIG. 6B-6C) Representative contour plots of human peripheral PD-1$^+$ or PD-1$^-$ CD8 T cells (stimulated with anti-CD3/CD28 antibodies) examined for the expression of Ki-67 and GzmB after treatment with melanoma WM9 cell-derived exosomes with or without blocking by IgG isotype or PD-L1 antibodies (FIG. 6B), and the percentage of PD-1+ or PD-1− CD8 T cells that are Ki-67±GzmB+ (FIG. 6C). (FIG. 6D) Representative histogram of human peripheral PD-1+ CD8 T cells (stimulated with anti-CD3/CD28 antibodies) stained with Annexin V after treatment with WM9 cell-derived exosomes with or without blocking by IgG isotype or PD-L1 antibodies (left). The proportion of Annexin V+ cells is shown at the right panel. (FIG. 6E-6F) CD8 T cell-meditated tumor cell killing assay was performed in MEL624 cells. Anti-CD3/CD28-stimulated CD8 T cells after treatment with PBS (Control), MEL624 cell-derived exosomes, or PD-L1/MEL624 cell-derived exosomes with or without blocking by IgG isotype or PD-L1 antibodies were co-cultured with MEL624 cells for 96 hr. The surviving tumor cells were visualized by crystal violet staining (FIG. 6E) and the relative survival of tumor cells (co-cultured with stimulated CD8 T cells) were calculated (FIG. 6F). (FIG. 6G) Volumes of B16-F10 PD-L1 knockdown tumors in mice treated with B16-F10 cell-derived exosomes with or without blocking by IgG isotype or PD-L1 antibodies were assessed every 2-3 days post cell inoculation (n=6 for each group). (FIG. 6H-6I) Survival of tumor-bearing mice after treatment with B16-F10 cell-derived exosomes with or without blocking by IgG isotype or PD-L1 antibodies (n=6 for each group). The overall log-rank P value is shown (FIG. 6H) and Wilcoxon test was used for two-way comparisons (FIG. 6I). (FIG. 6J) Representative immunofluorescence staining images of CD8 TILs in tumor tissues. (FIG. 6K) Numbers of CD8 TILs in B16-F10 PD-L1 knockdown tumors as determined by immunofluorescence staining. Shown are the cell numbers (mean±s.d.) quantified from 10 high-power fields (HPF). (FIG. 6L) Representative contour plot of CD8 TILs or splenic CD8 T cells examined for the expression of Ki-67 after treatment with B16-F10 cell-derived exosomes with or without blocking by IgG isotype or PD-L1 antibodies (top). The proportion of total and PD-1+ CD8 TILs or splenic CD8 T cells that are Ki-67+ is shown at the bottom (n=4-6 for each group). Data represent mean±s.d. of two (FIG. 6A, 6C) or three (FIG. 6D, 6F) independent biological replicates. *P<0.05, P<0.01, *P<0.001 by unpaired t-test (FIG. 6A, 6C, 6D, 6F, 6K, 6L) or two-way ANOVA (FIG. 6L). "NS", not significant.

FIGS. 7A-7C. Functional inhibition of CD8 T cells by exosomal PD-L1. (FIG. 7A) Representative contour plots of human peripheral CD8 T cells examined for the expression of Ki-67 and GzmB after treatment with human melanoma WM9 cell-derived exosomes (left). The percentage of Ki-67+ GzmB+ CD8 T cells (stimulated with anti-CD3/CD28 antibodies) is shown at the right panel. (FIG. 7B) Representative contour plots of human peripheral PD-1+ or PD-1− CD8 T cells (stimulated with anti-CD3/CD28 antibodies) examined for the expression of Ki-67 and GzmB after treatment with WM9 cell-derived exosomes in the presence or absence of anti-PD-1 blocking antibodies (left). The percentage of PD-1+ or PD-1− CD8 T cells that are Ki-67+ GzmB+ is shown to the right. (FIG. 7C) CD8 T cell-meditated tumor cell killing was assayed in MEL624 cells. Anti-CD3/CD28-stimulated CD8 T cells after treatment with PBS (Control) or WM9 cell-derived exosomes with or without blocking by IgG isotype or PD-L1 antibodies were co-cultured with MEL624 cells for 96 hr. The surviving tumor cells were visualized by crystal violet staining. The relative survival of tumor cells (co-cultured with stimulated CD8 T cells) were shown at the left bottom panel. Data represent mean±s.d. of two (FIG. 7A) or three (FIG. 7B, 7C) independent biological replicates. *P<0.05, P<0.01, *P<0.001 by unpaired t-test (FIG. 7A-7C).

Figure 8A:
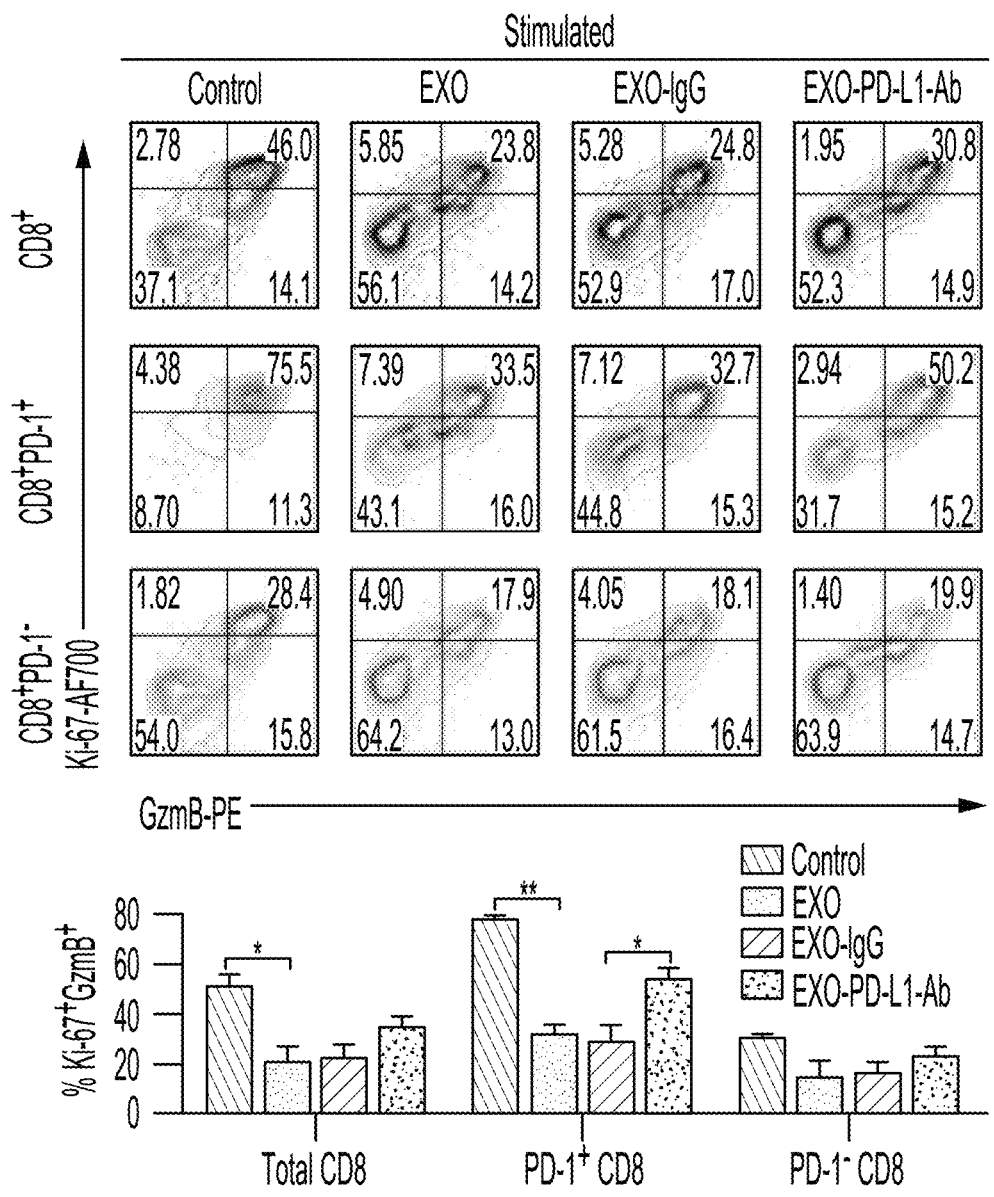
Figure 8B:
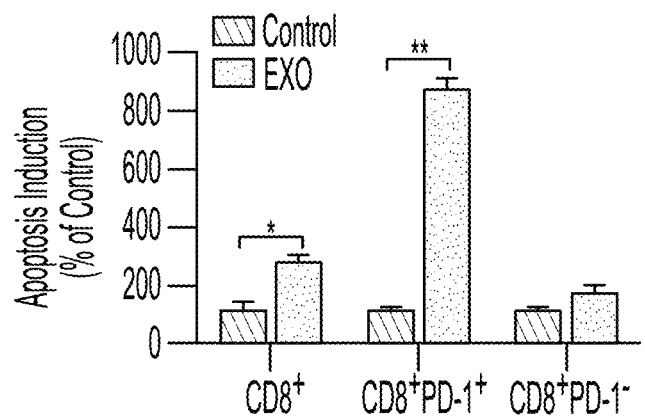
Figure 8C:
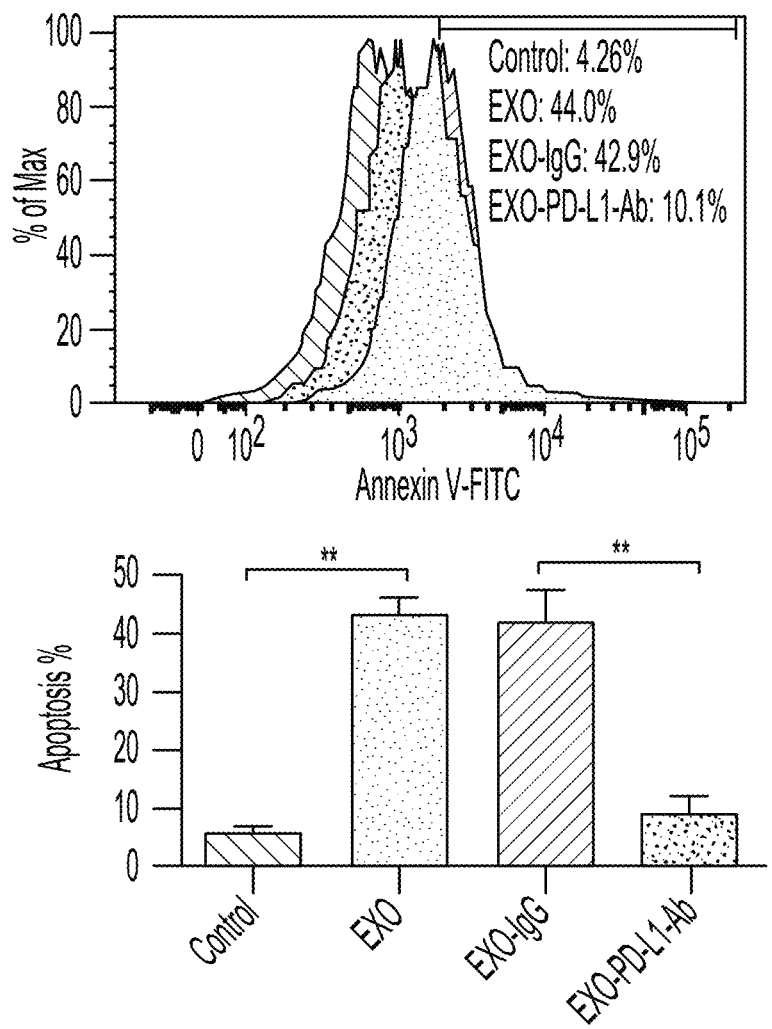

FIGS. 8A-8C. Exosomal PD-L1 secreted by mouse melanoma B16-F10 cells leads to the inhibition and apoptosis of mouse splenic CD8 T cells. (FIG. 8A) Representative contour plots of mouse splenic total, PD-1+ or PD-1− CD8 T cells (stimulated with anti-CD3/CD28 antibodies) examined for the expression of Ki-67 and GzmB after treatment with B16-F10 cell-derived exosomes with or without blocking by IgG isotype or PD-L1 antibodies (top). The percentage of total, PD-1+ or PD-1− CD8 T cells that are Ki-67+ GzmB+ is shown at the bottom. (FIG. 8B) Apoptosis of mouse splenic total, PD-1+ or PD-1− CD8 T cells induced by B16-F10 cell-derived exosomes. (FIG. 8C) Representative histogram of mouse splenic PD-1+ CD8 T cells stained with Annexin V after treatment with B16-F10 cell-derived exosomes with or without blocking by IgG isotype or PD-L1 antibodies (top). The percentage of Annexin V+ cells is shown at the bottom. Data represent mean±s.d. of two (FIG. 8A) or three (FIG. 8B, 8C) independent biological replicates. *P<0.05, **P<0.01 by unpaired t-test (FIG. 8A-8C).

FIGS. 9A-9E. Exosomal PD-L1 decreases T-lymphocyte infiltration and promotes melanoma growth in vivo. (FIG. 9A) Representative flow cytometric histograms of B16-F10 cells examined for the expression of PD-L1 with or without PD-L1 knockdown. B16-F10 cells were stably depleted of PD-L1 using lentiviral shRNA against PD-L1 ("shPD-L1") or the scrambled control shRNA ("shCTL"). (FIG. 9B) Immunoblots for PD-L1 in the whole cell lysate ("WCL") or in the purified exosomes ("EXO") from control ("shCTL") or PD-L1 knockdown ("shPD-L1") B16-F10 cells. (FIG. 9C) The volume of PD-L1 knockdown ("shPD-L1") or control ("shCTL") B16-F10 tumors at Day 23 post cell inoculation (n=6 for each group). Data represent mean±s.d. **P<0.01 by unpaired t-test. (FIG. 9D) Survival of mice bearing PD-L1 knockdown ("shPD-L1") or control ("shCTL") B16-F10 tumors (n=6 for each group). Shown is the overall log-rank P value. (FIG. 9E) Representative images showing the growth of PD-L1 knockdown B16-F10 tumors in C57BL/6 mice after treatment with B16-F10 cell-derived exosomes with or without blocking by IgG isotype or PD-L1 antibodies.

Figure 10A:
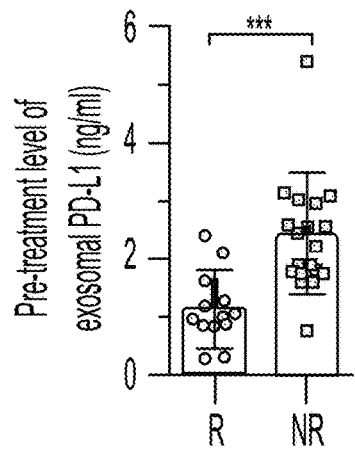
Figure 10B:
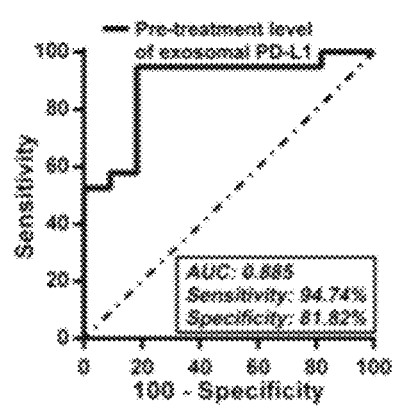
Figure 10C:
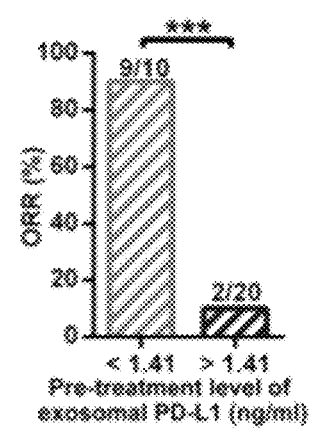

FIGS. 10A-10L. The level of circulating exosomal PD-L1 stratifies clinical responders from non-responders to pembrolizumab. (FIG. 10A) Comparison of the pre-treatment levels of circulating exosomal PD-L1 between melanoma patients with and without clinical response to pembrolizumab. "R": responders, n=11; "NR": non-responders, n=19. (FIG. 10B) ROC curve analysis for the pre-treatment level of circulating exosomal PD-L1 in clinical responders compared to non-responders. (FIG. 10C) Objective response rate ("ORR") for patients with high and low pre-treatment levels of circulating exosomal PD-L1. (FIG. 10D) Pearson correlation of IFN-γ level to the exosomal PD-L1 level in the plasma of melanoma patients (n=30). (FIG. 10E) The levels of circulating exosomal PD-L1 at serial time points pre- and on-treatment (n=23). (FIG. 10F) The levels of circulating exosomal PD-L1 in clinical responders (n=10) and non-responders (n=13) at serial time points pre- and on-treatment. (FIG. 10G) The frequency of PD-1+ Ki-67+ CD8 T cells and the level of circulating exosomal PD-L1 in clinical responders at serial time points pre- and on-treatment. (FIG. 10H) Pearson correlation of the circulating exosomal PD-L1 level at Week 6 to the frequency of PD-1+ Ki-67+ CD8 T cells at Week 3 in clinical responders and non-responders. (FIG. 10I) Pearson correlation of the fold change of circulating exosomal PD-L1 level at Week 6 to the fold change of PD-1+ Ki-67+ CD8 T cells at Week 3 in clinical responders and non-responders. (FIG. 10J) Comparison of the fold change of circulating exosomal PD-L1 at Week 6 between the clinical responders and non-responders. (FIG. 10K) ROC curve analysis for the fold change of circulating exosomal PD-L1 at Week 6 in clinical responders compared to non-responders. (FIG. 10L) Objective response rate for patients with high and low fold changes of circulating exosomal PD-L1 6 weeks. Data represent mean±s.d. *P<0.05, P<0.01, *P<0.001 by unpaired t-test (FIG. 10A, 10J), paired t-test (FIG. 10E, 10F), or Fisher's exact test (FIG. 10C, 10L). "NS", not significant.

Figure 11:
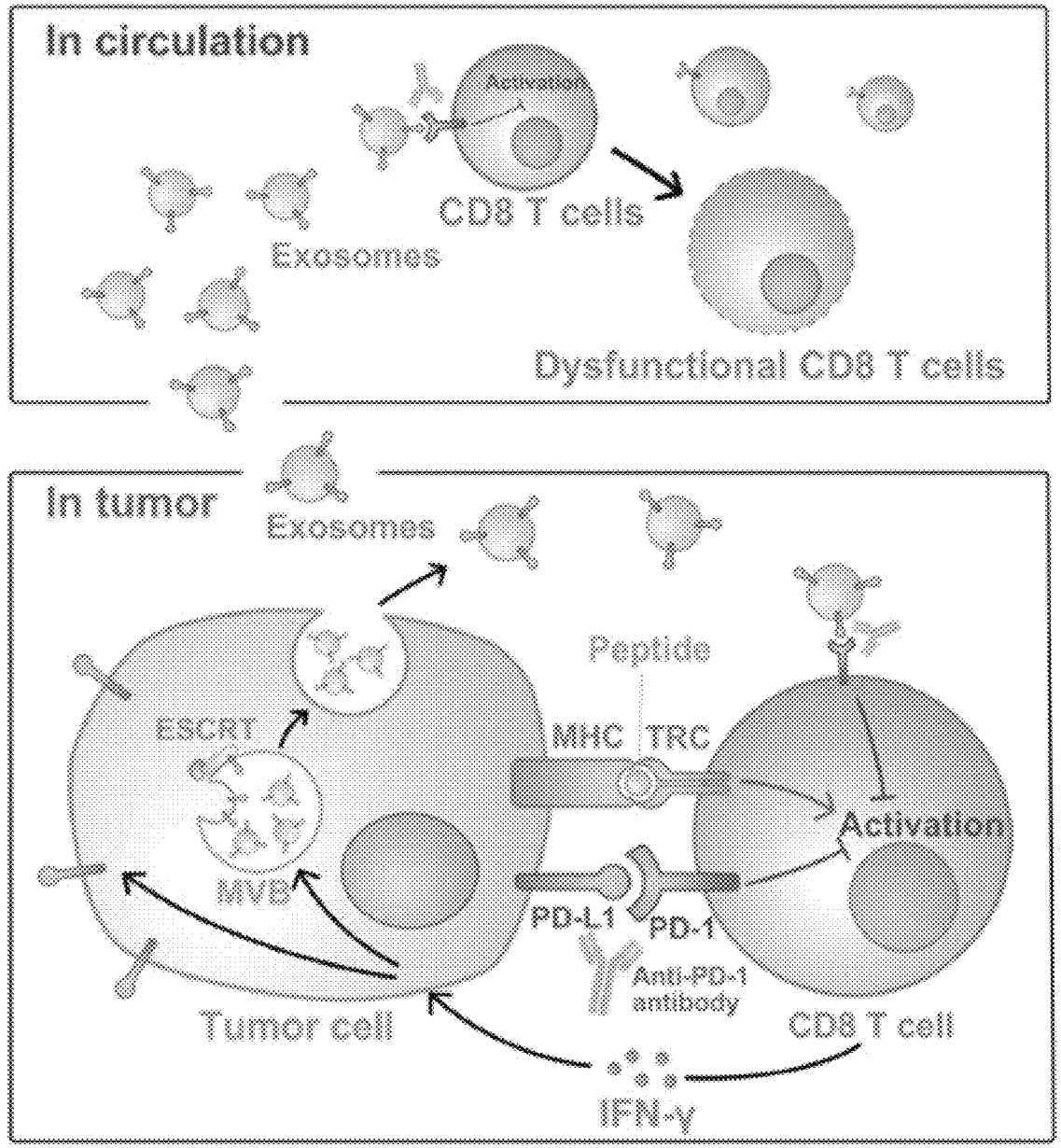

FIG. 11. Model for exosomal PD-L1-mediated immunosuppression. In addition to the direct tumor cell-T cell interaction, melanoma cells secrete a large number of exosomes carrying PD-L1 proteins on their surface, which interact with T cells in the tumor microenvironment and in the circulation to suppress the immune system systemically. IFN-γ further up-regulates exosomal PD-L1, serving as a more effective mechanism for the tumor cells to adapt to the immune system. The exosomal PD-L1-T cell interaction can be blocked by anti-PD-1 or anti-PD-L1 antibodies, suggesting that disruption of the interaction between the exosomal PD-L1 and T cell PD-1 is involved in the current PD-L1/PD-1 blockade-based therapies.

Figure 12A:
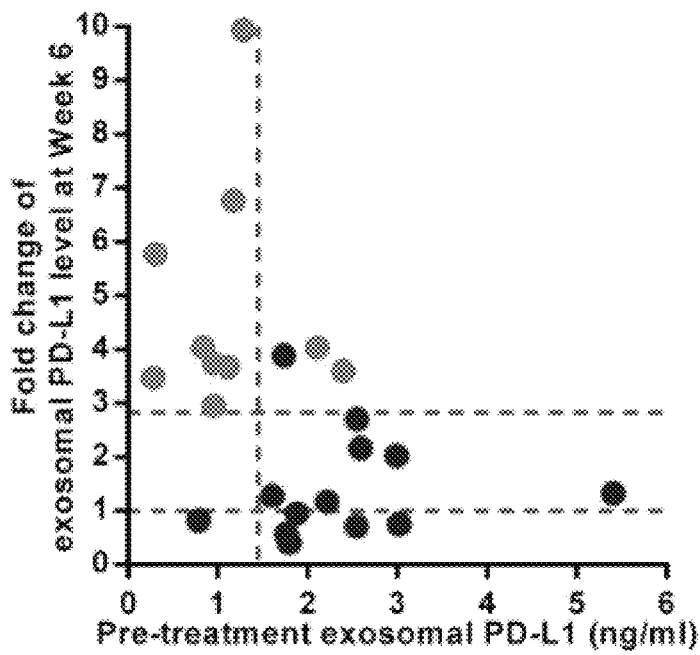
Figure 12B:
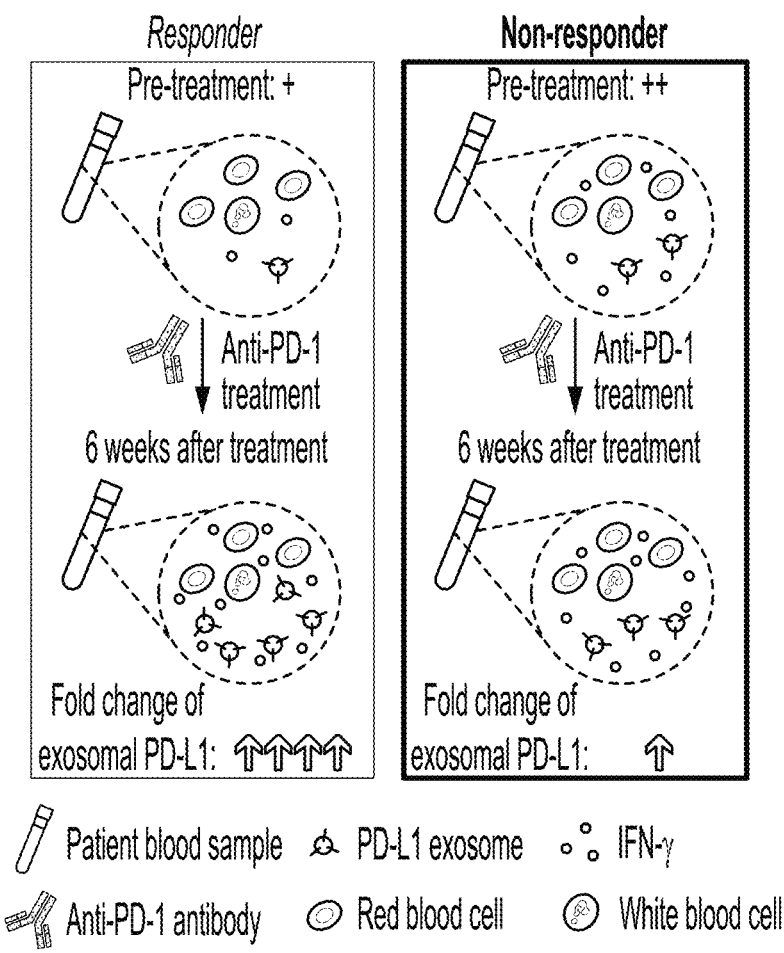
Figure 12C:
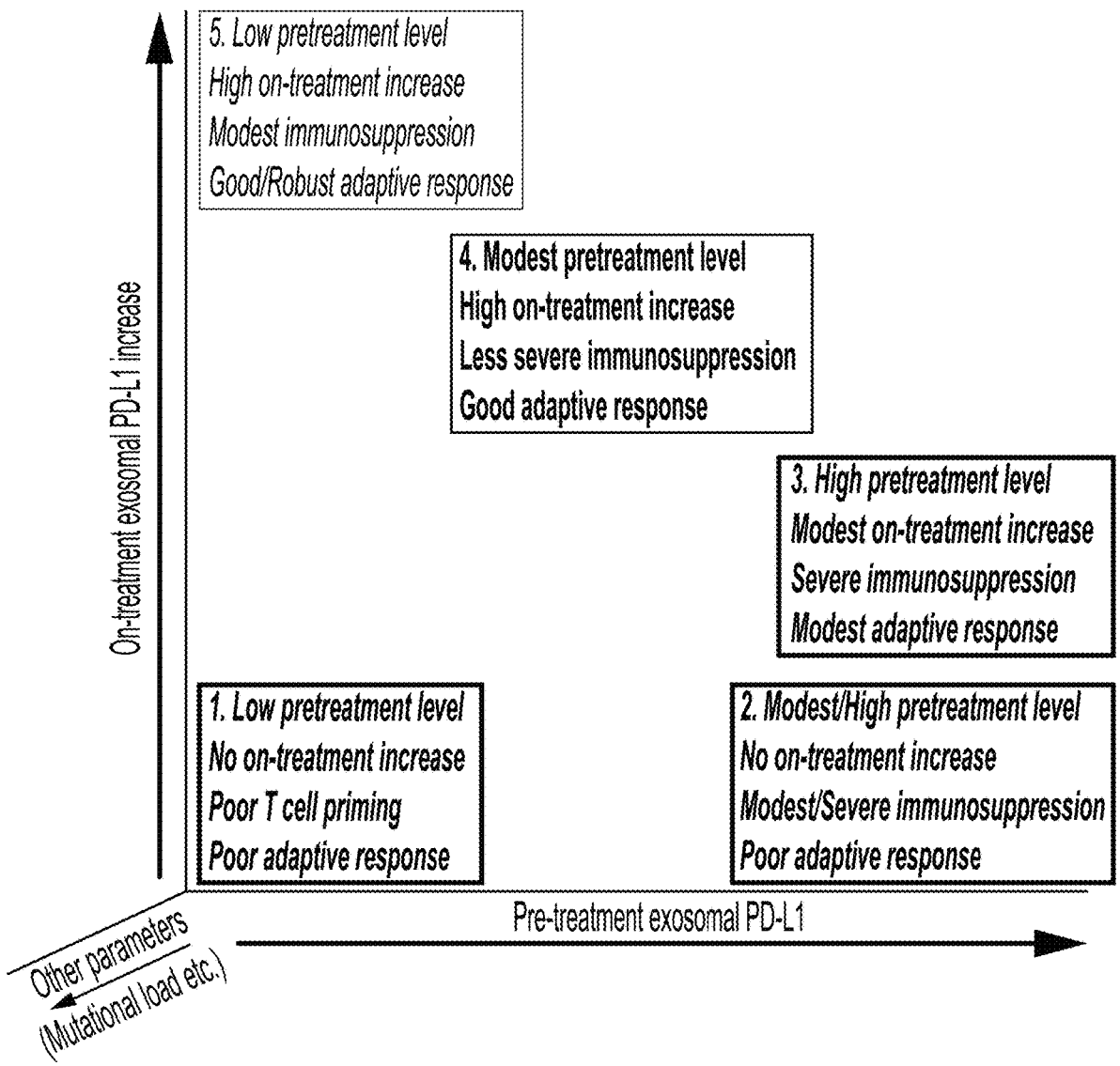

FIGS. 12A-12C. Circulating exosomal PD-L1 is a rationale-based and clinically accessible predictor for clinical outcomes of anti-PD-1 therapy. (FIG. 12A) Tracking the levels of circulating exosomal PD-L1 before and during anti-PD-1 treatment can be used to stratify responders (green) from non-responders (red) to anti-PD-1 therapy as early as 6 weeks into the treatment. (FIG. 12B) Diagram for the application of circulating exosomal PD-L1 to predict patients' response to anti-PD-1 therapy. The pre-treatment level of circulating exosomal PD-L1 is lower in metastatic melanoma patients with clinical response to anti-PD-1 therapy. After 6 weeks of anti-PD-1 treatment, the level of circulating exosomal PD-L1 increases significantly in clinical responders but not in non-responders. (FIG. 12C) Tracking both the pre-treatment and on-treatment levels of circulating exosomal PD-L1 provides guidance for determining the success (green) or failure (red) of the therapy.

Figure 13A:
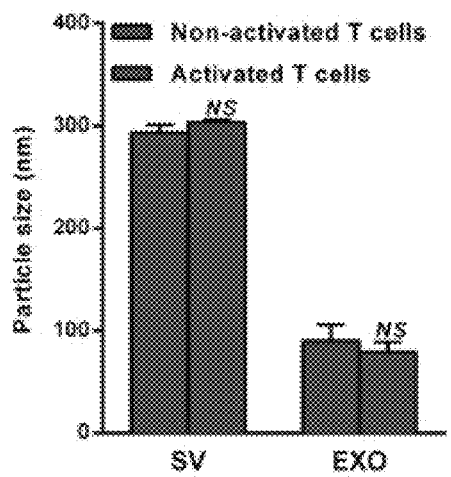
Figure 13B:
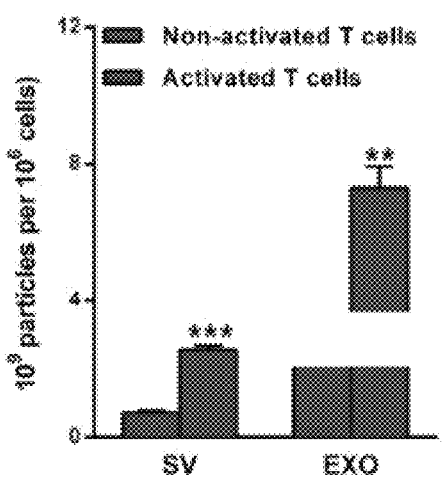
Figure 13C:
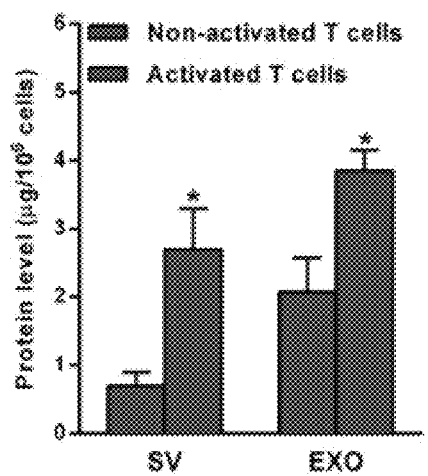
Figure 13D:
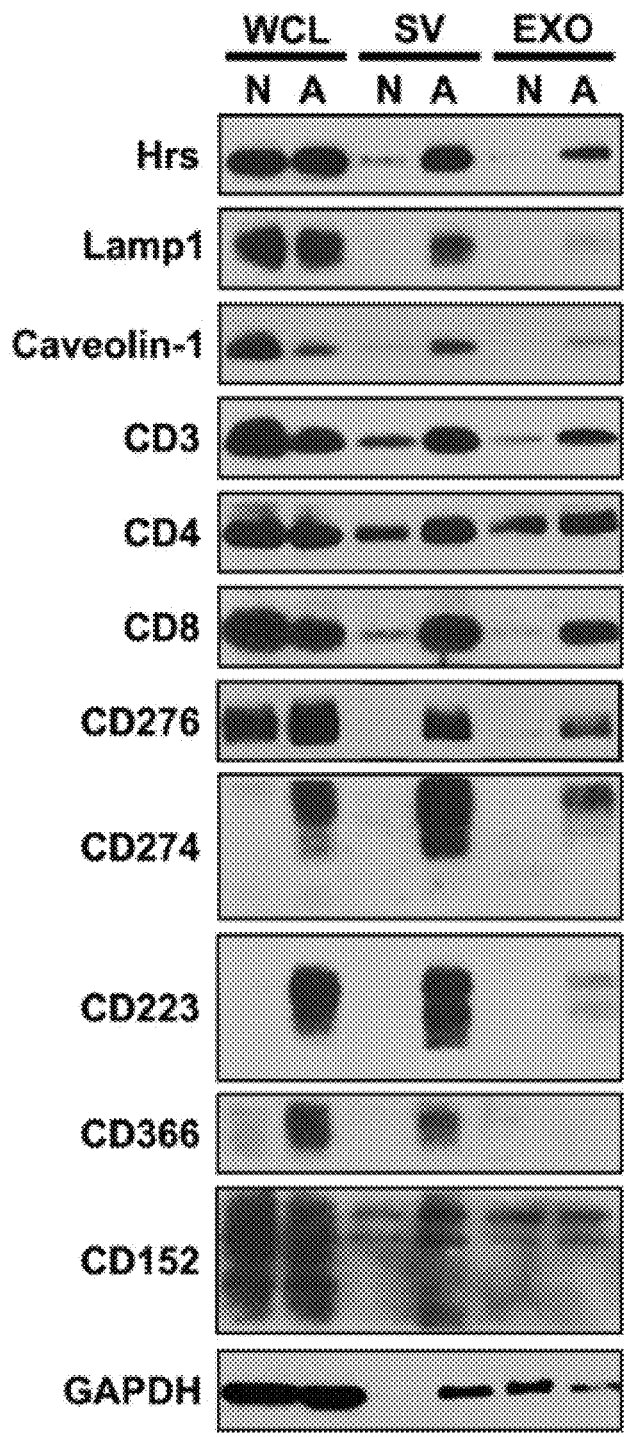

FIG. 13A-13D. Purification and characterization of T cell-derived shedding vesicles and exosomes. (FIG. 13A) Size distribution of the shedding vesicles and exosomes secreted by activated and non-activated T cells as determined by the NanoSight nanoparticle tracking analysis (NTA) technology. "SV": shedding vesicles; "EXO": exosomes. (FIG. 13B). Quantification of the shedding vesicles and exosomes secreted by activated and non-activated T cells using NanoSight nanoparticle tracking analysis (NTA) technology. (FIG. 13C). Measurement of the total protein level of the shedding vesicles and exosomes secreted by activated and non-activated T cells using Bio-Rad Bradford protein assay. (FIG. 13D). Purified shedding vesicles and exosomes from activated and non-activated T cells were analyzed by immunoblotting for the presence of exosome markers, T cell markers, and immunomodulator proteins.

DETAILED DESCRIPTION OF THE INVENTION

PD-L1 on tumor cells interacts with PD-1 on lymphocytes to elicit the immune checkpoint response bookmark0. Here we report that metastatic melanoma cells also secrete a high level of exosomes that carry PD-L1 (henceforth termed "PD-L1 exosomes") on their surface.

We report that secretion of exosomal PD-L1 proteins is regulated by the components of the Endosomal Sorting Complex Required for Transport (ESCRT) machinery, and more especially, by the endosomal protein Alix. Furthermore, interferon-γ (IFN-γ) up-regulates the level of PD-L1 on exosomes. The PD-L1 exosomes potently suppress the function of CD8 T cells, and facilitate tumor growth in vitro and in vivo.

In patients with metastatic melanoma, the level of circulating exosomal PD-L1 is positively associated with the level of IFN-γ. Moreover, both pre-treatment and on-treatment levels of circulating exosomal PD-L1 strongly correlate with the clinical response to anti-PD-1 therapy. Consequently, the pattern of change in circulating exosomal PD-L1 stratifies clinical responders and non-responders, thereby providing a reliable predictor of response to anti cancer therapy.

Identification and characterization of exosomal PD-L1 proteins provides a novel molecular mechanism by which melanoma cells systemically interact with and combat the immune system. This identification of the immunosuppressive role for exosomal PD-L1 facilitates the development of PD-L1/PD-1 blockade therapies and provides a new biomarker for tracking progression of this deadly cancer.

The following definitions are provided to facilitate an understanding of the present invention.

I. Definitions

For purposes of the present invention, "a" or "an" entity refers to one or more of that entity; for example, "an antibody" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the functional and novel characteristics of the sequence.

The terms "exosome" and "extracellular vesicle", are used interchangeably herein to describe membrane vesicles of endosomal and plasma membrane origin which are released from many different cell types. These extracellular vesicles (EVs) represent an important mode of intercellular communication by serving as vehicles for transfer between cells of membrane and cytosolic proteins, lipids, and RNA. Extracellular vesicles or exosomes are released from cells upon fusion of an intermediate endocytic compartment, the multivesicular body (MVB), with the plasma membrane. This liberates intraluminal vesicles (ILVs) into the extracellular milieu and the vesicles thereby releasing exosomes. There are other types of microvesicle, including apoptotic bodies and ectosomes, which are derived from cells undergoing apoptosis and plasma membrane shedding, respectively. Although apoptotic bodies, ectosomes and exosomes are all roughly the same size (typically 40-100 nm) and all also contain 'gulps' of cytosol, they are different species of vesicles.

A "biomarker" or "sensitivity marker" is a marker that is associated with differential sensitivity or response to a treatment, for example a treatment that includes anti-PD-1 and/or anti-PD-L1 therapy. Such markers may include, but are not limited to, nucleic acids, proteins encoded thereby, or other small molecules. These markers can be used to advantage to identify those patients likely to respond to therapy from those that are unlikely to respond. They can also be targeted to modulate the response to therapy or used in screening assays to identify agents that have efficacy or act synergistically for the treatment and management of melanoma or other cancers.

Detection of biomarkers can be carried out by standard histological and/or immuno-detection methods. In particular embodiments, the markers can be detected by any means of polypeptide detection, or detection of the expression level of the polypeptides. For example, the polypeptide can be detected using any of antibody detection methods (e.g., immunofluorescent (IF) methods, flow cytometry, fluorescence activated cell sorting (FACS)), antigen retrieval and/or microarray detection methods can be used. A reagent that specifically binds to a marker polypeptide, e.g., an antibody, and antibody derivative, and an antibody fragment, can be used. Other detection techniques that can be used include, e.g., capture assays (e.g., ELISA), mass spectrometry (e.g., LCMS/MS), and/or polymerase chain reaction (e.g., RT-PCR). Biomarkers can also be detected by systemic administration of a labeled form of an antibody to the biomarker, followed by imaging.

In yet another approach, the method of detection of exosomal PD-L1 protein includes a fluorescent or quantum dot labeled antibody, such as labeled anti-PDL1 for labeling proteins on the surface of exosomes. After labeling the exosomal proteins, light scattering-based nanoparticle tracking analysis (NTA) employing a NanoSight NS300 Analyzer can be utilized to monitor individual vesicles as small as 10 nM. This combination of protein labeling and size measurement provides the unique ability to visualize exosomal proteins in suspension and directly observe their Brownian motion, yielding rapid, accurate, high-resolution sizing data by number distribution, as well as count and concentration measurements with visual confirmation of data analysis.

In another embodiment, a nucleic acid sample from the subject is evaluated by a nucleic acid detection technique as described herein.

In other embodiments, biomarkers are measured or detected by measuring mRNA expression. Numerous techniques such as qRT-PCR, Fluidigm, RNAseq (e.g. Illumina), Affymetrix gene profiling, the NanoString nCounter platform, or Nanopore sequencing (Oxford Nanopore Technologies) may be used by the person skilled in the art using their common general knowledge to measure RNA levels.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

"Target nucleic acid" as used herein refers to a previously defined region of a nucleic acid present in a complex nucleic acid mixture wherein the defined wild-type region contains at least one known nucleotide variation which may or may not be associated with disease. The nucleic acid molecule may be isolated from a natural source by cDNA cloning or subtractive hybridization or synthesized manually. The nucleic acid molecule may be synthesized manually by the triester synthetic method or by using an automated DNA synthesizer.

Regarding nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form. By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately 10-6-fold purification of the native message. Thus, purification of at least one order of magnitude, preferably two or three orders, and more preferably four or five orders of magnitude is expressly contemplated. Thus, the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

"PD-L1" may refer to human PD-L1 or homologs in other organisms, depending on the context in which it is used. Human PD-L1 is also known as CD274, B7-H, B7H1, B7-H1, B7 homolog 1, MGC142294, MGC142296, PDCD1L1, PDCD1LG1, PDCD1 ligand 1, PDL1, Programmed cell death 1 ligand 1 and Programmed death ligand 1 and has Uniprot number Q9NZQ7 and NCBI gene ID number 29126. Human PD-L1 is a 290 amino acid type I transmembrane protein encoded by the CD274 gene on human chromosome 9. Mouse PD-L1 has NCBI GenBank ID number ADK70950.1.

A "cancer protein" is a protein which is associated with malignant transformation and progression. Such proteins may or may not contain mutations. Exemplary "cancer proteins" include, without limitation, BRAF, NRAS, KIT, TP53, PTEN, EGFR, HER2, ALK, AKT1, KRAS, MET, RET, RHOA, ARID1A, CDH1, Akt, Wnt5A, MAPK1, HSP70, TRAP1, HSP90, SerpinH1, VEGFC, R-RAS and HLA-G5.

An immunomodulator protein is a protein which plays a role in immune processes which regulate malignant transformation and progression. Such proteins, include for example, CD109, CD151, CD276, CD44, CD46, CD47, CD55, CD58, CD59, CD70, CD9, CD95, CD97, CD99, and B7H4.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus, if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

For instance, one common formula for calculating the stringency conditions required to achieve hybridization between nucleic acid molecules of a specified sequence homology is set forth below (Sambrook et al., Molecular Cloning, Cold Spring Harbor Laboratory (1989)):

$$Tm = 81.5° C. + 16.6 \ Log[Na+] + 0.41(\% \ G+C) - 0.63(\% \ formamide) - 600/\#bp \ \text{in duplex}$$

As an illustration of the above formula, using [Na+]=[0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated Tm of the hybrid. Wash conditions should be as stringent as possible for the degree of identity of the probe for the target. In general, wash conditions are selected to be approximately 12-20° C. below the Tm of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

Polymerase chain reaction (PCR) has been described in U.S. Pat. Nos. 4,683,195, 4,800,195, and 4,965,188, the entire disclosures of which are incorporated by reference herein.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single stranded or double stranded. The exact length of the probe will depend upon many factors, including temperature, source of probe and use of the method. For example, for diagnostic applications, depending on the complexity of the target sequence, the oligonucleotide probe typically contains 15 to 25, 30, 50, 75 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non complementary nucleotide fragment may be attached to the 5' or 3' end of the probe, with the remainder of the probe sequence being complementary to the target strand. Alternatively, non complementary bases or longer sequences can be interspersed into the probe, provided that the probe sequence has sufficient complementarity with the sequence of the target nucleic acid to anneal therewith specifically. The probe many also be labeled with a non-naturally occurring label to ease detection of the target.

The term "primer" as used herein refers to an oligonucleotide, either RNA or DNA, either single stranded or double stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15 to 25, 30, 50, 75 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complimentary bases may be interspersed within the oligonucleotide primer sequence, provided that the primer sequence has sufficient complementarity with the sequence of the desired template strand to functionally provide a template primer complex for the synthesis of the extension product.

A "label" or a "detectable moiety" in reference to a nucleic acid or protein, example, refers to a composition that, when linked with a nucleic acid or protein, renders the nucleic acid or protein detectable, for example, by spectroscopic, photochemical, biochemical, immunochemical, or chemical means. Exemplary labels include, but are not limited to, radioactive isotopes, magnetic beads, metallic beads, colloidal particles, fluorescent dyes, enzymes, biotin, digoxigenin, haptens, and the like. A "labeled nucleic acid or oligonucleotide probe" is generally one that is bound, either covalently, through a linker or a chemical bond, or noncovalently, through ionic bonds, van der Waals forces, electrostatic attractions, hydrophobic interactions, or hydrogen bonds, to a label such that the presence of the nucleic acid or probe can be detected by detecting the presence of the label bound to the nucleic acid or probe.

A "chemotherapeutic agent" or "anti-cancer agent" is a chemical compound useful in the treatment of cancer. Classes of chemotherapeutic agents include, but are not limited to: alkylating agents, antimetabolites, kinase inhibitors, spindle poison plant alkaloids, cytoxic/antitumor antibiotics, topoisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, RAF inhibitors, anti-sense oligonucleotides that that inhibit expression of genes implicated in abnormal cell proliferation or tumor growth. Chemotherapeutic agents useful in the treatment methods of the present invention can include agents that selectively inhibits one or more vital steps in signaling pathways, in the normal function of cancer cells, thereby leading to apoptosis. Signal transduction inhibitors (STIs) include, but are not limited to, (i) bcr/abl kinase inhibitors such as, for example, STI 571 (Gleevec); (ii) epidermal growth factor (EGF) receptor inhibitors such as, for example, kinase inhibitors (Iressa, SSI-774) and antibodies (Imclone: C225 [Goldstein et al. (1995), *Clin Cancer Res.* 1:1311-1318], and Abgenix: ABX-EGF); (iii) her-2/neu receptor inhibitors such as, for example, Herceptin™ (trastuzumab), and farnesyl transferase inhibitors (FTI) such as, for example, L-744,832 (Kohl et al. (1995), *Nat Med.* 1(8):792-797); (iv) inhibitors of Akt family kinases or the Akt pathway, such as, for example, rapamycin (see, for example, Sekulic et al. (2000) Cancer Res. 60:3504-3513); (v) cell cycle kinase inhibitors such as, for example, flavopiridol and UCN-01 (see, for example, Sausville (2003) Curr. Med. Chem. Anti-Canc Agents 3:47-56); and (vi) phosphatidyl inositol kinase inhibitors such as, for example, LY294002 (see, for example, Vlahos et al. (1994) J. Biol. Chem. 269:5241-5248). In a particular embodiment, the STI is selected from the group consisting of STI 571, SSI-774, C225, ABX-EGF, trastuzumab, L-744,832, rapamycin, LY294002, flavopiridal, and UNC-01. In yet another embodiment, the STI is L-744,832

Chemotherapeutic agents which function as alkylating agents include without limitation, nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). Preferably, the chemotheraputic agent is selected from the group consisting of: paclitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives. PD-1/PD-L1 directed therapies include without limitation pembrolizumab, nivolumab, atezolizumab, avelumab, durvalumab and other anti-PD1/PDL1 antibodies that are in development.

A "therapeutically effective amount" of a compound or a pharmaceutical composition refers to an amount effective to prevent, inhibit, or treat the symptoms of a particular disorder or disease. For example, "therapeutically effective amount" may refer to an amount sufficient to modulate tumor growth or metastasis in an animal, especially a human, including without limitation decreasing tumor growth or size or preventing formation of tumor growth in an animal lacking any tumor formation prior to administration, i.e., prophylactic administration.

"Pharmaceutically acceptable" indicates approval by a regulatory agency of the Federal or a state government or listed in the U.S. Pharmacopeia or other generally recognized pharmacopeia for use in animals, and more particularly in humans.

"Concurrently" means (1) simultaneously in time, or (2) at different times during the course of a common treatment schedule.

"Sequentially" refers to the administration of one component of the method followed by administration of the other component. After administration of one component, the next component can be administered substantially immediately after the first component, or the next component can be administered after an effective time period after the first component; the effective time period is the amount of time given for realization of maximum benefit from the administration of the first component.

A "specific binding pair" comprises a specific binding member (sbm) and a binding partner (bp) which have a particular specificity for each other (or "specifically bind") and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" or "specific binding" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

In general, the detection of immune complex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

"Sample" or "patient sample" or "biological sample" generally refers to a sample which may be tested for a particular molecule, preferably a sensitivity marker molecule. Samples may include but are not limited to cells, body fluids, including blood, bone marrow, serum, plasma, urine, saliva, tears, pleural fluid and the like.

A "diagnostic marker" is a specific biochemical in the body which has a particular molecular feature that makes it useful for detecting a disease, measuring the progress of disease or the effects of treatment, or for measuring a process of interest.

The term "subject" refers to both animals and humans.

The terms "decrease," "decreased," and "decreasing" or "increase," "increased," and "increasing" are intended to refer to a change in measurement of a parameter by at least 10%, 20%, 30%, 40%, 50%, 60%, 70%, 80%, 90%, 100%, 200% or more when compared to the measurement of that parameter in a suitable control.

The terms "inhibit," "inhibition," "inhibiting," "reduced," "reduction," and the like as used herein refer to any decrease in the expression or function of a target gene product, including any relative decrement in expression or function up to and including complete abrogation of expression or function of the target gene product.

An "antibody" or "antibody molecule" is any immunoglobulin, including antibodies and fragments thereof, that binds to a specific antigen. The term includes polyclonal, monoclonal, chimeric, single domain (Dab) and bispecific antibodies. As used herein, antibody or antibody molecule contemplates recombinantly generated intact immunoglobulin molecules and immunologically active portions of an immunoglobulin molecule such as, without limitation: Fab, Fab', F(ab')2, F(v), scFv, scFv2, scFv-Fc, minibody, diabody, tetrabody, single variable domain (e.g., variable heavy domain, variable light domain), bispecific, Affibody® molecules (Affibody, Bromma, Sweden), and peptabodies (Terskikh et al. (1997) PNAS 94:1663-1668).

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. The compositions can be incorporated into particulate preparations of polymeric compounds such as polylactic acid, polyglycolic acid, etc., or into liposomes or micelles. Such compositions may influence the physical state, stability, rate of in vivo release, and rate of in vivo clearance of components of a pharmaceutical composition of the present invention. The pharmaceutical composition of the present invention can be prepared, for example, in liquid form, or can be in dried powder form (e.g., lyophilized). Suitable pharmaceutical carriers are described in "Remington's Pharmaceutical Sciences" by E.W. Martin (Mack Publishing Co., Easton, PA); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "treat" as used herein refers to any type of treatment that imparts a benefit to a patient afflicted with a disease, including improvement in the condition of the patient (e.g., amelioration of one or more symptoms), delaying progression of disease, and/or curing the disease.

II. Therapies and Compositions for the Treatment of Cancer

The present invention provides pharmaceutical compositions comprising at least one anti-cancer agent, preferably an agent which specifically targets PD-1/PD-L1 in a pharmaceutically acceptable carrier. Such a pharmaceutical composition may be administered, in a therapeutically effective amount, to a patient in need thereof for the treatment of cancer. Agents which selectively target the PD-1/PD-L1 pathway are provided hereinabove.

The pharmaceutical composition may further comprise at least one signal transduction inhibitor (STI) (see, e.g., PCT/US04/05155 and PCT/US04/05154). Suitable STIs, as noted hereinabove, include, but are not limited to: (i) bcr/abl kinase inhibitors such as, for example, STI 571 (Gleevec); (ii) epidermal growth factor (EGF) receptor inhibitors such as, for example, kinase inhibitors (Iressa, SSI-774) and antibodies (Imclone: C225 [Goldstein et al. (1995), Clin Cancer Res. 1:1311-1318], and Abgenix: ABX-EGF); (iii) her-2/neu receptor inhibitors such as, for example, Herceptin™ (trastuzumab) and farnesyl transferase inhibitors (FTI) such as, for example, L-744,832 (Kohl et al. (1995), Nat Med. 1(8):792-797); (iv) inhibitors of Akt family kinases or the Akt pathway, such as, for example, rapamycin (see, for example, Sekulic et al. (2000) Cancer Res. 60:3504-3513); (v) cell cycle kinase inhibitors such as, for example, flavopiridol and UCN-01 (see, for example, Sausville (2003) Curr. Med. Chem. Anti-Canc Agents 3:47-56); and (vi) phosphatidyl inositol kinase inhibitors such as, for example, LY294002 (see, for example, Vlahos et al. (1994) J. Biol. Chem. 269:5241-5248). Alternatively, the at least one PD-1/PD-L1 agent and the at least one STI may be in separate pharmaceutical compositions. In a specific embodiment of the present invention, the at least one PD-1/PD-L1 agent and at least one STI may be administered to the patient concurrently or sequentially. In other words, the at least one PD-1/PD-L1 agent may be administered first, the at least one STI may be administered first, or the at least one STI and the at least one PD-1/PD-L1 agent may be administered at the same time. Additionally, when more than one PD-1/PD-L1 agent and/or STI is used, the compounds may be administered in any order.

The pharmaceutical compositions of the invention may further comprise at least one chemotherapeutic agent. Suitable chemotherapeutic agents are described hereinabove. Preferred chemotherapeutic agents include, but are not limited to: paclitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives. In a particular embodiment, the chemotherapeutic agent is paclitaxel. As an alternative, the at least one chemotherapeutic agent and the at least one PD-1/PD-L1 agent may be in separate pharmaceutical compositions.

Cancers that may be treated using the present protocol include, but are not limited to: melanoma, lung cancer, liver, prostate, colon, kidney, breast, head and neck, bladder cancer, gastric cancer, lymphoma, Merkel cell carcinoma, cancer with mismatch repair deficiency or other cancers that may be treated with anti-PD-1/PDL-1 therapy. Other cancers include without limitation, glioblastoma, mesothelioma, renal cell carcinoma, gastric carcinoma, sarcoma, choriocarcinoma, cutaneous basocellular carcinoma, and testicular seminoma.

III. Administration of Pharmaceutical Compositions and Compounds

The pharmaceutical compositions of the present invention can be administered by any suitable route, for example, by injection, by oral, pulmonary, topical or other modes of administration. In general, pharmaceutical compositions of the present invention, comprise, among other things, pharmaceutically acceptable diluents, preservatives, solubilizers, emulsifiers, adjuvants and/or carriers. Such compositions can include diluents of various buffer content (e.g., Tris-HCl, acetate, phosphate), pH and ionic strength; and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington's Pharmaceutical Sciences, 18th Ed. (1990, Mack Publishing Co., Easton, PA 18042) pages 1435-1712 which are herein incorporated by reference. The pharmaceutical composition of the present invention can be prepared, for example, in liquid form, or can be in dried powder form (e.g., lyophilized).

In yet another embodiment, the pharmaceutical compositions of the present invention can be delivered in a controlled release system, such as using an intravenous infusion, an implantable osmotic pump, a transdermal patch, liposomes, or other modes of administration. In a particular embodiment, a pump may be used (see Langer, supra; Sefton, CRC Crit. Ref. Biomed. Eng. (1987) 14:201; Buchwald et al., Surgery (1980) 88:507; Saudek et al., N. Engl. J. Med. (1989) 321:574). In another embodiment, polymeric materials may be employed (see Medical Applications of Controlled Release, Langer and Wise (eds.), CRC Press: Boca Raton, Florida (1974); Controlled Drug Bioavailability, Drug Product Design and Performance, Smolen and Ball (eds.), Wiley: New York (1984); Ranger and Peppas, J. Macromol. Sci. Rev. Macromol. Chem. (1983) 23:61; see also Levy et al., Science (1985) 228:190; During et al., Ann. Neurol. (1989) 25:351; Howard et al., J. Neurosurg. (1989)

71:105). In yet another embodiment, a controlled release system can be placed in proximity of the target tissues of the animal, thus requiring only a fraction of the systemic dose (see, e.g., Goodson, in Medical Applications of Controlled Release, supra, (1984) vol. 2, pp. 115-138). In particular, a controlled release device can be introduced into an animal in proximity to the site of inappropriate immune activation or a tumor. Other controlled release systems are discussed in the review by Langer (Science (1990) 249:1527-1533).

IV. Kits and Articles of Manufacture

Kits comprising components and reagents for practicing the methods disclosed herein are provided. Any of the aforementioned products can be incorporated into the kit which may contain antibodies immunologically specific for the cancer and immune proteins listed herein, including without limitation, PD-1/PD-L1, IFNγ, Akt, Wnt5A, MAPK1, HSP70, TRAP1, HSP90, SerpinH1, VEGFC, R-RAS, HLA-G5, BRAF, NRAS, KIT, TP53, PTEN, EGFR, HER2, ALK, AKT1, KRAS, MET, RET, RHOA, ARID1A, CDH1, CD109, CD151, CD276, CD44, CD46, CD47, CD55, CD58, CD59, CD70, CD9, CD95, CD97, CD99, B7H4, CD63, CD81, CD3, CD4, CD8, CD11, CD14, CD16, CD19, CD20, CD24, CD25, CD27, CD38 CD45, CD68, CD80, CD86, CD138, CD152, CD160, CD223, CD244, CD274, CD276 and CD366, or one or more such antibodies immobilized on a solid support, an oligonucleotide, a polypeptide, a peptide, an antibody, a non naturally occurring detectable label, a positive control marker, or reporter, a pharmaceutically acceptable carrier, a physiologically acceptable carrier, instructions for use, a container for collection, a vessel for administration, an assay substrate, or any combination thereof.

The following examples are provided to illustrate certain embodiments of the invention. It is not intended to limit the invention in any way.

Example I

Materials and Methods
Cell Culture

Human melanoma cell lines MEL624, PD-L1/MEL624, WM1552C, WM35, WM902B, WM793, UACC-903, WM9, A375, and WM164 were cultured in RPMI 1640 medium (Invitrogen) supplemented with 10% (v/v) fetal bovine serum (FBS) (Invitrogen). Mouse melanoma B16-F10 cells were cultured in DMEM (Sigma) supplemented with 10% (v/v) FBS. For stimulation with IFN-γ, cells were incubated with 100 ng/ml of recombinant human IFN-γ (Peprotech) for 48 hr.
Generation of Stable Hrs or PD-L1 Knockdown Melanoma Cells Short hairpin RNAs (shRNAs) against human HRS (HGS) (NM_004712, GCACGTCTTTCCAGAATTCAA, SEQ ID NO: 1), murine PD-L1 (Cd274) (NM_021893, GCGTTGAAGATACAAGCTCAA; SEQ ID NO: 2) or scrambled shRNA-control (Addgene) were packaged into lentiviral particles using 293T cells co-transfected with the viral packaging plasmids. Lentiviral supernatants were harvested 48-72 hr after transfection. Cells were infected with filtered lentivirus and selected by 2 µg/ml puromycin.
Patients and Specimen Collection Thirty patients with Stage III to IV melanoma (Table 1) were enrolled for treatment with pembrolizumab (2 mg/kg by infusion every 3 weeks) under an Expanded Access Program at Penn (http://clinicaltrials.gov identifier NCT02083484) or commercial Keytruda. Patients were consented for blood collection under the University of Pennsylvania Abramson Cancer Center's melanoma research program tissue collection protocol UPCC 08607 in accordance with the Institutional Review Boards (IRB protocol #703001). Peripheral blood was obtained in sodium heparin tubes before each pembrolizumab infusion every 3 weeks for 12 weeks. Assessment of clinical response was performed independently in a double-blind fashion as previously described (Huang et al., 2017). Clinical response was determined as best response based on immune related RECIST (irRECIST) using unidimensional measurements.

TABLE 1

Demographics and basic characteristics of patients

| Characteristic | Total: n = 30 | % of total |
|---|---|---|
| Age, median years (range) | 57 (29-82) | |
| Sex | | |
| Male | n = 16 | 53.33 |
| Female | n = 14 | 46.67 |
| AJCC Stage | | |
| III | n = 5 | 16.67 |
| IV | n = 25 | 83.33 |
| irRECIST evaluated response | | |
| Complete response | n = 6 | 20.00 |
| Partial response | n = 5 | 16.67 |
| Stable disease | n = 8 | 26.67 |
| Progressive disease | n = 11 | 36.67 |

Flow cytometry of patients' PBMCs and in vitro cultured tumor cells Peripheral blood mononuclear cells (PBMCs) were isolated using ficoll gradient and stored using standard protocols. Cryopreserved PBMC samples from pretreatment, cycles 1-4 (weeks 3-12) were thawed and analyzed by flow cytometry as we previously described (Huang et al., 2017). Briefly, live/dead cell discrimination was performed using Live/Dead Fixable Aqua Dead Cell Stain Kit (Life Technologies). Cell surface staining was performed for 30 min at 4° C. Intracellular staining for 60 min on ice was performed after using a fixation/permeabilization kit (eBioscience).

For analyzing the surface expression level of PD-L1 on cultured melanoma cells, cells were stained with fluorophore-labeled anti-PD-L1 antibodies diluted in PBS with 1% FBS for 30 min on ice. For staining of both surface and intracellular PD-L1, cells were first stained with fluorophore-labeled anti-PD-L1 antibodies for 30 min on ice. After that, the surface stained cells were washed, and then fixed and permeabilized, followed by staining with fluorophore-labeled anti-PD-L1 antibodies for 60 min on ice. The intracellular level of PD-L1 protein was calculated by subtracting the mean fluorescence intensity (MFI) of fully stained cells from the MFI of surface only stained cells. All data acquisition was done on a BD Biosciences LSR II flow cytometer and analyzed using FlowJo software (TreeStar).
Purification of the Exosomes For exosome purification from cell culture supernatants, cells were cultured in media supplemented with 10% exosome-depleted FBS. Bovine exosomes were depleted by overnight centrifugation at 100,000 g. Supernatants were collected from 48-72 hr cell cultures and exosomes were purified by a standard differential centrifugation protocol (8-10). Briefly, culture supernatants were centrifuged at 2,000 g for 20 min to remove cell debris and dead cells (Beckman Coulter, Allegra X-14R). Supernatants were then centrifuged at 16,500 g for 45 min (Beckman Coulter, J2-HS) to remove lager vesicles. Exosomes were pelleted by ultracentrifugation of the supernatants at 100,000 g for 2 hr at 4° C. (Beckman Coulter, Optima XPN-100). The pelleted exosomes were suspended in PBS and collected by ultracentrifugation at 100,000 g for 2 hr at 4° C.

For purification of circulating exosomes by differential centrifugation, venous citrated blood from melanoma patients or healthy donors was centrifuged at 1,550 g for 30 min to obtain cell-free plasma (Beckman Coulter, Allegra X-14R). Then 1 ml of the obtained plasma was centrifuged at 16,500 g for 45 min to remove larger vesicles (Eppendorf, 5418R). The collected supernatant will be centrifuged at 100,000 g for 2 hr at 4° C. (Beckman Coulter, Optima™ MAX-XP) to pellet the exosomes. The exosome pellet was suspended in PBS and collected by ultracentrifugation at 100,000 g for 2 hr at 4° C. For purification of circulating exosomes using the exosome isolation kit, 100 µl of cell-free plasma were first pre-cleared of large membrane vesicles by centrifugation at 16,500 g for 45 min (Eppendorf, 5418R). Exosomes were then purified from the supernatants using the exosome isolation kit (Invitrogen, Cat #4484450).

Characterization of the Purified Exosomes

For characterization with flow cytometry, purified exosomes (25 µg) were incubated with 20 µl CD63-coated magnetic beads (Invitrogen, Cat #10606D) in 100 µl PBS with 0.1% bovine serum albumin (BSA) overnight at 4° C. with mixing. Exosomes-coated beads were then washed, and incubated with fluorophore-labeled antibodies, followed by analysis on a LSR II flow cytometer (BD Biosciences).

For verification of purified exosomes using electron microscopy, purified exosomes suspended in PBS were dropped on formvar carbon coated nickel grids. After staining with 2% uranyl acetate, grids were air-dried and visualized using a JEM-1011 transmission electron microscope. For immunogold labeling, purified exosomes suspended in PBS were placed on formvar carbon coated nickel grids, blocked, and incubated with the mouse anti-human monoclonal antibody that recognizes the extracellular domain of PD-L1 (clone 5H1-A3) (Dong et al., 2002), followed by incubation with the anti-mouse secondary antibody conjugated with protein A-gold particles (5 nm). Each staining step was followed by five PBS washes and ten ddH$_2$O washes before contrast staining with 2% uranyl acetate.

The size of exosomes was determined using NanoSight NS300 (Malvern Instruments), which is equipped with fast video capture and particle-tracking software.

For iodixanol density-gradient centrifugation, exosomes harvested by differential centrifugation was loaded on top of a discontinuous iodixanol gradient (5%, 10%, 20% and 40% made by diluting 60% OptiPrep™ aqueous iodixanol with 0.25M sucrose in 10 mM Tris) and centrifuged at 100,000 g for 18 hr at 4° C. Twelve fractions with equal volumes were collected from the top of the gradients, with the exosomes distributed at the density range between 1.13 to 1.19 g/ml, as previously demonstrated (Thery et al., 2006; Colombo et al, 2014; Tibes et al. 2006). The exosomes were further pelleted by ultracentrifugation at 100,000 g for 2 hr at 4° C.

Immunoprecipitation of PD-L1 Proteins from the Cell Culture Supernatants

To analyze PD-L1 proteins secreted by melanoma cells, WM9 cells were treated with IFN-γ (100 ng/ml) in FBS-depleted RPMI 1640 medium for 48 hr. The culture supernatants were collected and centrifuged at 2,000 g for 20 min, and then at 16,500 g for 45 min. For further exosome isolation, supernatants were subjected to ultracentrifugation at 100,000 g for 2 hr at 4° C. For immunoprecipitation of PD-L1 proteins, the concentrated supernatants were incubated with 5 µg/ml mouse anti-human 5H1-A3 monoclonal antibodies and protein A/G agarose overnight at 4° C. The immunoprecipitated proteins were loaded on 12% SDS-polyacrylamide gel electrophoresis and transferred onto nitrocellulose membranes. The blots were blocked with 5% non-fat milk at room temperature for 1 hr, and incubated overnight at 4° C. with two different rabbit anti-human monoclonal antibodies targeting the intracellular domain (Cell Signaling Technology, Cat #13684) and extracellular domain (Cell Signaling Technology, Cat #15165) of PD-L1, respectively, followed by incubation with the horseradish peroxidase (HRP)-conjugated anti-rabbit secondary antibody (Cell Signaling Technology, Cat #7074) at room temperature for 1 hr. The blots were developed with ECL detection reagents (Pierce).

ELISA

For detection of exosomal PD-L1, ELISA plates (96-well) (Biolegend) were coated with 0.25 µg per well (100 µl) of monoclonal antibody against PD-L1 (clone 5H1-A3) overnight at 4° C. Free binding sites were blocked with 200 µl of blocking buffer (Pierce) for 1 hr at room temperature. Then 100 µl of exosome samples, either purified from plasma or cell culture supernatants were added to each well and incubated overnight at 4° C. Biotinylated monoclonal PD-L1 antibody (clone MIH1, eBioscience) was added and incubated for 1 hr at room temperature. A total of 100 µl per well of horseradish peroxidase-conjugated streptavidin (BD Biosciences) diluted in PBS containing 0.1% BSA was then added and incubated for 1 hr at room temperature. Plates were developed with tetramethylbenzidine (Pierce) and stopped with 0.5N H2SO4. The plates were read at 450 nm with a BioTek plate reader. Recombinant human PD-L1 protein (R&D Systems, Cat #156-B7) was used to make the standard curve. Recombinant P-selectin protein (R&D Systems, Cat #137-PS) and mouse PD-L1 protein (R&D Systems, Cat #1019-B7) were used as negative controls to verify the detection specificity. The result of standard curve demonstrated that the established ELISA exhibited a reliable linear detection range from 0.2 to 12 ng/ml.

PD-1-PD-L1 Binding Assay

To test the binding of exosomal PD-L1 to PD-1, 100 µl of exosome samples of different concentrations were captured onto PD-L1 antibody (clone 5H1-A3)-coated 96-well ELISA plates by overnight incubation at 4° C. Then 100 µl of 4 µg/ml biotin-labeled PD-1 protein (BPS Bioscience, Cat #71109) was added and incubated for 2 hr at room temperature. A total of 100 µl per well of horseradish peroxidase-conjugated streptavidin (BD Biosciences) diluted in PBS containing 0.1% BSA was then added and incubated for 1 hr at room temperature. Plates were developed with tetramethylbenzidine (Pierce) and stopped using 0.5N H2SO4. The plates were read at 450 nm with a BioTek plate reader. Recombinant human PD-L1 protein directly coated onto the plates was used as the positive control.

CD8 T Cell-Mediated Tumor Cell Killing Assay

To determine the effects of melanoma cell-derived exosomes on the ability of CD8 T cells to kill tumor cells, anti-CD3/CD28-stimulated CD8 T cells were first pre-treated with PBS (as a control) or melanoma cell-derived exosomes with or without blocking by IgG isotype or PD-L1 antibodies. Then the CD8 T cells with different pre-treatments were co-cultured with melanoma MEL624 cells in 12-well plates for 96 hr at an effector to target (E:T) ratio of 10:1. The wells were then washed with PBS to remove T cells and the survived tumor cells were fixed and visualized by crystal violet staining. The dried plates were imaged and quantified for the intensity using ImageJ.

Treatment of CD8 T Cells with the Exosomes

To block PD-L1 on exosome surface, the purified exosomes were incubated with PD-L1 blocking antibodies or IgG isotype antibodies in 100 μl PBS, and then washed with 30 ml PBS and pelleted by ultracentrifugation to remove the non-bound free antibodies. Human peripheral T cells or mouse splenic T cells stimulated with anti-CD3 (2 μg/ml) and anti-CD28 (2 μg/ml) antibodies for 48 hr and then incubated with human melanoma cell-derived exosomes or mouse B16-F10 cell-derived exosomes with or without PD-L1 blocking for 36-72 hr. The cells were then collected, stained, and analyzed by flow cytometry.

Reverse Phase Protein Array (RPPA)

RPPA was performed at the MD Anderson Cancer Center core facility using 50 μg protein per sample. All of the antibodies were validated by western blotting (Tibes et al., 2006).

Immunofluorescence Staining

Immunofluorescence staining was performed on fixed cells or formalin-fixed, paraffin-embedded (FFPE) sections. For fixed cells, permeabilization with 0.1% Triton X-100 was performed before blocking with bovine serum albumin (BSA) buffer for 1 hr. For FFPE sections, antigen retrieval by steaming in citrate buffer (pH=6.0) was performed before blocking. The fixed cells or FFPE sections were incubated with primary antibodies overnight at 4° C., followed by incubation with fluorophore-conjugated secondary antibodies for 1 hr. Nuclei were stained with DAPI. Samples were observed using a Leica fluorescence microscope at 63× magnification.

Western Blot Analysis

Whole cell lysates or exosomal proteins were separated using 12% SDS-polyacrylamide gel electrophoresis and transferred onto nitrocellulose membranes. The blots were blocked with 5% non-fat dry milk at room temperature for 1 hr, and incubated overnight at 4° C. with the corresponding primary antibodies at dilutions recommended by the suppliers, followed by incubation with HRP-conjugated secondary antibodies (Cell Signaling Technology) at room temperature for 1 hr. The blots on the membranes were developed with ECL detection reagents (Pierce).

In Vivo Mice Study

All animal experiments were performed according to protocols approved by the Institutional Animal Care and Use Committee (IACUC) of the University of Pennsylvania. For establishing human melanoma xenograft model in nude mice, WM9 cells ($5\times10^6$ cells in 100 μm medium) were injected into flanks of 8-week-old female athymic nude mice. Tumors were measured using a digital caliper and the tumor volume was calculated by the formula (width)2× length/2. Mice were euthanized 30 days after cell inoculation or the longest dimension of the tumors reached 2.0 cm before 30 days Immediately following euthanasia, blood samples were harvested by cardiac puncture, and exosomes were purified and detected by ELISA using aforementioned method. Exosomes purified from sex-, age- and weight-matched healthy nude mice without xenograft were used as the control.

For establishing syngeneic mouse melanoma model in C57BL/6 mice, B16-F10 cells or B16-F10 PD-L1-KD cells ($5\times10^5$ cells in 100 μl medium) were subcutaneously injected into immunocompetent C57BL/6 mice. After cell inoculation, tail vein injections of exosomes (100 μg in 100 μl PBS) were performed every 3 days. Mice were weighted every 3 days. Tumors were measured using a digital caliper and the tumor volume was calculated by the formula (width) 2×length/2. The mice were euthanized before the longest dimension of the tumors reached 2.0 cm. For flow cytometry, the spleen and tumor samples were harvested, and single cell suspensions were prepared and red blood cells were lysed using ACK Lysis Buffer.

Statistical Analyses

RPPA data analysis was performed according to the protocol from the M.D. Anderson Cancer Center. Specifically, relative protein levels for each sample were determined by interpolation of each dilution curves from the "standard curve" (supercurve) of the slide (antibody). Supercurve is constructed by a script in R written by the RPPA core facility. These values are defined as Supercurve Log 2 value. All the data points were normalized for protein loading and transformed to linear value, designated as "Normalized Linear". "Normalized Linear" value was transformed to Log 2 value, and then median-centered for further analysis. Median-Centered values were centered by subtracting the median of all samples in a given protein. All of the above-mentioned procedures were performed by the RPPA core facility. The normalized data provided by the RPPA core facility were analyzed by Cluster 3.0 (http://bonsai.ims.u-tokyo.ac.jp/~mdehoon/software/cluster/) and visualized using the Java TreeView 1.0.5 (http://jtreeview.sourceforge.net/).

All other statistical analyses were performed using GraphPad Prism, version 6.0. Normality of distribution was determined by D'Agostino-Pearson omnibus normality test and variance between groups was assessed by the F-test. For normally distributed data, significance of mean differences was determined using two-tailed paired or unpaired Student's t-tests; for groups that differed in variance, unpaired t-test with Welch's correction was performed. For data that were not normally distributed, non-parametric Mann-Whitney U-tests or Wilcoxon matched-pairs test were used for unpaired and paired analysis, respectively. Correlations were determined by Pearson's r coefficient. Two-way ANOVA was used to compare mouse tumor volume data among different groups. Log-rank and Wilcoxon tests were used to analyze the mouse survival data. Error bars shown in graphical data represent mean±s.d. A two-tailed value of $P<0.05$ was considered statistically significant.

Results

Exosomes are 50-120 nm diameter lipid-encapsulated vesicles secreted by cells. Exosomes carry bioactive molecules that act locally and in circulation to influence the extracellular environment and the immune system (Becker et al., 2016; Kalluri, 2016). To understand the role of exosomes in melanoma progression, we analyzed exosomes released from a panel of human primary and metastatic melanoma cell lines. The exosomes were purified from cell culture supernatants by differential centrifugation, a standard method for purifying exosomes and separating them from shedding vesicles and apoptotic bodies (Colombo et al., 2014; Peinado et al., 2012; Thery et al., 2006). The purified exosomes were verified as 50-120 nm diameter membrane-bound vesicles by transmission electron microscopy (TEM) and light-scattering based nanoparticle tracking analysis (FIG. 1A-1B). Proteins carried by the purified exosomes were then analyzed by reverse phase protein array (RPPA), a large-scale antibody-based quantitative proteomics technology (Tibes et al., 2006). The RPPA revealed that PD-L1 was abundantly present in exosomes, and its level was significantly higher in exosomes derived from metastatic melanoma cells compared to primary melanoma cells (FIG. 1C, FIG. 2A), suggesting that exosomal secretion of PD-L1 associates with melanoma progression. The RPPA result was verified by western blotting, which detected high levels of PD-L1 in the exosomes secreted by metastatic melanoma cells (FIG. 1D). Using iodixanol density gradient centrifugation, we further confirmed that PD-L1 co-fractionated with the exosomes (FIG. 1E), which floated at densities ranging from 1.13 to 1.19 g/ml as previously reported (Colombo et al., 2014; Melo et al., 2015; Thery et al., 2006). In addition to human cells, mouse metastatic melanoma B16-F10 cells also secreted exosomes that carried a high level of PD-L1 (FIG. 2B).

Tumor cell surface PD-L1 can be up-regulated in response to IFN-γ secreted by activated T cells, and PD-L1 binds to PD-1 through its extracellular domain to inactivate the T cells (Chen & Han, 2015; Garcia-Diaz et al., 2017; Ribas et al., 2016). Using immuno-electron microscopy (FIG. 1F), flow cytometry (FIG. 1G), and enzyme-linked immunosorbent assay (ELISA) (FIG. 1H-1I), we found that the exosomal PD-L1 has the same membrane topology as the cell surface PD-L1, with its extracellular domain exposed on the surface. This membrane topology allows exosomal PD-L1 to bind PD-1 in a concentration-dependent manner, similar to the tumor cell surface PD-L1, and this interaction can be disrupted by PD-L1 blocking antibodies (FIG. 1J). We further found that the level of exosomal PD-L1 secreted by melanoma cells increased significantly upon IFN-γ treatment, and correspondingly, these exosomes displayed an increased binding capacity for PD-1 (FIG. 1G-1K). Compared to tumor cell surface PD-L1, IFN-γ-mediated exosomal PD-L1 induction may serve as a more effective means for the tumor cells to adapt to the immune pressure, as will be discussed later.

Exosomes are generated and released through a defined intracellular trafficking route (Colombo et al., 2014; Kalluri, 2016; Thery et al., 2006). We therefore examined the localization of PD-L1 in melanoma cells by immunofluorescence. PD-L1 co-localized with the exosome marker CD63 (FIG. 1L), and the ESCRT subunit Hrs (FIG. 2C), which mediates the recognition and sorting of exosomal cargos (Schmidt & Teis, 2012). Knockdown of HRS led to a decrease in the level of PD-L1 in secreted exosomes and a concomitant increase of PD-L1 in the whole cell lysates, as measured by western blotting and flow cytometry (FIG. 1M, FIG. 2D). Since Hrs mediates the sorting of ubiquitinated cargos into exosomes (Schmidt & Teis, 2012) and a population of PD-L1 was shown to be ubiquitinated in cells (Horita et al., 2017; Lim et al., 2016), we tested whether PD-L1 interacts with Hrs. Indeed, PD-L1 co-immunoprecipitated with Hrs from the cell lysates (FIG. 1N). These data suggest an ESCRT-dependent pathway for the exosomal secretion of PD-L1.

To test whether melanoma cells secrete PD-L1 in other forms, we immunoprecipitated PD-L1 proteins from the melanoma cell culture supernatants. Western blotting using two different monoclonal antibodies that targeted the extracellular domain (ECD) and intracellular domain (ICD) of PD-L1, respectively, detected the majority of immunoprecipitated PD-L1 proteins at 45 kD (FIG. 2E), which is the molecular weight of the full-length glycosylated membrane-bound PD-L1 (Li et al., 2016). This is consistent with previous characterization of PD-L1 from cell culture supernatants (Chen et al., 2011; Frigola et al., 2011). The antibody against the ECD also detected a smaller fraction of PD-L1 at 40 kD, which might be PD-L1 proteins cleaved from the cell surface or alternatively spliced PD-L1 proteins lacking the ICD and transmembrane domain (Zhou et al., 2017).

Next, we established human melanoma xenografts in nude mice to test the secretion of exosomal PD-L1 by melanoma cells in vivo. Blood samples from mice with or without the human melanoma xenografts were collected for exosome purification and subsequent detection of human PD-L1 proteins by ELISA (FIG. 3A). Monoclonal antibodies targeting the extracellular domain of human PD-L1 (FIG. 4A-4B) specifically identified human PD-L1 on the circulating exosomes isolated from the mice bearing human melanoma xenografts but not the control mice (FIG. 3B, FIG. 4C-4D). Moreover, in mice bearing human xenografts, the level of circulating exosomal PD-L1 positively correlated with the tumor size (FIG. 3C).

Figure 4E:
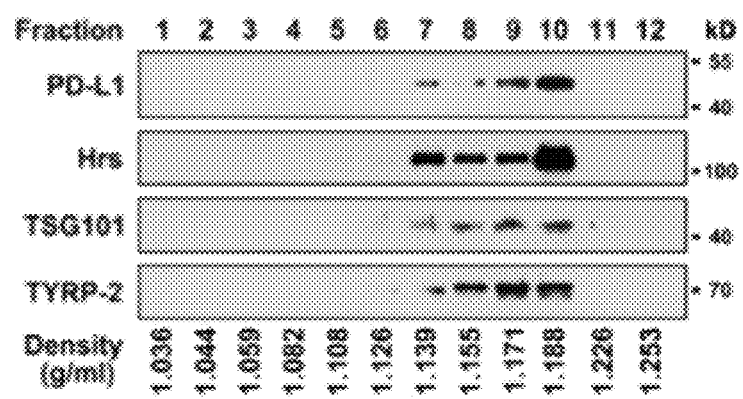

Recently, PD-L1 has been found in cancer patient blood samples (Finkelmeier et al., 2016; Frigola et al., 2011; Rossille et al., 2014; Zhou et al., 2017). To investigate whether PD-L1 in blood is carried by exosomes, the circulating exosomes were purified from the plasma of patients with metastatic melanoma, and verified by TEM (FIG. 3D) and iodixanol density gradient centrifugation (FIG. 4E). PD-L1 proteins co-fractionated with the circulating exosomes and the melanoma-specific exosome marker TYRP-2 (Peinado et al., 2012) (FIG. 4E). Western blot analysis confirmed the presence of PD-L1 in circulating exosomes derived from all of the patients tested (FIG. 3E). In agreement, ELISA of PD-L1 on the purified circulating exosomes showed that exosomal PD-L1 accounted for approximately 66% of the total circulating PD-L1 in the patient plasma (FIG. 3F). These results confirm that the majority of circulating PD-L1 in patients with metastatic melanoma is carried on the exosomes.

Using ELISA, we also found that the level of PD-L1 on the circulating exosomes from patients with metastatic melanoma was approximately 5 times higher than that from healthy donors (P<0.001) (FIG. 6G). The receiver operating characteristic (ROC) curve suggests that the level of circulating exosomal PD-L1 distinguished melanoma patients from healthy donors with an area under the curve (AUC) of 0.95, a sensitivity of 93.33%, and a specificity of 100% (FIG. 3H). The level of circulating exosomal PD-L1 in melanoma patients with measureable tumor burden was significantly higher than that in the stage-matched melanoma patients with no evidence of disease (NED) (FIG. 3I). These results implicate elevated levels of circulating exosomal PD-L1 as functionally important in patients with metastatic melanoma.

The current model for PD-L1-mediated immunosuppression is based on the interaction between PD-L1 on tumor cell surface and PD-1 on T cells. This interaction delivers the inhibitory signal that induces functional "exhaustion" or apoptosis of T cells (Chen & Han, 2015; Dong et al., 2002; Topalian et al., 2016). Since exosomal PD-L1 has the same membrane topology as tumor cell surface PD-L1 and can bind to PD-1 (FIG. 1F-1J), we tested whether it is capable of inhibiting CD8 T cells. First, we took advantage of MEL624 cells, a melanoma cell line that does not express endogenous PD-L1, as well as other immunosuppressive proteins (e.g. FasL and TRAIL) (Dong et al., 2002). In contrast to the exosomes purified from the parental MEL624 cells that have no endogenous PD-L1 (FIG. 5A-5D), PD-L1-enriched exosomes derived from PD-L1-expressing MEL624 cells ("PD-L1/MEL624") significantly inhibited the activated human CD8 T cells, as demonstrated by the reduced expression of the proliferation marker Ki-67 and the cytotoxic protein granzyme B (GzmB) (FIG. 6A). Pretreatment of the exosomes with the anti-PD-L1 antibodies nearly abolished the effect. In addition to the PD-L1/

MEL624 cells, exosomes secreted by human melanoma WM9 cells that expresses endogenous PD-L1 (FIG. 1C-1K) also induced a significant reduction in Ki-67 and GzmB expression in the activated human CD8 T cells (FIG. 7A). Blocking the interaction between exosomal PD-L1 and T cell PD-1 using anti-PD-L1 or anti-PD-1 antibodies significantly attenuated the inhibitory effects on PD-1$^+$ CD8 T cells, but showed negligible effects on PD-1$^-$ CD8 cells (FIG. 6B-6C, FIG. 7B). Similar effects were observed using mouse splenic CD8 T cells incubated with the exosomes derived from mouse melanoma B16-F10 cells (FIG. 8A). CD8 T cells with prolonged exosome treatment underwent apoptosis, which was more prominent in PD-1$^+$ CD8 T cells; PD-L1 blocking antibodies significantly attenuated this effect (FIG. 6D, FIG. 8B-8C). Moreover, using a tumor cell-killing assay, we further demonstrate that pre-treating CD8 T cells with exosomes derived from PD-L1/MEL624 and WM9 cells, but not parental MEL624 cells, significantly inhibited their ability to kill MEL624 cells (FIG. 6E-6F, FIG. 7C). These data indicate that melanoma-derived exosomal PD-L1 inhibits CD8 T cells in vitro by impeding their proliferation and cytotoxicity, and inducing apoptosis.

Figure 9A:
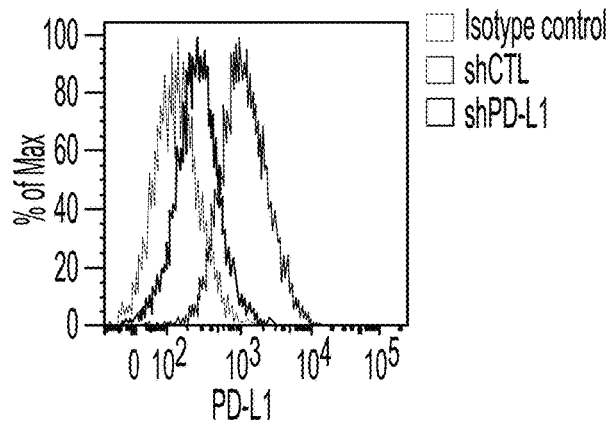
Figure 9C:
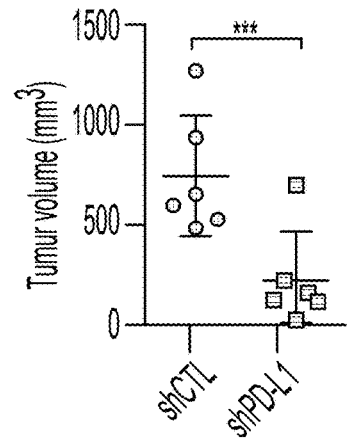
Figure 9B:
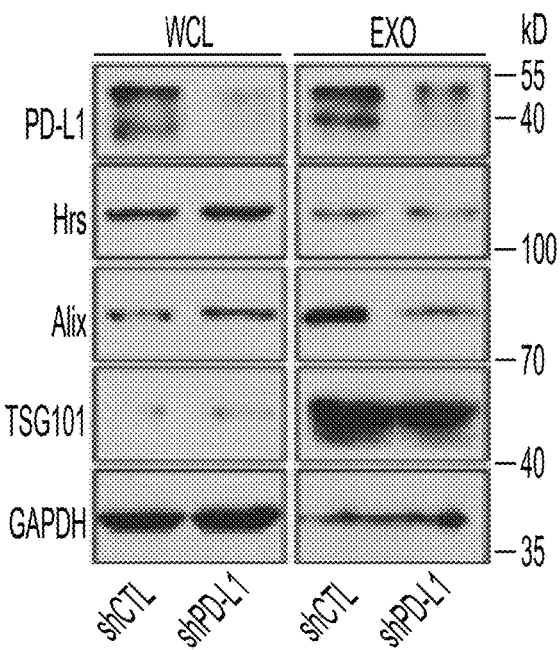
Figure 9D:
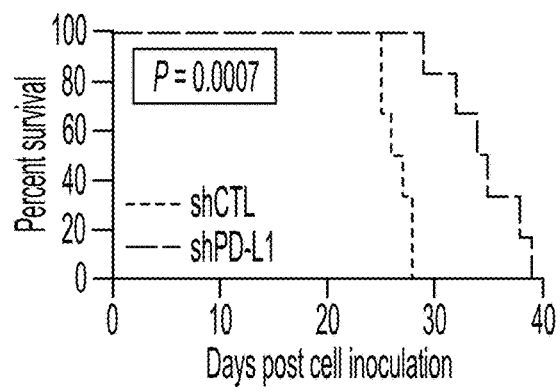
Figure 9E:
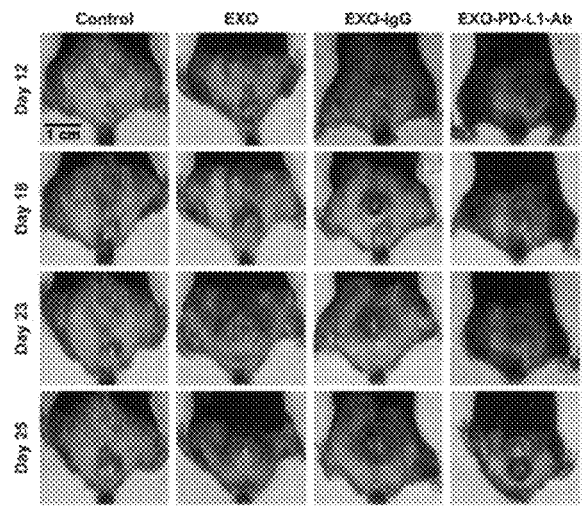

To examine the effects of exosomal PD-L1 in vivo, a syngeneic mouse B16-F10 melanoma model was established in immunocompetent C57BL/6 mice. Since B16-F10 cells secrete exosomes carrying PD-L1 (FIG. 2B), which may mask the effect of exogenously applied exosomes, we knocked down the endogenous PD-L1 in B16-F10 cells with lentiviral shRNA ("B16-F10 PD-L1-KD") (FIG. 9A-9B). Knockdown of PD-L1 significantly inhibited B16-F10 tumor growth in C57BL/6 mice (FIG. 9C) and prolonged their overall survival (FIG. 9D). Injection of exosomes derived from parental B16-F10 cells significantly promoted the growth of B16-F10 PD-L1-KD tumors (FIG. 6G, FIG. 9E) and shortened the overall survival of mice (FIG. 6H-6I). However, pre-treatment of the exosomes with anti-PD-L1 antibodies, but not IgG isotype antibodies, protected the mice from tumor growth and prolonged their overall survival (FIG. 6G-6I, FIG. 9E). To better understand the mechanism for the observed effects, we examined the frequency and phenotypes of CD8 tumor-infiltrating lymphocytes (TILs) Immunofluorescence staining of the tumors showed that the number of CD8 TILs decreased significantly after injection of B16-F10 exosomes; blocking exosomal PD-L1 with antibodies attenuated this effect (FIG. 6J-6K). Flow cytometric analysis showed that exosome treatment resulted in a decrease in the proliferation of CD8 TILs, which was rescued by PD-L1 blockade (FIG. 6L). These data show that exosomal PD-L1 inhibits CD8 T cells and thus promotes tumor progression.

We next sought to understand whether exosomal PD-L1 had a systemic immunosuppressive effect. We phenotyped the splenic T cells from mice bearing B16-F10 PD-L1-KD tumors. B16-F10 exosomes significantly decreased the proportion of proliferating splenic PD-1$^+$ CD8 T cells, whereas pre-treatment with PD-L1 blocking antibodies attenuated this effect (FIG. 6L). These data demonstrate that exosomal PD-L1 suppresses anti-tumor immunity systemically.

Figure 10D:
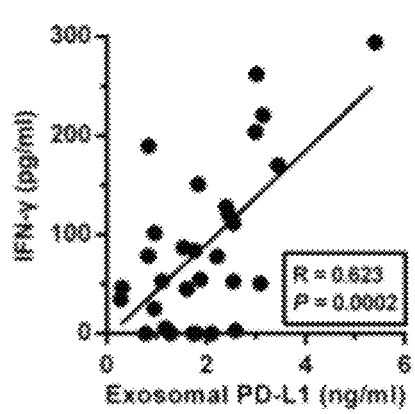

As exosomal PD-L1 mediates immunosuppression and can be assessed in patient blood by ELISA (FIG. 3F-3I), we set to examine whether the level of circulating exosomal PD-L1 is associated with clinical responses to anti-PD-1 therapy in patients with metastatic melanoma. The pre-treatment level of circulating exosomal PD-L1 was significantly higher in patients who failed to respond to the anti-PD-1 antibody, pembrolizumab (FIG. 10A). The ROC analysis demonstrated that the pre-treatment circulating exosomal PD-L1 level segregated responders and non-responders to pembrolizumab with an AUC of 0.885, a sensitivity of 94.74%, and a specificity of 81.82% (FIG. 10B). A pre-treatment circulating exosomal PD-L1 level higher than 1.41 ng/ml was associated with poorer clinical outcome by objective response rate (ORR) (FIG. 10C). As IFN-γ up-regulates exosomal PD-L1 (FIG. 1G-1K) and our recent data showed that the pre-treatment levels of IFN-γ were significantly higher in patients who did not respond to pembrolizumab (Huang et al., 2017), we tested whether there was a correlation between circulating exosomal PD-L1 and IFN-γ. Indeed, the level of circulating exosomal PD-L1 positively correlated with the level of circulating IFN-γ (FIG. 10D). These results suggest that a higher level of circulating exosomal PD-L1 before treatment is an indicator of poor prognosis for anti-PD-1 therapy.

Figure 10E:
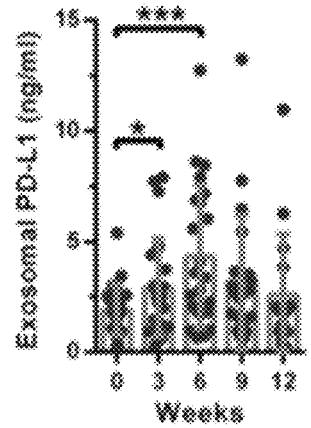
Figure 10F:
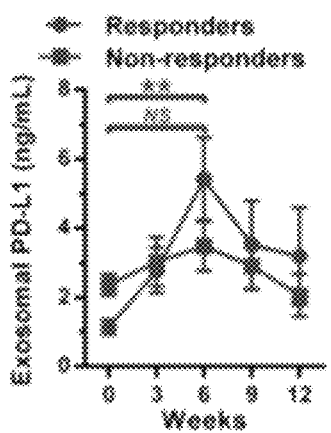
Figure 10G:
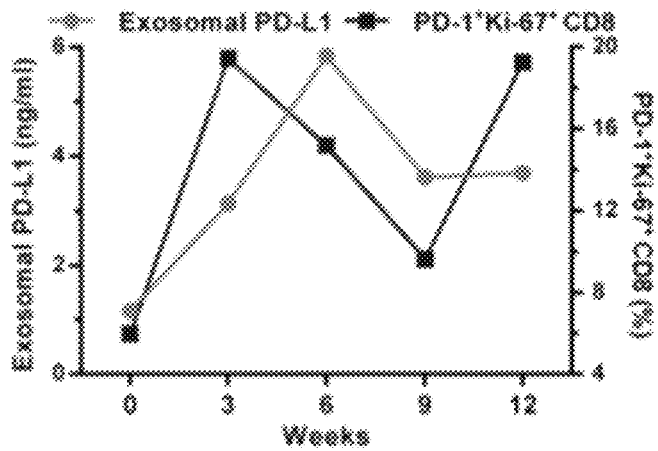

Next, we examined circulating exosomal PD-L1 in patients on pembrolizumab therapy in our clinical trial. The levels of circulating exosomal PD-L1 increased significantly during pembrolizumab treatment, peaking at Week 6 (FIG. 10E). However, this effect was only observed for clinical responders (FIG. 10F). We then examined the relationship between exosomal PD-L1 and CD8 T cell re-invigoration in these clinical responders. CD8 T cell proliferation and re-invigoration peaked at Week 3, similar to our previous study (Huang et al., 2017), and preceded the peaking of exosomal PD-L1 at Week 6 (FIG. 10G). Moreover, for clinical responders, both the absolute value and fold change of Ki-67 in PD-1$^+$ CD8 T cells positively correlated with those of circulating exosomal PD-L1 (FIG. 10H-10I). We predicted that the magnitude of the on-treatment increase in circulating exosomal PD-L1 is a potential indicator of the adaptive response of tumor cells to T cell re-invigoration and appears to be associated with clinical outcomes. Indeed, the clinical responders had a greater increase in the level of circulating exosomal PD-L1 at 6 weeks into treatment (FIG. 10J). ROC analysis determined that the magnitude of the increase in circulating exosomal PD-L1 at Week 6 stratified patients by clinical response to pembrolizumab with an AUC of 0.96 exhibiting a sensitivity of 92.31%, and a specificity of 100% (FIG. 10K). The significant on-treatment increase in circulating exosomal PD-L1 in clinical responders followed and correlated positively with the on-treatment T cell re-invigoration, reflecting an adaptive response of the tumors to the immune reinvigoration generated by the anti-PD-1 therapy. Our findings are consistent with previous studies showing that the adaptive expression of tumor PD-L1 in response to PD-1 blockade-induced immune reinvigoration and IFN-γ production correlated with positive prognosis (Herbst et al., 2014; Shin et al., 2017; Zaretsky et al., 2016).

Based on the cell biological, immunological and clinical studies, we propose a modified model of the PD-L1/PD-1 checkpoint-mediated tumor immune evasion (FIG. 11). In addition to the direct tumor cell-CD8 T cell interaction, melanoma cells secrete PD-L1 exosomes that function as the frontline infantry to interact with CD8 T cells in the tumor microenvironment and in the circulation to systemically battle the anti-tumor immunity. As a single tumor cell can release multiple copies of exosomes (Peinado et al., 2012), the interaction between the exosomes and T cells provides a highly effective means for tumor cells to suppress the immune system. Since exosomal PD-L1-mediated T cell inhibition can be blocked by both anti-PD-L1 and PD-1 antibodies (FIG. 6A-6J, FIG. 7-9), the new model also raises the possibility that disrupting the interaction between the exosomal PD-L1 and T cell PD-1 is a previously unrecognized mechanism involved in the current PD-L1/PD-1 blockade-based therapies, and may offer an explanation to the recent observation that a subset of cancer patients with no PD-L1 expression on tumor surface can still benefit from the anti-PD-1/PD-L1 therapies (Larkin et al., 2015; Patel & Kurzrock, 2015). We also found that the level of PD-L1 on exosomes secreted by tumor cells is up-regulated by IFN-γ. While IFN-γ secreted by T cells has been shown to up-regulate the expression of tumor cell surface PD-L1 as an adaptive response (Chen & Han, 2015; Garcia-Diaz et al., 2017; Topalian et al., 2016), the increase of PD-L1 on exosomes in response to IFN-γ will allow the immune checkpoint function to be carried out in a manner that is less spatially restricted. Considering that exosomal PD-L1 primarily targets PD-1$^+$ CD8 T cells, which represent the antigen experienced T cells that secrete IFN-γ, the level of exosomal PD-L1 may reflect the dynamic interplay between the tumor and immune cells. In addition to PD-L1, other proteins may also contribute to the immunosuppressive effects induced by melanoma-derived exosomes. For example, it was previously reported that exosomes secreted by tumor cells carry FasL, which can inhibit CD8 T cells via the general apoptosis pathway (Andreola et al., 2002; Taylor et al., 2003). However, PD-L1 will enable the exosomes to predominantly target the PD-1$^+$ CD8 T cells, so that the tumor cells can more effectively counteract the immune pressure.

Our clinical study suggests that the circulating exosomal PD-L1 before and on pembrolizumab treatment may reflect distinct states of anti-tumor immunity. The pre-treatment level may reflect a prominent role of exosomal PD-L1 in immune dysfunction and dysregulation. Patients with pre-treatment exosomal PD-L1 below a critical level will likely respond to anti-PD-L1/PD-1 therapies, whereas patients with exosomal PD-L1 at or above a critical level will show no response. It is possible that higher levels of exosomal PD-L1 may "exhaust" patient T cells to a breaking point that cannot be overcome by the treatment. For the on-treatment levels of exosomal PD-L1, however, its increase would reflect the presence of a successful anti-tumor immunity elicited by the anti-PD-1 therapy. Although the elevation of PD-L1 on exosomes or tumor cells in response to IFN-γ would enable the tumor cells to adaptively inactivate CD8 T cells, it is futile during the treatment because the PD-L1/PD-1 interaction is blocked by pembrolizumab. For non-responders, no increase in exosomal PD-L1 could be observed. Previous studies suggest that tumor cells in non-responders may have adaptively down-regulated their response to IFN-γ in order to avoid the detrimental increase in antigen presentation and to escape the anti-proliferative effects induced by IFN-γ (Shin et al., 2017; Zaretsky et al., 2016).

Our study offers a rationale for employing circulating exosomal PD-L1 as an early on-treatment predictor for the clinical outcomes of anti-PD-1 therapy (FIG. 12A-12B). It also sheds light on the possible causes for the failure of anti-PD-1 therapies in some patients (FIG. 12C). Tumor PD-L1 has been suggested as a predictive biomarker for clinical responses to anti-PD-1 therapy (Patel & Kurzrock, 2015; Reck et al., 2016). Considering the heterogeneity and dynamic nature of PD-L1 expression in tumors, and the difficulty in tracking the changes in PD-L1 through repeated tumor biopsies during the course of the therapy, developing exosomal PD-L1 as a blood-based biomarker offers an attractive option for monitoring the efficacy of anti-PD-1 therapies and for future mechanistic dissection of exosome-mediated cancer cell immune evasion.

The PD-L1/PD-1 blockade-based immunotherapies have shown great promise to treat many types of solid tumors, including metastatic melanoma (Chen & Han, 2015; Topalian et al., 2016). However, only a minority of patients responds to the therapy (Ribas et al., 2016; Zaretsky et al., 2016). A better understanding of the mechanism by which melanoma cells exploit the PD-L1/PD-1 interaction to inhibit T cells and evade the immune system will help improve the efficacy of immune checkpoint blockade-based therapies. In addition to melanoma, our findings apply to other types of cancers that are treated with anti-PD-1/PD-L1 therapy.

Example II

Isolation of Immune Cell-Derived Shedding Vesicles and Exosomes and Methods of Use Thereof
Materials and Methods
Patients and Specimen Collection Patients with Stage III to IV melanoma were enrolled for treatment with pembrolizumab or commercial Keytruda (2 mg/kg by infusion every 3 weeks). Patients consented to blood collection under the University of Pennsylvania Abramson Cancer Center's melanoma research program tissue collection protocol UPCC 08607 in accordance with the Institutional Review Boards (IRB protocol #703001). Peripheral blood was obtained in sodium heparin tubes before each pembrolizumab infusion every 3 weeks for 12 weeks. Assessment of clinical response was performed independently in a double-blind fashion as previously described (Huang et al., 2017). Clinical response was determined as best response based on immune related RECIST (irRECIST) using unidimensional measurements.

Isolation and Activation of Human Peripheral and T Cells

Human peripheral blood mononuclear cells (PBMCs) were isolated using ficoll gradient. T cells were further purified from PBMCs using Dynabeads Untouched Human T Cells Kit according to the manufacturer's instruction (Thermo Fisher Scientific). The purified T cells were cultured in RPMI1640 supplemented with 10% exosome-depleted fetal bovine serum (FBS), 100 mg/mL streptomycin/penicillin, 2 mM L-glutamine and 1 mM sodium pyruvate (Sigma-Aldrich, Sweden) at 37° C., 5% $CO_2$. For T cell activation, the purified T cells were incubated with anti-CD3 (2 μg/ml) and anti-CD28 (2 μg/ml) antibodies for 72 hr.

Purification and Characterization of Shedding Vesicles and Exosomes

To purify shedding vesicles and exosomes secreted by T cells, culture supernatants were collected from both activated and non-activated T cells. Culture supernatants were centrifuged at 2,000 g for 20 min to remove cell debris and dead cells (Beckman Coulter, Allegra X-14R). Supernatants were then centrifuged at 20,500 g for 60 min at 4° C. (Beckman Coulter, J2-HS) to collect shedding vesicles. Exosomes were pelleted by ultracentrifugation of the supernatants at 100,000 g for 2 hr at 4° C. (Beckman Coulter, Optima XPN-100).

For purification of circulating shedding vesicles and exosomes by differential centrifugation, venous citrated blood from melanoma patients or healthy donors was centrifuged at 1,550 g for 30 min to obtain cell-free plasma (Beckman Coulter, Allegra X-14R). Then 1 ml of the obtained plasma was centrifuged at 20,500 g for 60 min at 4° C. to collect shedding vesicles (Eppendorf, 5418R). The collected supernatant will be centrifuged at 100,000 g for 2 hr at 4° C. (Beckman Coulter, Optima™ MAX-XP) to pellet the exosomes. For purification of circulating exosomes using the exosome isolation kit, 100 µl of cell-free plasma were first centrifuged at 20,500 g for 60 min at 4° C. (Eppendorf, 5418R) to collect shedding vesicles. Exosomes were then purified from the supernatants using the exosome isolation kit (Invitrogen, Cat #4484450).

For characterization with flow cytometry, purified exosomes were incubated with CD63-, CD3-, CD4- or CD8- coated magnetic beads in PBS with 0.1% bovine serum albumin (BSA) overnight at 4° C. with mixing. Exosomes-coated beads were then washed, and incubated with fluorophore-labeled antibodies, followed by analysis on a LSR II flow cytometer (BD Biosciences).

For verification of purified exosomes using electron microscopy, purified exosomes suspended in PBS were dropped on formvar carbon coated nickel grids. After staining with 2% uranyl acetate, grids were air-dried and visualized using a JEM-1011 transmission electron microscope. For immunogold labeling, purified exosomes suspended in PBS were placed on formvar carbon coated nickel grids, blocked, and incubated with the primary antibodies, followed by incubation with the anti-mouse secondary antibody conjugated with protein A-gold particles (5 nm). Each staining step was followed by five PBS washes and ten ddH$_2$O washes before contrast staining with 2% uranyl acetate.

The size of exosomes was determined using NanoSight NS300 (Malvern Instruments), which is equipped with fast video capture and particle-tracking software.

For iodixanol density-gradient centrifugation, exosomes harvested by differential centrifugation was loaded on top of a discontinuous iodixanol gradient (5%, 10%, 20% and 40% made by diluting 60% OptiPrep™ aqueous iodixanol with 0.25M sucrose in 10 mM Tris) and centrifuged at 100,000 g for 18 hr at 4° C. Twelve fractions with equal volumes were collected from the top of the gradients. The exosomes were further pelleted by ultracentrifugation at 100,000 g for 2 hr at 4° C.

ELISA

For detection of the immunomodulator proteins (e.g. CD276) on the shedding vesicles and exosomes derived from T cells, ELISA plates were coated with monoclonal antibody against CD276 overnight at 4° C. Free binding sites were blocked with 200 µl of blocking buffer (Pierce) for 1 hr at room temperature. Then 100 µl of exosome samples, either purified from plasma or cell culture supernatants were added to each well and incubated overnight at 4° C. Biotinylated monoclonal CD276 antibody was added and incubated for 1 hr at room temperature. A total of 100 µl per well of horseradish peroxidase-conjugated streptavidin (BD Biosciences) diluted in PBS containing 0.1% BSA was then added and incubated for 1 hr at room temperature. Plates were developed with tetramethylbenzidine (Pierce) and stopped with 0.5N H$_2$SO$_4$. The plates were read at 450 nm with a BioTek plate reader. Recombinant human PD-1 protein was used to make the standard curve.

Western Blot Analysis

Whole cell lysates or proteins of shedding vesicles or exosomes were separated using 12% SDS-polyacrylamide gel electrophoresis and transferred onto nitrocellulose membranes. The blots were blocked with 5% non-fat dry milk at room temperature for 1 hr, and incubated overnight at 4° C. with the corresponding primary antibodies at dilutions recommended by the suppliers, followed by incubation with HRP-conjugated secondary antibodies (Cell Signaling Technology) at room temperature for 1 hr. The blots on the membranes were developed with ECL detection reagents (Pierce).

Results

The purified shedding vesicles and exosomes secreted by T cells were first confirmed as 100-1000 nm and 40-100 nm membrane vesicles, respectively, by the Nanosight nanoparticle tracking analysis (NTA) technique. The NTA result also demonstrated that there was no significant difference in the size distribution between the shedding vesicles and exosomes secreted by activated and non-activated T cells (FIG. 13A). However, activated T cells secreted significantly more shedding vesicles and exosomes compared to non-activated T cells (FIG. 13B). Moreover, shedding vesicles and exosomes secreted by activated T cells showed much higher protein levels than those derived from non-activated T cells (FIG. 13C). In agreement with the protein quality results, a significant increase in the levels of exosomal markers was observed in the shedding vesicles and exosomes purified from activated T cells compared to non-activated T cells (FIG. 13D). These results indicate that activated T cell-derived shedding vesicles and exosomes carry more protein cargoes than those derived from non-activated T cells.

The shedding vesicles and exosomes secreted by activated and non-activated T cells were further analyzed by immunoblotting for the presence of immunomodulator proteins (FIG. 13D), including CD152, CD223, CD274, CD276, and CD366. Although showing different levels, the T cell surface markers CD3, CD4 and CD8 were clearly detected in the shedding vesicles and exosomes secreted by both activated and non-activated T cells. CD223, CD274, CD276 and CD366 were exclusively detected in the shedding vesicles and exosomes derived from the activated T cells. However, the level of CD152 was higher in the shedding vesicles but not the exosomes secreted by activated T cells compared to non-activated T cells. These above results demonstrate that T cells, especially the activated T cells, secrete high levels of extracellular vesicles that carry immunomodulator proteins.

REFERENCES

Andaloussi, S. E., Mager, I., Breakefield, X. O., and Wood, M. J. (2013). Extracellular vesicles: biology and emerging therapeutic opportunities. Nat. Rev. Drug Discov. 12, 347-357.

Andreola, G., Rivoltini, L., Castelli, C., Huber, V., Perego, P., Deho, P., Squarcina, P., Accornero, P., Lozupone, F., Lugini, L., et al. (2002). Induction of lymphocyte apoptosis by tumor cell secretion of FasL-bearing microvesicles. J. Exp. Med. 195, 1303-1316.

Baietti, M. F., Zhang, Z., Mortier, E., Melchior, A., Degeest, G., Geeraerts, A., Ivarsson, Y., Depoortere, F., Coomans, C., Vermeiren, E., et al. (2012). Syndecan-syntenin-ALIX regulates the biogenesis of exosomes. Nat. Cell Biol. 14, 677-685.

Becker, A., Thakur, B. K., Weiss, J. M., Kim, H. S., Peinado, H., and Lyden, D. (2016). Extracellular Vesicles in Cancer: Cell-to-Cell Mediators of Metastasis. Cancer Cell 30, 836-848.

Berchem, G., Noman, M. Z., Bosseler, M., Paggetti, J., Baconnais, S., Le Cam, E., Nanbakhsh, A., Moussay, E., Mami-Chouaib, F., Janji, B., et al. (2016). Hypoxic tumor-derived microvesicles negatively regulate NK cell function by a mechanism involving TGF-beta and miR23a transfer. Oncoimmunology 5, e1062968.

Bissig, C., and Gruenberg, J. (2014). ALIX and the multivesicular endosome: ALIX in Wonderland. Trends Cell Biol. 24, 19-25.

Chemnitz, J. M., Parry, R. V., Nichols, K. E., June, C. H., and Riley, J. L. (2004). SHP-1 and SHP-2 associate with immunoreceptor tyrosine-based switch motif of programmed death 1 upon primary human T cell stimulation, but only receptor ligation prevents T cell activation. J. Immunol. 173, 945-954.

Chen, L., and Han, X. (2015). Anti-PD-1/PD-L1 therapy of human cancer: past, present, and future. J. Clin. Invest. 125, 3384-3391.

Chen, Y. et al. (2011) Development of a sandwich ELISA for evaluating soluble PD-L1 (CD274) in human sera of different ages as well as supernatants of PD-L1+ cell lines. Cytokine 56, 231-238.

Chowdhury, S., Veyhl, J., Jessa, F., Polyakova, O., Alenzi, A., MacMillan, C., Ralhan, R., and Walfish, P. G. (2016). Programmed death-ligand 1 overexpression is a prognostic marker for aggressive papillary thyroid cancer and its variants. Oncotarget 7, 32318-32328.

Colombo, M., Moita, C., van Niel, G., Kowal, J., Vigneron, J., Benaroch, P., Manel, N., Moita, L. F., Thery, C., and Raposo, G. (2013). Analysis of ESCRT functions in exosome biogenesis, composition and secretion highlights the heterogeneity of extracellular vesicles. J. Cell Sci. 126, 5553-5565.

Colombo, M., Raposo, G., and Thery, C. (2014). Biogenesis, secretion, and intercellular interactions of exosomes and other extracellular vesicles. Annu. Rev. Cell Dev. Biol. 30, 255-289.

Ding, G., Zhou, L., Qian, Y., Fu, M., Chen, J., Chen, J., Xiang, J., Wu, Z., Jiang, G., and Cao, L. (2015). Pancreatic cancer-derived exosomes transfer miRNAs to dendritic cells and inhibit RFXAP expression via miR-212-3p. Oncotarget 6, 29877-29888.

Dong, H., Strome, S. E., Salomao, D. R., Tamura, H., Hirano, F., Flies, D. B., Roche, P. C., Lu, J., Zhu, G., Tamada, K., et al. (2002). Tumor-associated B7-H1 promotes T-cell apoptosis: a potential mechanism of immune evasion. Nat. Med. 8, 793-800.

Finkelmeier, F., Canli, O., Tal, A., Pleli, T., Trojan, J., Schmidt, M., Kronenberger, B., Zeuzem, S., Piiper, A., Greten, F. R., et al. (2016). High levels of the soluble programmed death-ligand (sPD-L1) identify hepatocellular carcinoma patients with a poor prognosis. Eur. J. Cancer 59, 152-159.

Frigola, X., Inman, B A, Lohse, C. M., Krco, C. J., Cheville, J. C., Thompson, R. H., Leibovich, B., Blute, M. L., Dong, H., and Kwon, E. D. (2011). Identification of a soluble form of B7-H1 that retains immunosuppressive activity and is associated with aggressive renal cell carcinoma. Clin. Cancer Res. 17, 1915-1923.

Garcia-Diaz, A., Shin, D. S., Moreno, B. H., Saco, J., Escuin-Ordinas, H., Rodriguez, G. A., Zaretsky, J. M., Sun, L., Hugo, W., Wang, X., et al. (2017). Interferon Receptor Signaling Pathways Regulating PD-L1 and PD-L2 Expression. Cell Rep. 19, 1189-1201.

Gutierrez-Vazquez, C., Villarroya-Beltri, C., Mittelbrunn, M., and Sanchez-Madrid, F. (2013). Transfer of extracellular vesicles during immune cell-cell interactions. Immunol. Rev. 251, 125-142.

Henne, W. M., Stenmark, H., and Emr, S. D. (2013). Molecular mechanisms of the membrane sculpting ESCRT pathway. Cold Spring. Harb. Perspect. Biol. 5.

Herbst, R. S., Soria, J. C., Kowanetz, M., Fine, G. D., Hamid, O., Gordon, M. S., Sosman, J. A., McDermott, D. F., Powderly, J. D., Gettinger, S. N., et al. (2014). Predictive correlates of response to the anti-PD-L1 antibody MPDL3280A in cancer patients. Nature 515, 563-567.

Horita, H., Law, A., Hong, S., and Middleton, K. (2017). Identifying Regulatory Posttranslational Modifications of PD-L1: A Focus on Monoubiquitinaton. Neoplasia 19, 346-353.

Huang, A. C., Postow, M. A., Orlowski, R. J., Mick, R., Bengsch, B., Manne, S., Xu, W., Harmon, S., Giles, J. R., Wenz, B., et al. (2017). T-cell invigoration to tumour burden ratio associated with anti-PD-1 response. Nature 545, 60-65.

Juneja, V. R., McGuire, K. A., Manguso, R. T., LaFleur, M. W., Collins, N., Haining, W. N., Freeman, G. J., and Sharpe, A. H. (2017). PD-L1 on tumor cells is sufficient for immune evasion in immunogenic tumors and inhibits CD8 T cell cytotoxicity. J. Exp. Med. 214, 895-904.

Kalluri, R. (2016). The biology and function of exosomes in cancer. J. Clin. Invest. 126, 1208-1215.

Kamphorst, A. O., Pillai, R. N., Yang, S., Nasti, T. H., Akondy, R. S., Wieland, A., Sica, G. L., Yu, K., Koenig, L., Patel, N. T., et al. (2017). Proliferation of PD-1+ CD8 T cells in peripheral blood after PD-1-targeted therapy in lung cancer patients. Proc. Natl. Acad. Sci. USA 114, 4993-4998.

Kim, J. W., Wieckowski, E., Taylor, D. D., Reichert, T. E., Watkins, S., and Whiteside, T. L. (2005). Fas ligand-positive membranous vesicles isolated from sera of patients with oral cancer induce apoptosis of activated T lymphocytes. Clin. Cancer Res. 11, 1010-1020.

Larkin, J., Chiarion-Sileni, V., Gonzalez, R., Grob, J. J., Cowey, C. L., Lao, C. D., Schadendorf, D., Dummer, R., Smylie, M., Rutkowski, P., et al. (2015). Combined Nivolumab and Ipilimumab or Monotherapy in Untreated Melanoma. N. Engl. J. Med. 373, 23-34.

Lau, J., Cheung, J., Navarro, A., Lianoglou, S., Haley, B., Totpal, K., Sanders, L., Koeppen, H., Caplazi, P., McBride, J., et al. (2017). Tumour and host cell PD-L1 is required to mediate suppression of anti-tumour immunity in mice. Nat. Commun. 8, 14572.

Li, C. W. et al. (2016). Glycosylation and stabilization of programmed death ligand-1 suppresses T-cell activity. Nat. Commun. 7, 12632.

Lim, S. O., Li, C. W., Xia, W., Cha, J. H., Chan, L. C., Wu, Y., Chang, S. S., Lin, W. C., Hsu, J. M., Hsu, Y. H., et al. (2016). Deubiquitination and Stabilization of PD-L1 by CSNS. Cancer Cell 30, 925-939.

Lo Cicero, A., Stahl, P. D., and Raposo, G. (2015). Extracellular vesicles shuffling intercellular messages: for good or for bad. Curr. Opin. Cell Biol. 35, 69-77.

Mahoney, K. M., Sun, H., Liao, X., Hua, P., Callea, M., Greenfield, E. A., Hodi, F. S., Sharpe, A. H., Signoretti, S., Rodig, S. J., et al. (2015). PD-L1 Antibodies to Its Cytoplasmic Domain Most Clearly Delineate Cell Membranes in Immunohistochemical Staining of Tumor Cells. Cancer Immunol. Res. 3, 1308-1315.

Melo, S. A., Luecke, L. B., Kahlert, C., Fernandez, A. F., Gammon, S. T., Kaye, J., LeBleu, V. S., Mittendorf, E. A., Weitz, J., Rahbari, N., et al. (2015). Glypican-1 identifies cancer exosomes and detects early pancreatic cancer. Nature 523, 177-182.

Mignot, G., Chalmin, F., Ladoire, S., Rebe, C., and Ghirinnghelli, F. (2011). Tumor exosome-mediated MDSC activation. Am. J. Pathol. 178, 1403-1404.

Muller, L., Mitsuhashi, M., Simms, P., Gooding, W. E., and Whiteside, T. L. (2016). Tumor-derived exosomes regulate expression of immune function-related genes in human T cell subsets. Sci. Rep. 6, 20254.

Obeid, J. M., Erdag, G., Smolkin, M. E., Deacon, D. H., Patterson, J. W., Chen, L., Bullock, T. N., and Slingluff, C. L. (2016). PD-L1, PD-L2 and PD-1 expression in metastatic melanoma: Correlation with tumor-infiltrating immune cells and clinical outcome. Oncoimmunology 5, e1235107.

Patel, S. P., and Kurzrock, R. (2015). PD-L1 Expression as a Predictive Biomarker in Cancer Immunotherapy. Mol. Cancer Ther. 14, 847-856.

Peinado, H., Aleckovic, M., Lavotshkin, S., Matei, I., Costa-Silva, B., Moreno-Bueno, G., Hergueta-Redondo, M., Williams, C., Garcia-Santos, G., Ghajar, C., et al. (2012). Melanoma exosomes educate bone marrow progenitor cells toward a pro-metastatic phenotype through MET. Nat. Med. 18, 883-891.

Raposo, G., and Stoorvogel, W. (2013). Extracellular vesicles: exosomes, microvesicles, and friends. J. Cell. Biol. 200, 373-383.

Reck, M., Rodriguez-Abreu, D., Robinson, A. G., Hui, R., Csoszi, T., Fulop, A., Gottfried, M., Peled, N., Tafreshi, A., Cuffe, S., et al. (2016). Pembrolizumab versus Chemotherapy for PD-L1-Positive Non-Small-Cell Lung Cancer. N. Engl. J. Med. 375, 1823-1833.

Ribas, A., Hamid, O., Daud, A., Hodi, F. S., Wolchok, J. D., Kefford, R., Joshua, A. M., Patnaik, A., Hwu, W. J., Weber, J. S., et al. (2016). Association of Pembrolizumab With Tumor Response and Survival Among Patients With Advanced Melanoma. JAMA. 315, 1600-1609.

Robbins, P. D., and Morelli, A. E. (2014). Regulation of immune responses by extracellular vesicles. Nat. Rev. Immunol. 14, 195-208.

Rossille, D., Gressier, M., Damotte, D., Maucort-Boulch, D., Pangault, C., Semana, G., Le Gouill, S., Haioun, C., Tarte, K., Lamy, T., et al. (2014). High level of soluble programmed cell death ligand 1 in blood impacts overall survival in aggressive diffuse large B-Cell lymphoma: results from a French multicenter clinical trial. Leukemia 28, 2367-2375.

Schmidt, O., and Teis, D. (2012). The ESCRT machinery. Curr. Biol. 22, R116-120.

Sznol, M., and Chen, L. (2013). Antagonist antibodies to PD-1 and B7-H1 (PD-L1) in the treatment of advanced human cancer. Clin. Cancer Res. 19, 1021-1034.

Taylor, D. D., Gercel-Taylor, C., Lyons, K. S., Stanson, J., and Whiteside, T. L. (2003). T-cell apoptosis and suppression of T-cell receptor/CD3-zeta by Fas ligand-containing membrane vesicles shed from ovarian tumors. Clin. Cancer Res. 9, 5113-5119.

Thery, C., Amigorena, S., Raposo, G., and Clayton, A. (2006). Isolation and characterization of exosomes from cell culture supernatants and biological fluids. Curr. Protoc. Cell Biol. Chapter 3, Unit 3 22.

Tibes, R. et al. (2006). Reverse phase protein array: validation of a novel proteomic technology and utility for analysis of primary leukemia specimens and hematopoietic stem cells. Mol. Cancer Ther. 5, 2512-2521.

Topalian, S. L., Taube, J. M., Anders, R. A., and Pardon, D. M. (2016). Mechanism-driven biomarkers to guide immune checkpoint blockade in cancer therapy. Nat. Rev. Cancer 16, 275-287.

Tumeh, P. C., Harview, C. L., Yearley, J. H., Shintaku, I. P., Taylor, E. J., Robert, L., Chmielowski, B., Spasic, M., Henry, G., Ciobanu, V., et al. (2014). PD-1 blockade induces responses by inhibiting adaptive immune resistance. Nature 515, 568-571.

Valenti, R., Huber, V., Filipazzi, P., Pilla, L., Sovena, G., Villa, A., Corbelli, A., Fais, S., Parmiani, G., and Rivoltini, L. (2006). Human tumor-released microvesicles promote the differentiation of myeloid cells with transforming growth factor-beta-mediated suppressive activity on T lymphocytes. Cancer Res. 66, 9290-9298.

Wang, L., Wang, H., Chen, H., Wang, W. D., Chen, X. Q., Geng, Q. R., Xia, Z. J., and Lu, Y. (2015). Serum levels of soluble programmed death ligand 1 predict treatment response and progression free survival in multiple myeloma. Oncotarget 6, 41228-41236.

Whiteside, T. L. (2016). Exosomes and tumor-mediated immune suppression. J. Clin. Invest. 126, 1216-1223.

Wieckowski, E. U., Visus, C., Szajnik, M., Szczepanski, M. J., Storkus, W. J., and Whiteside, T. L. (2009). Tumor-derived microvesicles promote regulatory T cell expansion and induce apoptosis in tumor-reactive activated CD8+ T lymphocytes. J. Immunol. 183, 3720-3730.

Zaretsky, J. M., Garcia-Diaz, A., Shin, D. S., Escuin-Ordinas, H., Hugo, W., Hu-Lieskovan, S., Torrejon, D. Y., Abril-Rodriguez, G., Sandoval, S., Barthly, L., et al. (2016). Mutations Associated with Acquired Resistance to PD-1 Blockade in Melanoma. N. Engl. J. Med. 375, 819-829.

Zhou, J., Mahoney, K. M., Giobbie-Hurder, A., Zhao, F., Lee, S., Liao, X., Rodig, S., Li, J., Wu, X., Butterfield, L. H., et al. (2017). Soluble PD-L1 as a Biomarker in Malignant Melanoma Treated with Checkpoint Blockade. Cancer Immunol. Res. 5, 480-492.

While certain of the preferred embodiments of the present invention have been described and specifically exemplified above, it is not intended that the invention be limited to such embodiments. It will be apparent to one skilled in the art that various changes and modifications can be made therein without departing from the scope of the present invention, as set forth in the following claims.

The ASCII text file named "046483-7296US1 Sequence Listing," created on May 5, 2020, comprising 775 bytes, is hereby incorporated by reference in its entirety.

What is claimed is:

1. A method of treating cancer in a subject identified as responsive to anti-cancer therapy, the method comprising
   i) determining the level of extracellular vesicle PD-L1 in a first biological sample obtained from the subject prior to treatment with an anti-cancer agent,
   ii) administering one or more anti-cancer agents to said subject,
   iii) determining the level of extracellular vesicle PD-L1 in a second biological sample obtained from the subject treated with said one or more anti-cancer agents,
   iv) identifying said subject as responsive to treatment where there is an increased level of extracellular vesicle PD-L1 in said second biological sample relative to said first biological sample, and
   v) administering an anti-cancer therapy directed to PD-1 and/or PD-L1 to said subject identified as responsive to treatment,
   wherein the anti-cancer therapy is an anti-PD-1 antibody or an anti-PD-L1 antibody.

2. The method of claim 1, wherein said anti-cancer therapy directed to PD-1/PD-L1 is selected from the group consisting of pembrolizumab, nivolumab, atezolizumab, avelumab, and durvalumab.

3. The method of claim 1, wherein said cancer is melanoma, lung cancer, liver cancer, prostate cancer, colon cancer, kidney cancer, breast cancer, head and neck cancer, bladder cancer, gastric cancer, esophageal cancer, nasopharyngeal cancer, lymphoma, Merkel cell carcinoma, cancer with mismatch repair deficiency, or a cancer that may be treated with anti-PD1/PDL1 therapy.

4. The method of claim 3, wherein said cancer is melanoma or lung cancer.

5. The method of claim 1, wherein the anti-cancer therapy targets PD-1 or the PD-L1 pathway and the second biological sample is collected between 3 to 9 weeks after said therapy, the method further comprising determining the ratio between blood extracellular vesicle PD-L1 protein levels before and after said treatment.

6. The method of claim 1, wherein the biological sample is selected from peripheral blood, serum, plasma, sputum, urine, saliva, ascites or tears.

* * * * *